United States Patent
Resconi et al.

(10) Patent No.: US 9,598,517 B2
(45) Date of Patent: Mar. 21, 2017

(54) CATALYSTS

(71) Applicant: BOREALIS AG, Vienna (AT)

(72) Inventors: Luigi Resconi, Ferrara (IT); Pascal Castro, Helsinki (FI); Ville Virkkunen, Helsinki (FI); Vyatcheslav V. Izmer, Moscow (RU); Dmitry S. Kononovich, Moscow (RU); Pavel Sergeevich Kulyabin, Moscow (RU); Alexander Z. Voskoboynikov, Moscow (RU)

(73) Assignee: Borealis AG, Vienna (AT)

( * ) Notice: Subject to any disclaimer, the term of this patent is extended or adjusted under 35 U.S.C. 154(b) by 0 days.

(21) Appl. No.: 14/654,405

(22) PCT Filed: Dec. 19, 2013

(86) PCT No.: PCT/EP2013/077339
§ 371 (c)(1),
(2) Date: Jun. 19, 2015

(87) PCT Pub. No.: WO2014/096166
PCT Pub. Date: Jun. 26, 2014

(65) Prior Publication Data
US 2015/0344596 A1    Dec. 3, 2015

(30) Foreign Application Priority Data
Dec. 21, 2012  (EP) .................... 12199255

(51) Int. Cl.
*C08F 4/6592* (2006.01)
*C08F 110/06* (2006.01)
(Continued)

(52) U.S. Cl.
CPC ............ *C08F 110/06* (2013.01); *C07C 1/326* (2013.01); *C07F 7/0818* (2013.01); *C07F 17/00* (2013.01);
(Continued)

(58) Field of Classification Search
CPC  C08F 4/65927; C08F 210/06; C08F 4/65912; C08F 110/06
See application file for complete search history.

(56) References Cited

U.S. PATENT DOCUMENTS 6,787,618 B1  9/2004  Winter et al.
7,405,261 B2  7/2008  Schulte et al.
(Continued)

FOREIGN PATENT DOCUMENTS

EP  0537686 A1  4/1993
EP  0776913 A2  6/1997
(Continued)

OTHER PUBLICATIONS

Deng, H. et al., Synthesis of High-Melting, Isotactic Polypropene with $C_2$-Symmetrical Zirconocenes, Macromol, 29, 6371-6376 (1996).
(Continued)

*Primary Examiner* — Caixia Lu
(74) *Attorney, Agent, or Firm* — Ballard Spahr LLP

(57) ABSTRACT

A catalyst comprising
(i) an asymmetric complex of formula (I)

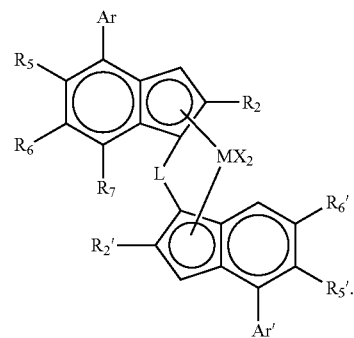

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl or C7-C20-alkylaryl;
$R_2$ and $R_{2'}$ are each independently linear $C_{1-10}$ hydrocarbyl;
$R_5$ and $R_{5'}$ are each independently hydrogen or a C1-20 hydrocarbyl group;
$R_6$ and $R_{6'}$ are each independently hydrogen or a C1-20 hydrocarbyl group;
$R_7$ is hydrogen or a C1-20 hydrocarbyl group or is $ZR_3$;
Z is O or S, preferably O;
$R_3$ is a C1-10 hydrocarbyl group;
Ar is an aryl or heteroaryl group having up to 20 carbon atoms optionally substituted by one or more groups $R_8$;
Ar' is an aryl or heteroaryl group having up to 20 carbon atoms optionally substituted by one or more groups $R_{8'}$; and
$R_8$ and $R_{8'}$ are each independently is a C1-20 hydrocarbyl group;
with the proviso that at least one of $R_6$ or $R_7$ is not H;
and (ii) a cocatalyst comprising a compound of a group 13 metal, e.g. boron.

14 Claims, No Drawings

(51) Int. Cl.
C07F 17/00 (2006.01)
C07C 1/32 (2006.01)
C07F 7/08 (2006.01)
C08F 4/659 (2006.01)

(52) U.S. Cl.
CPC ...... *C08F 4/65927* (2013.01); *C07C 2531/18* (2013.01); *C08F 4/65912* (2013.01)

(56) References Cited

U.S. PATENT DOCUMENTS

| | | | |
|---|---|---|---|
| 9,469,699 | B2 | 10/2016 | Resconi et al. |
| 2003/0149199 | A1* | 8/2003 | Schottek .............. C07F 17/00 526/126 |
| 2004/0260107 | A1* | 12/2004 | Oberhoff .............. B01J 31/143 556/43 |
| 2005/0239979 | A1* | 10/2005 | Schottek .............. C07F 17/00 526/127 |
| 2007/0135596 | A1 | 6/2007 | Voskoboynikov et al. |
| 2009/0163643 | A1 | 6/2009 | Kiss et al. |

FOREIGN PATENT DOCUMENTS

| | | |
|---|---|---|
| EP | 1070729 A2 | 1/2001 |
| EP | 1270614 A2 | 1/2003 |
| EP | 1448578 A1 | 8/2004 |
| EP | 1636245 A1 | 3/2006 |
| EP | 1692144 A2 | 8/2006 |
| EP | 2340649 A1 | 7/2011 |
| EP | 2532687 A2 | 12/2012 |
| EP | 2535372 A1 | 12/2012 |
| WO | WO-01/48034 | 7/2001 |
| WO | WO-02/02575 | 1/2002 |
| WO | WO-02/02576 | 1/2002 |
| WO | WO/02-02576 A1 | 1/2002 |
| WO | WO-03/045551 | 6/2003 |
| WO | WO-03/051934 A2 | 6/2003 |
| WO | WO-2004/106351 A1 | 12/2004 |
| WO | WO-2005/023889 A1 | 3/2005 |
| WO | WO-2005/105863 A2 | 11/2005 |
| WO | WO-2007/107448 A1 | 9/2007 |
| WO | WO-2007/116034 A1 | 10/2007 |
| WO | WO-2007/135596 A1 | 11/2007 |
| WO | WO-2009/054831 A1 | 4/2009 |
| WO | WO-2009/054832 A1 | 4/2009 |
| WO | WO-2009/054833 A2 | 4/2009 |
| WO | WO-2011/076433 A2 | 6/2011 |
| WO | WO-2011/076617 A1 | 6/2011 |
| WO | WO-2014/096164 A1 | 6/2014 |
| WO | WO-2014/096166 A1 | 6/2014 |
| WO | WO-2014/096171 A1 | 6/2014 |
| WO | WO-2014/096282 A1 | 6/2014 |

OTHER PUBLICATIONS

Elder et al., Synthesis and Performance of *ansa*-Metallocene Catalysts with substituted Heterocyclic and Indenyl Ligands, Kinetics and Catalysis, vol. 47, No. 2, 2006, 192-197.

Ewen, J. et al., Chiral *Ansa* Metallocenes with Cp Ring-Fused to Thiophenes and Pyrroles: Syntheses, Crystal Structures, and Isotactic Polypropylene Catalysts, J. Am. Chem. Soc. 2001, 123, 4763-4773.

Ewen, J. et al., Evaluation of the dimethylsiyl-bis(2-methyl-4-phenyl-1-indenyl) ligand with group 4 triad metals in propene polymerizations with methylaluminoxane, Macromol. Rapid Commun. 19, 71-73 (1998).

Izmer, V. et al., Palladium-Catalyzed Pathways to Aryl-Substituted Indenes: Efficient Synthesis of Ligands and the Respective *ansa*-Zirconocenes, Organometallics 2006, vol. 25, No. 5, pp. 1217-1229.

Nifant'ev, Ilya E. et al., 5-Methoxy-Substituted Zirconium Bisindenyl *ansa*-Complexes: Synthesis, Structure, and Catalytic Activity in the Polymerization and Copolymerization of Alkenes, Organometallics, vol. 31, No. 14, 4962-4970 (Jul. 23, 2012).

Nifant'ev, Ilya E. et al., Asymmetric *ansa*-Zirconocenes Containing a 2-Methyl-4-aryltetrahydroindacene Fragment: Synthesis, Structure, and Catalytic Activity in Propylene Polymerization and Copolymerization, Organometallics 2011, 30, 5744-5752.

Spaleck, W. et al., New Bridged zirconocenes for olefin polymerization: Binuclear and hybrid structures, Journal of Molecular Catalysis A: Chemical 128, 279-287 (1998).

Spaleck, W. et al., The Influence of Aromatic Substituents on the Polymerization Behavior of the Bridged Zirconocene Catalysts, Organometallics 1994, vol. 13, No. 3, 954-963.

International Search Report and Written Opinion mailed May 30, 2014 by the International Searching Authority for International Application No. PCT/EP2013/077344, which was published as WO 2014/096171 on Jun. 26, 2014 (Inventor—Castro et al.; Applicant—Borealis AG (13 pages).

International Search Report and Written Opinion mailed May 27, 2014 by the International Searching Authority for International Application No. PCT/EP2013/077339, which was published as WO 2014/096166 on Jun. 26, 2014 (Inventor—Resconi et al.; Applicant—Borealis AG; (13 pages).

International Search Report and Written Opinion mailed May 30, 2014 by the International Searching Authority for International Application No. PCT/EP2013/077335, which was published as WO 2014/096164 on Jun. 26, 2014 (Inventor—Resconi, et al.; Applicant—Borealis AG; (15 pages).

International Search Report and Written Opinion mailed Mar. 3, 2014 by the International Searching Authority for International Application No. PCT/EP2013/077531, which was published as WO 2014/096282 on Jun. 26, 2014 (Inventor—Resconi, et al.; Applicant—Borealis AG; (10 pages).

U.S. Appl. No. 14/654,401, filed Jun. 19, 2015, Castro, P. et al.
U.S. Appl. No. 14/654,409, filed Jun. 19, 2015, Resconi, L. et al.
U.S. Appl. No. 14/654,413, filed Jun. 19, 2015, Resconi, L. et al.

Notice of Allowance issued on Jun. 8, 2016 for U.S. Appl. No. 14/654,409, filed on Jun. 19, 2015 (Applicant—Borealis AG // Inventor—Resconi, et al.) (5 pages).

Notice of Allowance issued by the USPTO on Nov. 2, 2016 for U.S. Appl. No. 14/654,401, filed Jun. 19, 2015 and published a US 2015-0344595 on Dec. 3, 2015 (Applicant—Borealis AG // Inventor—Castro, et al) (9 pages).

\* cited by examiner

1

CATALYSTS

CROSS-REFERENCE TO RELATED APPLICATIONS

This application is a U.S. National Phase Application of International Application No. PCT/EP2013/077339, filed on Dec. 19, 2013, which claims priority to European Patent Application No. 12199255.6, filed Dec. 21, 2012, each of which are hereby incorporated by reference in their entirety.

FIELD OF INVENTION

This invention relates to new polymerization catalysts based on novel bridged bisindenyl metallocene complexes, in particular, solid particulate catalysts containing novel asymmetric bisindenyl metallocene complexes. The invention also relates to the use of such new bisindenyl metallocene catalysts for the production of polypropylene at excellent catalyst activities to give polypropylene homopolymers or copolymers with high molecular weight, and high melting point even at industrially relevant polymerization temperatures.

BACKGROUND OF INVENTION

Metallocene catalysts have been used to manufacture polyolefins for many years. Countless academic and patent publications describe the use of these catalysts in olefin polymerisation. Metallocenes are now used industrially and polyethylenes and polypropylenes in particular are often produced using cyclopentadienyl based catalyst systems with different substitution patterns.

The most important physical properties of isotactic polypropylene (iPP) are its average molecular weight and its melting point (Tm), the latter being mostly determined by the degree of stereoregularity (isotacticity) and regioregularity/total chain defects of the polypropylene chains.

The Ziegler-Natta catalyst systems known in the literature can produce iPP with high molecular weights together with moderate to high isotacticities and melting points (Tm). The Tm (measured by standard DSC methods) of non-nucleated iPPs are in the range of 160 to 165° C.

Since their discovery and for the following ten years of development, metallocene catalysts for polypropylene have been limited in their application because of low activity, their limited molecular weight capability and the relative low melting and low stiffness of the PP homopolymer they could produce. Since 1992, due to improved ligand design, several families of bridged bisindenyl metallocene catalysts have been described, that were able to produce polypropylene homopolymers with increasingly higher molecular weight and higher isotacticity.

However, in the case of metallocenes, there are very few examples which can produce iPP having both very high molecular weights and high melting points. For example rac-Et(2,4,7-Me$_3$Ind)$_2$ZrCl$_2$ can produce isotactic polypropylene with a molecular weight of 1,900,000 g/mol and a melting point of 168° C.

The most successful ligand types are based on the basic 2-methyl-4-aryl-indenyl substitution pattern: for example, rac-Me$_2$Si(2-methyl-4-phenylindenyl)$_2$ZrCl$_2$ was shown to produce homo-PP with a relatively high melting point of 150-151° C. and fairly high molecular weight even at industrial polymerization temperatures. However, these complexes quickly lost their molecular weight capability as soon as ethylene was added to the system, so were unable to produce C$_2$-rich random copolymers or heterophasic copolymers of the appropriate molecular weights.

One solution found to increase the molecular weight of copolymers has been to replace one of the two 2-methyl groups with a branched alkyl group, such as 2-isopropyl. This substitution pattern, which generates a C$_1$-symmetric complex, led to a slight increase in isotacticity of the homopolymer and a marked increase in the molecular weight of the ethylene-propylene copolymers compared to the C$_2$-symmetric rac-Me$_2$Si(2-Me-4-PhInd)$_2$ ligand system.

However, in all cases the increase in molecular weight of the copolymers was obtained at the expense of activity, or catalyst cost, or both.

The present inventors have found that by using a suitable combination of indenyl ligands where both indenes are 2-methyl substituted, and preferably by using particular single site catalyst technology, that ideal polymer properties can be achieved.

The invention also covers a new and improved synthesis of key intermediates needed in the synthesis of the catalysts of the invention.

The catalysts of the invention are new although similar catalysts are of course known in the art. The metallocene rac-Et(2,4,7-Me$_3$Ind)$_2$ZrCl$_2$/MAO is known. In U.S. Pat. No. 7,405,261, rac-Et[2,7-Me$_2$-4-(4-tBuPh)Ind]$_2$ZrCl$_2$ is reported to produce iPP with a melting point of 156° C., by polymerizing liquid propylene at 65° C.

WO2009/054831 describes zirconocenes with a 2-methyl-4,7-aryl substitution pattern, such as rac-Me$_2$Si[2-Me-4,7-(4-tBuPh)$_2$Ind]$_2$ZrCl$_2$. The melting points of the homopolymers are still quite low, being in all cases below 150° C. despite the relatively low polymerization temperature of 65° C.

WO02/02576 describes conventionally supported metallocenes such as rac-Me$_2$Si[2-Me-4-(3,5-tBu$_2$Ph)Ind]$_2$ZrCl$_2$. These metallocene catalysts, activated with MAO or a borate, on a silica support, at a polymerisation temperature of 60 or 70° C., give iPP with Tm between 156 and 159° C.

The metallocene rac-9-silafluorenyl-9,9-[2-Me-4-(3,5-tBu$_2$Ph)Ind]$_2$ZrCl$_2$ also gives high melting point iPP and is described in WO02/02575.

All the above examples are based on C$_2$-symmetric metallocenes, that is those in which both indenyl ligands are identically substituted. The present invention however, is concerned with asymmetrical ligand structures.

There are also several examples of isoselective bisindenyl metallocenes having C$_1$-symmetry, that is metallocene complexes in which the two bridged indenyl ligands have different substitution pattern.

Spaleck et al. in Journal of Molecular Catalysis A: Chemical 128, 1998, 279-287 describes some bisindenyl catalysts which are asymmetric but which lack any substituents on the 6 or 7 position of the 6-membered ring. These complexes, although of relative simple structure, have a quite poor performance in propylene polymerization.

In WO2005/105863 and WO2004/106531, various asymmetric catalysts are disclosed which have a branched alkyl group at the 2-position of the ring. Such catalysts have poor activity. WO2001/048034 also requires branched structures at the 2-position of the metallocenes therein.

EP-A-1692144 describes asymmetrical catalysts based on tricyclic rings.

The present inventors seek alternative asymmetrical catalysts that can allow the formation of interesting iPP and copolymers of polypropylene at high catalyst activities.

Also, in all the above cases, the preparation of the indenes require multistep syntheses which render the ligands quite expensive.

The catalysts of the invention comprise an optionally substituted aryl or heteroaryl group at the 4-position of the indenyl ligands and a linear hydrocarbyl substituent at the 2-position of the indenyl ligands. On one ligand of the catalyst there is a 6 or 7-position group, however, the other ligand does not carry a 7-position group. The metallocenes of the invention are asymmetrical so it is essential that the two ligands differ. Benefits achieved by using catalysts above include random copolymers with higher molecular weight and, in particular, polymerisations in which the catalysts exhibit higher activity. Also, it is believed that the catalysts of the invention allow a higher degree of fine-tuning of their polymerization performance, compared to the conventional symmetrical catalysts.

It is a further preferred advantage that the catalysts of the invention are easy to synthesise.

SUMMARY OF INVENTION

Thus, viewed from one aspect the invention provides a catalyst comprising
(i) an asymmetric complex of formula (I)

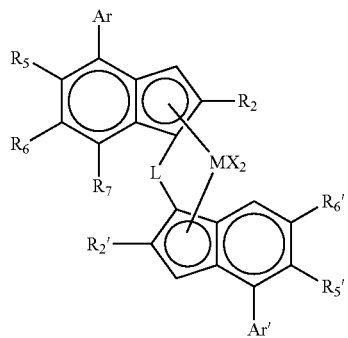

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl or C7-C20-alkylaryl;
$R_2$ and $R_{2'}$ are each independently linear $C_{1-10}$ hydrocarbyl;
$R_5$ and $R_{5'}$ are each independently hydrogen or a C1-20 hydrocarbyl group;
$R_6$ and $R_{6'}$ are each independently hydrogen or a C1-20 hydrocarbyl group;
$R_7$ is hydrogen or a C1-20 hydrocarbyl group or is $ZR_3$;
Z is O or S, preferably O;
$R_3$ is a C1-10 hydrocarbyl group;
Ar is an aryl or heteroaryl group having up to 20 carbon atoms optionally substituted by one or more groups $R_8$;
Ar' is an aryl or heteroaryl group having up to 20 carbon atoms optionally substituted by one or more groups $R_{8'}$;
$R_8$ and $R_{8'}$ are each independently is a C1-20 hydrocarbyl group;
with the proviso that at least one of $R_6$ or $R_7$ is not H; and (ii) a cocatalyst comprising a compound of a group 13 metal, e.g. boron or Al.

The catalyst of the invention can be used in non-supported form or in solid form, optionally on a support. The catalyst of the invention may be used as a homogeneous catalyst or heterogeneous catalyst.

The catalyst of the invention in solid form, preferably in solid particulate form can be either supported on an external carrier material, like silica or alumina, or, in a particularly preferred embodiment, is free from an external carrier, however still being in solid form. Ideally, the solid catalyst is obtainable by a process in which (a) a liquid/liquid emulsion system is formed, said liquid/liquid emulsion system comprising a solution of the catalyst components (i) and (ii) dispersed in a solvent so as to form dispersed droplets; and (b) solid particles are formed by solidifying said dispersed droplets.

Viewed from another aspect the invention provides a process for the manufacture of a catalyst as hereinbefore defined comprising obtaining a complex of formula (I) and a cocatalyst as hereinbefore described;

forming a liquid/liquid emulsion system, which comprises a solution of catalyst components (i) and (ii) dispersed in a solvent, and solidifying said dispersed droplets to form solid particles.

Viewed from another aspect the invention provides the use in olefin polymerisation of a catalyst as hereinbefore defined, especially for the formation of a polyolefin, especially a polyethylene or polypropylene, such as isotactic polypropylene, random propylene copolymer or random heterophasic propylene copolymer.

Viewed from another aspect the invention provides a process for the polymerisation of at least one olefin comprising reacting said at least one olefin with a catalyst as hereinbefore described, especially for the formation of polypropylene, either homopolymers or copolymers such as random copolymers and heterophasic propylene copolymers.

The complexes of the invention are also new and form a further aspect of the invention. Thus, the invention provides a complex of formula (I) as herein before defined. It is also envisaged that the bridged indenyl ligands of the invention (i.e. the ligand before complexation with the metal ion) form a still yet further aspect of the invention.

DEFINITIONS

Throughout the description the following definitions are employed.

By free from an external carrier is meant that the catalyst does not contain an external support, such as an inorganic support, for example, silica or alumina, or an organic polymeric support material.

The term asymmetric means that the top and bottom ligands in the catalyst cannot be the same.

The term $C_{1-20}$ hydrocarbyl group includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups or, of course, mixtures of these groups such as cycloalkyl substituted by alkyl.

Unless otherwise stated, preferred $C_{1-20}$ hydrocarbyl groups are $C_{1-20}$ alkyl, $C_{4-20}$ cycloalkyl, $C_{5-20}$ cycloalkyl-alkyl groups, $C_{7-20}$ alkylaryl groups, $C_{7-20}$ arylalkyl groups or $C_{6-20}$ aryl groups, especially $C_{1-10}$ alkyl groups, $C_{6-10}$ aryl groups, or $C_{7-12}$ arylalkyl groups, e.g. $C_{1-8}$ alkyl groups. Most especially preferred hydrocarbyl groups are methyl, ethyl, propyl, isopropyl, tertbutyl, isobutyl, $C_{5-6}$-cycloalkyl, cyclohexylmethyl, phenyl or benzyl.

Linear $C_{1-10}$ hydrocarbyl group includes linear $C_{1-10}$ alkyl, linear $C_{2-10}$ alkenyl, linear $C_{2-10}$ alkynyl, preferably linear $C_{1-6}$ alkyl, linear $C_{2-6}$ alkenyl, linear $C_{2-6}$ alkynyl, more preferably linear $C_{1-6}$ alkyl, and still more preferably a methyl, ethyl or n-propyl group, ideally a methyl group.

The term halo includes fluoro, chloro, bromo and iodo groups, especially chloro groups, when relating to the complex definition.

The term heterocyclic group means a preferably monocyclic non aromatic ring structure comprising at least one heteroatom, e.g. piperidinyl or piperazinyl.

The term heteroaryl means a preferably monocyclic aromatic ring structure comprising at least one heteroatom. Preferred heteroaryl groups have 1 to 4 heteroatoms selected from O, S and N. Preferred heteroaryl groups include furanyl, thiophenyl, oxazole, thiazole, isothiazole, isooxazole, triazole and pyridyl.

The oxidation state of the metal ion is governed primarily by the nature of the metal ion in question and the stability of the individual oxidation states of each metal ion.

It will be appreciated that in the complexes of the invention, the metal ion M is coordinated by ligands X so as to satisfy the valency of the metal ion and to fill its available coordination sites. The nature of these σ-ligands can vary greatly.

Catalyst activity is defined in this application to be the amount of polymer produced/g catalyst/h. Catalyst metal activity is defined here to be the amount of polymer produced/g Metal/h. The term productivity is also sometimes used to indicate the catalyst activity although herein it designates the amount of polymer produced per unit weight of catalyst.

DETAILED DESCRIPTION OF INVENTION

The catalyst of the invention can be used in supported or unsupported form. Preferably it is provided in solid particulate form but without the use of an external carrier. Suitable mean particle size for solid particulate catalysts are in the range of 2 to 150 µm.

The complexes of the invention are asymmetrical. That means simply that the two indenyl ligands forming the metallocene are different, that is, each indenyl ligand bears a set of substituents that are either chemically different, or located in different positions with respect to the other indenyl ligand. More precisely, they are chiral, racemic bridged bisindenyl metallocenes. Whilst the complexes of the invention may be in their syn configuration, ideally, they are in their anti configuration. For the purpose of this invention, racemic-anti means that the two indenyl ligands are oriented in opposite directions with respect to the cyclopentadienyl-metal-cyclopentadienyl plane, while racemic-syn means that the two indenyl ligands are oriented in the same direction with respect to the cyclopentadienyl-metal-cyclopentadienyl plane, as shown in the Figure below.

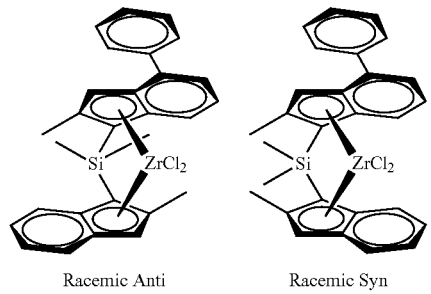

Racemic Anti    Racemic Syn

Formula (I) is intended to cover both syn and anti configurations, preferably anti.

It is preferred if the metallocenes of the invention are employed as the rac anti isomer. Ideally therefore at least 95% mol, such as at least 98% mol, especially at least 99% mol of the metallocene is in the racemic anti isomeric form.

In the preferred complexes of formula (I)

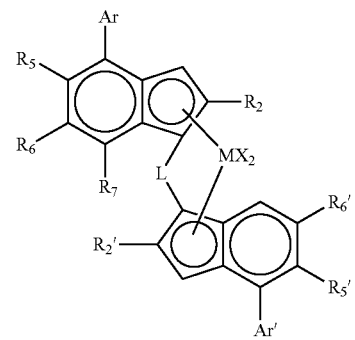

each X, which may be the same or different, is preferably a hydrogen atom, a halogen atom, a R, OR, $OSO_2CF_3$, OCOR, SR, $NR_2$ or $PR_2$ group wherein R is a linear or branched, cyclic or acyclic, C1-C20-alkyl, C2-C20 alkenyl, C2-C20 alkynyl, C6-C20-aryl, C7-C20-alkylaryl or C7-C20-arylalkyl radical; optionally containing heteroatoms belonging to groups 14-16. R is preferably a $C_{1-6}$ alkyl, phenyl or benzyl group.

Most preferably each X is independently a hydrogen atom, a halogen atom, $C_{1-6}$-alkoxy group or an R group, e.g. preferably a $C_{1-6}$-alkyl, phenyl or benzyl group. Most preferably X is chlorine or a methyl radical. Preferably both X groups are the same.

L is preferably a bridge comprising a heteroatom, such as silicon or, germanium, e.g. —$SiR^9_2$—, wherein each $R^9$ is independently C1-C20-alkyl, C5-10 cycloalkyl, C6-C20-aryl or tri(C1-C20-alkyl)silyl-residue, such as trimethylsilyl. More preferably $R^9$ is $C_{1-6}$-alkyl, especially methyl. Most preferably, L is a dimethylsilyl or diethylsilyl bridge. It may also be an ethylene bridge.

The Ar and Ar' groups are preferably a C6-20 aryl group such as a phenyl group or naphthyl group. The Ar group can also be a heteroaryl group, such as carbazolyl. The Ar group can be unsubstituted but is preferably substituted by one or more groups $R_8$ or $R_{8'}$. If substituted by two $R_8$ or $R_{8'}$ groups, they are especially in positions 3 and 5 of the aryl ring bound to the indenyl ligand.

Preferably at least one $R_8$ or $R_{8'}$ group is present on the Ph rings at the 4-position of the indenyl ligand. It is preferred if all $R_8$ and $R_{8'}$ groups are the same. It is preferred however, if 1 or 2 such groups are present, i.e. n and n' are 1 or 2 (in the formulae which follow). In particular, 2 groups should be positioned at the 3 and 5 positions of the Ph ring bound to the indenyl ligand.

$R_8$ and $R_{8'}$ are preferably a C1-20 hydrocarbyl group, such as a C1-20 alkyl group or C6-10 aryl group. $R_8$ and $R_{8'}$ groups can be the same or different, preferably the same. More preferably, $R_8$ and $R_{8'}$ are a C2-10 alkyl group such as C3-8 alkyl groups. Highly preferred groups are tert butyl groups. It is preferred if the $R_8$ and $R_{8'}$ group is bulky, i.e. is branched. Branching might be alpha or beta to the Ph ring. Branched C3-8 alkyl groups are also favoured therefore.

In one embodiment, it is preferred if the substitution pattern on the Ar' group is different from the Ar group. In particular, there are two $R_8$ groups and one $R_{8'}$ group present.

If one substituent $R_8$ or $R_{8'}$ is present then it is preferably in the para position on the ring.

$R_2$ and $R_2'$ are preferably each independently linear C1-6 alkyl, more preferably linear C1-4 alkyl, especially methyl, ethyl or n-propyl, ideally methyl. $R_2$ and $R_2'$ are preferably the same.

$R_5$ and $R_{5'}$ are preferably hydrogen or a C1-10 alkyl group, such as methyl. Ideally $R_5$ and $R_{5'}$ are hydrogen.

$R_6$ is preferably hydrogen or a C1-10 alkyl group, such as methyl or C3-8 alkyl. Ideally $R_6$ is hydrogen or C1-6 alkyl.

$R_{6'}$ is preferably hydrogen or a C1-10 alkyl group. Ideally $R_{6'}$ is hydrogen.

The $R_7$ group can be H (when $R_6$ is not H). Preferably however $R_7$ is not H. It can be a C1-10 alkyl group or a group $-ZR_3$.

Z is O or S, preferably O. It is highly preferred therefore if the 7-position substituent is $OR_3$.

$R_3$ is preferably an aliphatic C1-10 hydrocarbyl group, especially a C1-10 alkyl group, more especially a C1-6 alkyl group. Most especially $R_3$ is a C1-4 alkyl group, such as a linear C1-4 alkyl group. Ideally it is methyl or ethyl.

One of $R_6$ and $R_7$ is not hydrogen. It is preferred if one of $R_6$ and $R_7$ is hydrogen.

Preferred catalysts of the invention therefore comprise an asymmetric complex of formula (II)

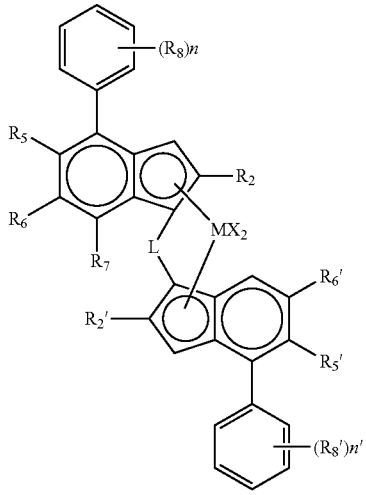

M is zirconium or hafnium;
each X is a sigma ligand;
L is a divalent bridge selected from $-R'_2C-$, $-R'_2C-CR'_2-$, $-R'_2Si-$, $-R'_2Si-SiR'_2-$, $-R'_2Ge-$, wherein each R' is independently a hydrogen atom, C1-C20-alkyl, tri(C1-C20-alkyl)silyl, C6-C20-aryl, C7-C20-arylalkyl or C7-C20-alkylaryl;
$R_2$ and $R_{2'}$ are each independently linear C1-4 alkyl;
$R_5$ and $R_{5'}$ are each independently hydrogen or an aliphatic C1-10 hydrocarbyl group;
$R_6$ and $R_{6'}$ are each independently hydrogen or an aliphatic C1-10 hydrocarbyl group;
$R_7$ is hydrogen or an aliphatic C1-10 hydrocarbyl group or is $ZR_3$;
Z is O or S, preferably O;
$R_3$ is a C1-10 alkyl group;
$R_8$ and $R_{8'}$ are each independently is an aliphatic C1-20 hydrocarbyl group.
n is 0, 1, 2 or 3;
n' is 0, 1, 2 or 3;
with the proviso that one of $R_6$ and $R_7$ is not H. It is preferred if one of $R_6$ and $R_7$ is hydrogen.

More preferred asymmetric complexes of the invention are of formula (III)

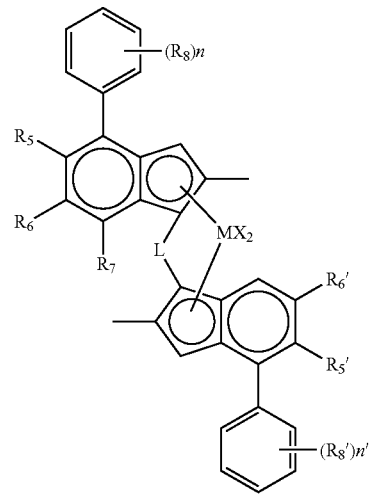

wherein
M is zirconium or hafnium;
each X is a sigma ligand, preferably each X is independently a hydrogen atom, a halogen atom, $C_{1-6}$-alkoxy group, $C_{1-6}$-alkyl, phenyl or benzyl group;
L is a divalent bridge selected from $-R'_2C-$, $-R'_2C-CR'_2-$, $-R'_2Si-$, $-R'_2Si-SiR'_2-$, $-R'_2Ge-$, wherein each R' is independently a hydrogen atom, C1-C20-alkyl, tri(C1-C20-alkyl)silyl, C6-C20-aryl, C7-C20-arylalkyl or C7-C20-alkylaryl; preferably dimethylsilyl, methylene or ethylene;
$R_5$ and $R_{5'}$ are hydrogen or a C1-10 alkyl group;
$R_6$ and $R_{6'}$ are hydrogen or a C1-10 alkyl group;
$R_7$ is hydrogen or C1-10 alkyl group or is $OR_3$;
$R_3$ is a C1-10 alkyl group;
n is 1 to 3, e.g. 2;
n' is 1 to 3, e.g. 1;
and $R_8$ and $R_{8'}$ are an aliphatic C1-10 hydrocarbyl group;
with the proviso that one of $R_6$ and $R_7$ is not H. It is preferred if one of $R_6$ and $R_7$ is hydrogen.

Still more preferred asymmetric complexes of the invention are of formula (IV):

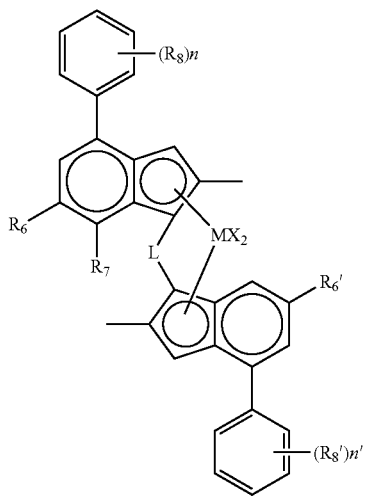

wherein

M is zirconium or hafnium;

each X is a sigma ligand, preferably each X is independently a hydrogen atom, a halogen atom, $C_{1-6}$-alkoxy group, $C_{1-6}$-alkyl, phenyl or benzyl group;

L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-hydrocarbyl, tri(C1-C20-alkyl)silyl, C6-C20-aryl, C7-C20-arylalkyl or C7-C20-alkylaryl; preferably dimethylsilyl $R_6$ is hydrogen or a C1-10 alkyl group;

$R_{6'}$ is hydrogen or a C1-10 alkyl group;

$R_7$ is hydrogen or C1-10 alkyl group or is $OR_3$;

$R_3$ is a C1-10 alkyl group;

n is 1 to 3, e.g. 2;

n' is 1 to 3, e.g. 1;

and $R_8$ and $R_{8'}$ are a C1-10 alkyl group;

with the proviso that one of $R_6$ and $R_7$ is not H. It is preferred if one of $R_6$ and $R_7$ is hydrogen.

Still more preferred asymmetric complexes of the invention are of formula (V)

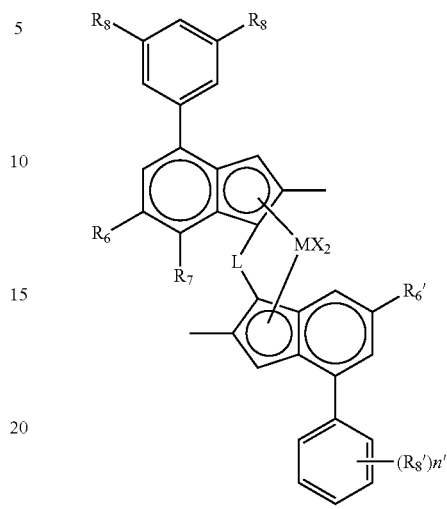

wherein L, M and X are as hereinbefore defined (e.g. in formula (II-IV));

$R_6$ is hydrogen or a C1-6 alkyl group;

$R_{6'}$ is hydrogen or a C1-6 alkyl group;

$R_7$ is hydrogen or C1-6 alkyl group or is $OR_3$;

$R_3$ is preferably an C1-6 alkyl group;

n' is 1 to 3, e.g. 1;

and $R_8$ and $R_{8'}$ are a C1-10 alkyl group, e.g. C3-8 alkyl group;

with the proviso that one of $R_6$ and $R_7$ is not H. It is preferred if one of $R_6$ and $R_7$ is H. It is also preferred in formula (V) that n' is 1 and the substituent is para to the indenyl.

Ligand structures of interest are summarised below. Those in the top row are equivalent to the top ligand in the formulae above. Those in the left column are the bottom ligand in the formulae above.

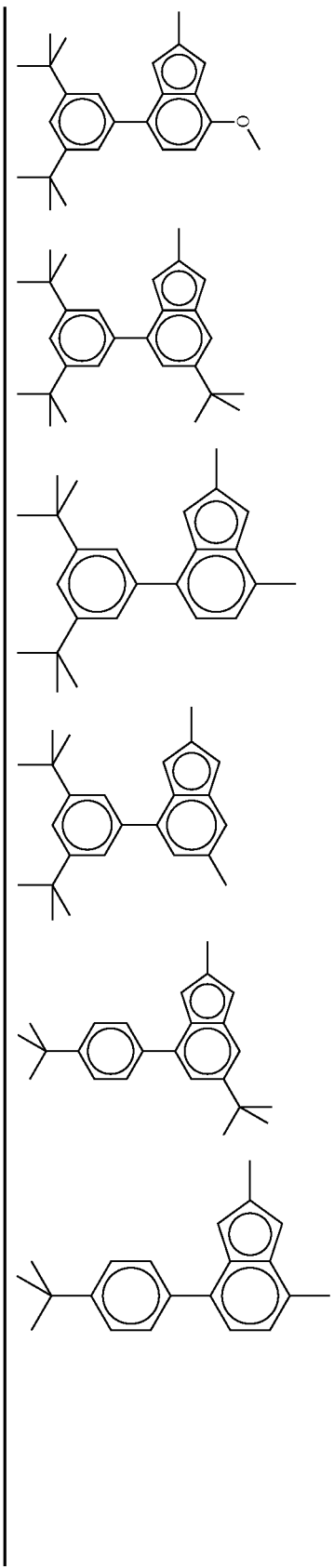
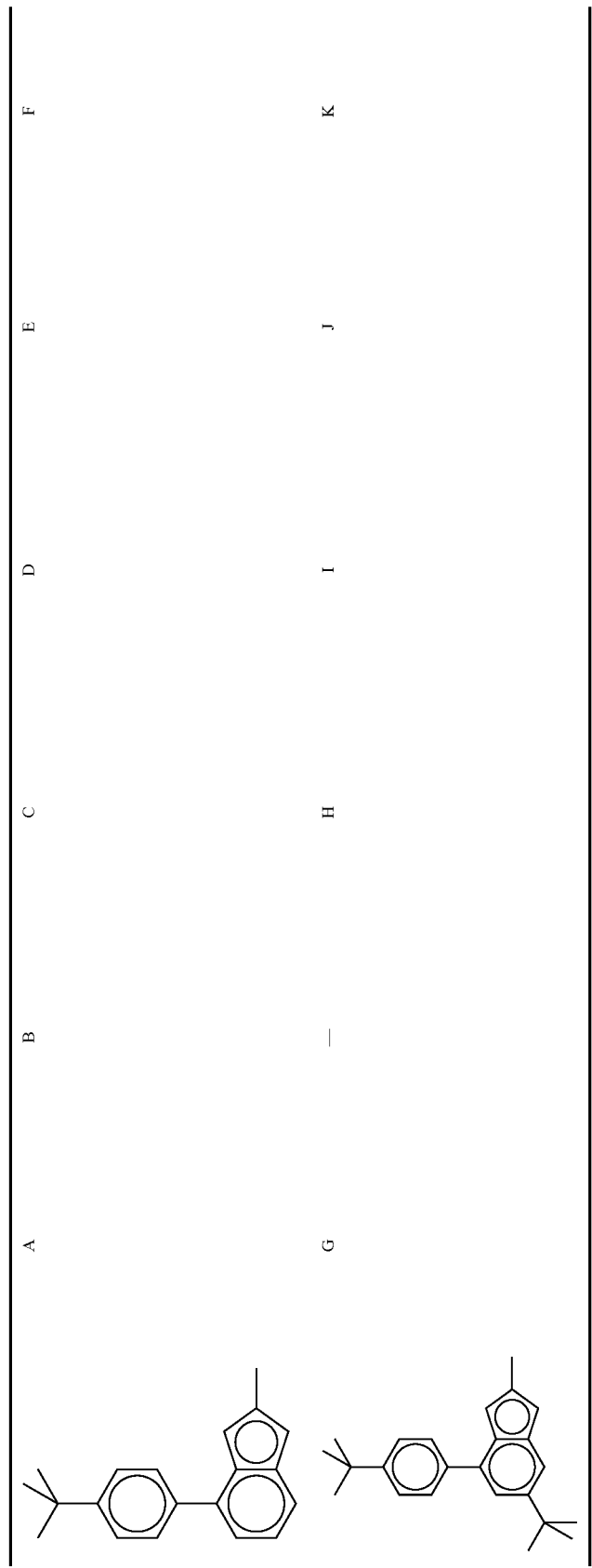

Highly preferred complexes of the invention are
rac-anti-Me$_2$Si(2-Me-4-(3,5-tBu$_2$Ph)-7-OMe-Ind)(2-Me-4-(p-tBuPh)-Ind)ZrCl$_2$ (MC1):

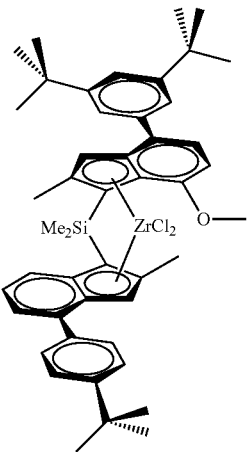

rac-anti-Me$_2$Si(2-Me-4-(3,5-tBu$_2$Ph)-7-Me-Ind)(2-Me-4-(p-tBuPh)-Ind)ZrCl$_2$ (MC2)

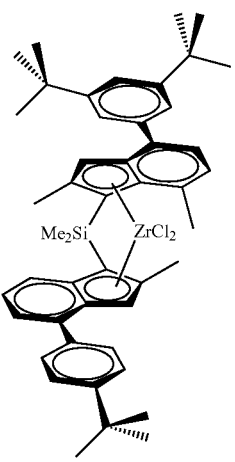

rac-anti-Me$_2$Si(2-Me-4-(3,5-tBu$_2$Ph)-7-OMe-Ind)(2-Me-4-(4-tBuPh)-6-tBu-Ind)ZrCl$_2$ (MC3)

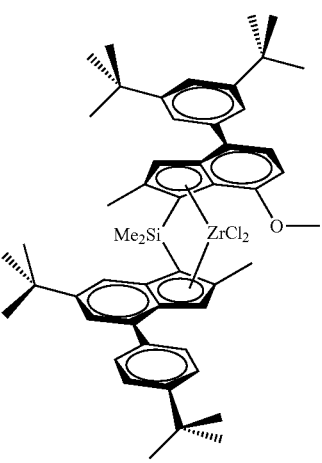

rac-anti-Me$_2$Si(2-Me-4-(p-tBuPh)Ind)(2-Me-4-(3,5-di-tBuPh)-6-tBu-Ind)ZrCl$_2$ (MC4)

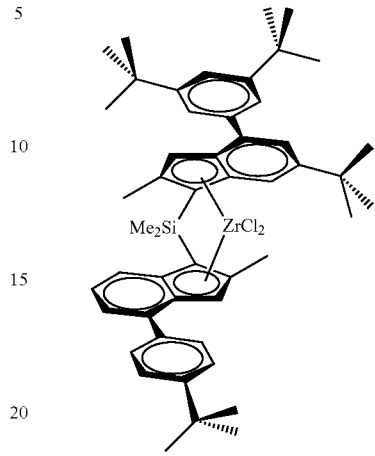

For the avoidance of doubt, any narrower definition of a substituent offered above can be combined with any other broad or narrowed definition of any other substituent.

Throughout the disclosure above, where a narrower definition of a substituent is presented, that narrower definition is deemed disclosed in conjunction with all broader and narrower definitions of other substituents in the application.

Synthesis

The ligands required to form the complexes and hence catalysts of the invention can be synthesised by any process and the skilled organic chemist would be able to devise various synthetic protocols for the manufacture of the necessary ligand materials. In particular WO02/02576 describes suitable synthetic protocols.

It is envisaged that the presence of bulky groups on the Ph group on the 4-position of the indenyl ring ensures the desired regioselectivity during the silylation step at position 1. The Ph group at the 4-position may carry one or two substituents, in particular substituents such as methyl, iso-propyl, neopentyl, tert-butyl or phenyl. Ideally, such bulky substituents are in the 3,5-positions of the 4-substituent or just in the 4-position on the phenyl ring. Ideally they are tert-butyl groups.

A conventional synthesis for ligands of formula (I) is given in WO02/02576. The key indene ligand precursor is shown in Scheme 1 below for the most preferred ligand uses herein:

Scheme 1: synthesis of 4-(3′,5′-di-tertbutylphenyl)-2-methyl-indene

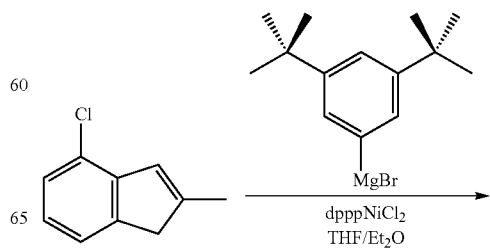

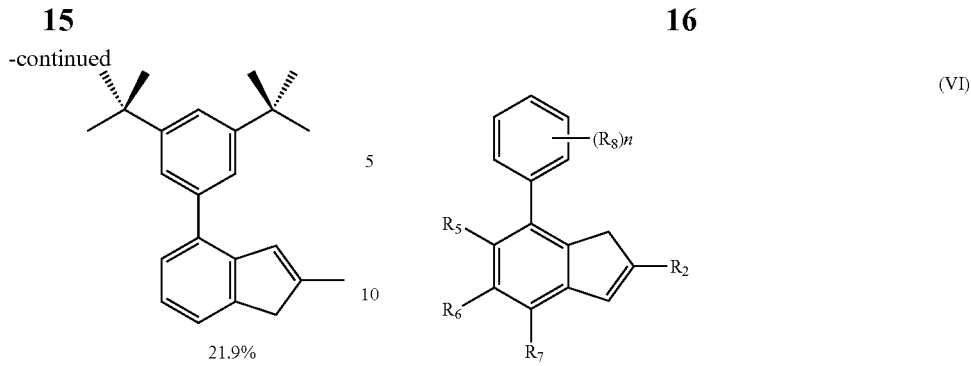

21.9%

The present inventors have devised a new procedure for the formation of this key intermediate which forms a further aspect of the invention.

The new procedure is shown in Scheme 2:

Scheme 2: synthesis of 7-(3′,5′-di-tertbutylphenyl)-2-methyl-indene

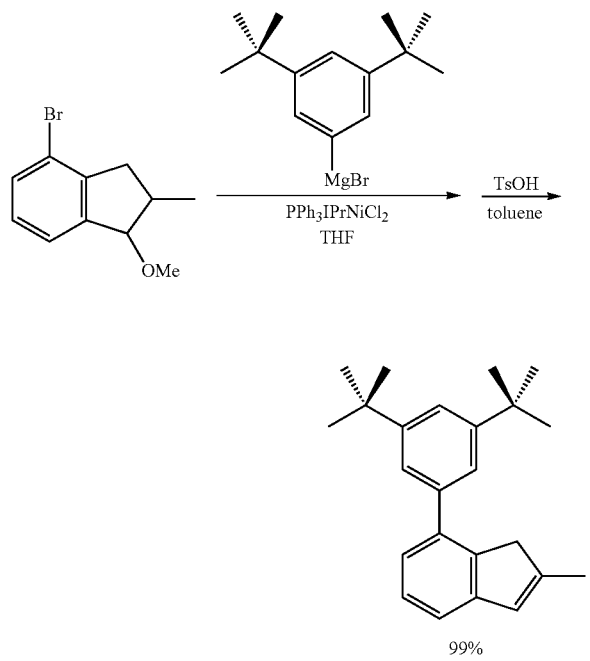

99%

This process seems to lead to a much higher yield of key intermediate. The first step of this "one-pot" sequence is a Ni-catalyzed Kumada coupling, where the bromine atom in the indene 6-membered ring gets substituted with a di(tert-butyl)phenyl moiety). In order to obtain an indene i.e. formally eliminate MeOH and form a carbon-carbon double bond, an acid-catalyzed elimination using a dean-stark apparatus is used. TsOH can be used as an acid catalyst and toluene can be employed to remove water/methanol azeotropically. This reaction is therefore of interest in the formation of the ligands required to form the complexes of the invention.

Thus, viewed from another aspect the invention provides a process for the preparation of a compound of formula (VI):

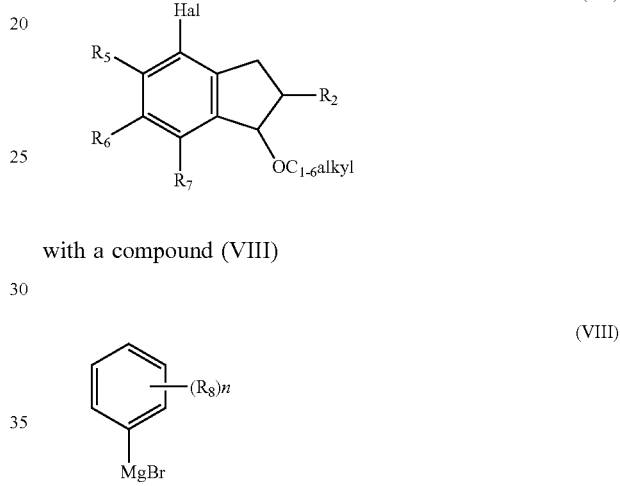

comprising at least the step of reacting a compound of formula (VII)

(VII)

with a compound (VIII)

(VIII)

wherein $R_2$ and $R_{2'}$ are each independently linear $C_{1-10}$ hydrocarbyl;

$R_5$ is hydrogen or a C1-20 hydrocarbyl group;

$R_6$ is hydrogen or a C1-20 hydrocarbyl group;

$R_7$ is hydrogen or a C1-20 hydrocarbyl group or is $ZR_3$;

Z is O or S, preferably O;

$R_3$ is a C1-10 hydrocarbyl group;

$R_8$ is a C1-20 hydrocarbyl group;

n is 0-3; and

Hal is a halide, preferably Br;

in the presence of $PPh_3IPrNiCl_2$.

In this reagent, IPr represents 1,3-bis(2,6-diisopropylphenyl)imidazolidin-2-ylidene. It is believed that other related imidazolidin-2-ylidene carbenes could also be used instead, e.g. those with groups other than 1,3-bis(2,6-diisopropylphenyl) such as 1,3-bis(2,4,6-trimethylphenyl). It will be appreciated that the reaction can take place in a solvent such as THF.

The alkoxy group in formula (VII) is preferably MeO—. The halide is preferably Br.

It will be appreciated that the ligand formed in this process is preferably that required to form the complexes of formula (II), (III), (IV) or (V), e.g. those in table A above.

The starting materials required to manufacture the catalysts of the invention can be made according to the following scheme (suitably adapted for other compounds obviously).

Scheme 3.
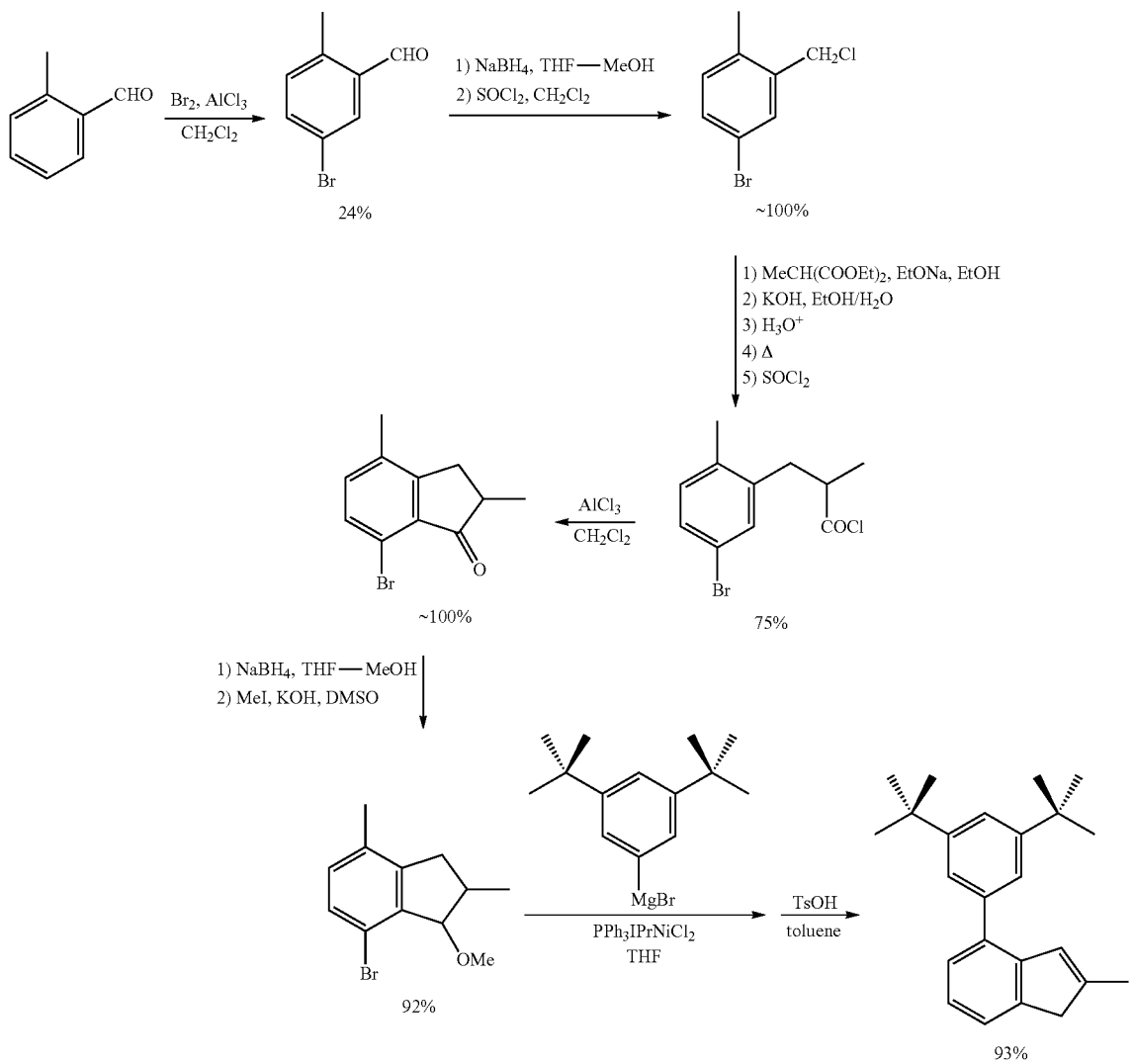
Other indenes of interest in the manufacture of the catalysts of the invention can be made according to scheme 4.
Scheme 4
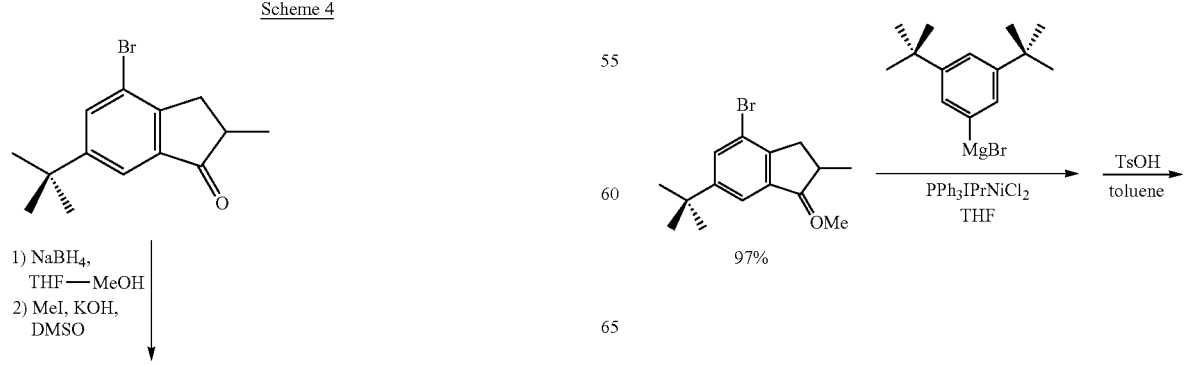

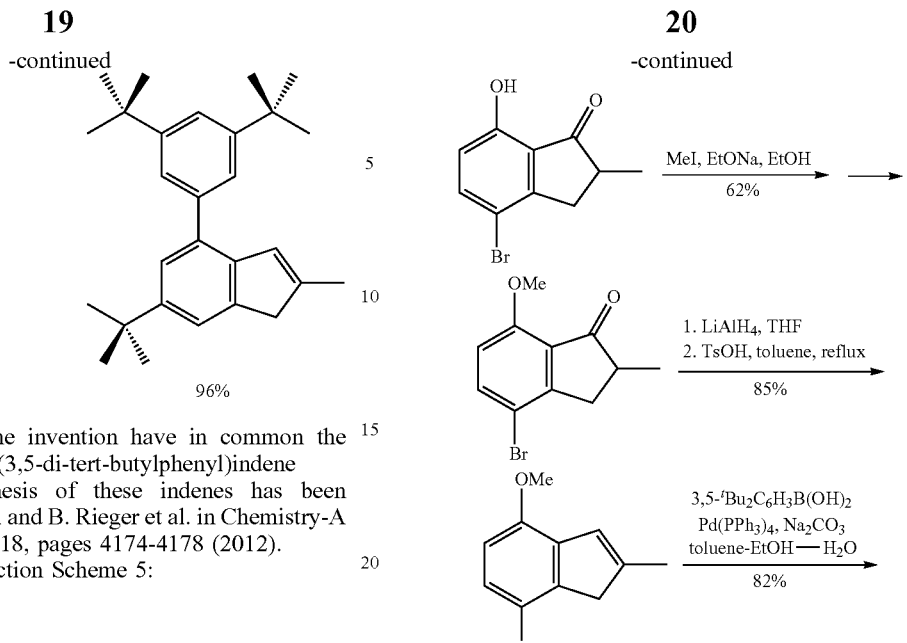

96%

Some complexes of the invention have in common the 2-methyl-4-methoxy-7-(3,5-di-tert-butylphenyl)indene compound. The synthesis of these indenes has been described by A. Schöbel and B. Rieger et al. in Chemistry-A European Journal, vol. 18, pages 4174-4178 (2012).

This is shown in reaction Scheme 5:

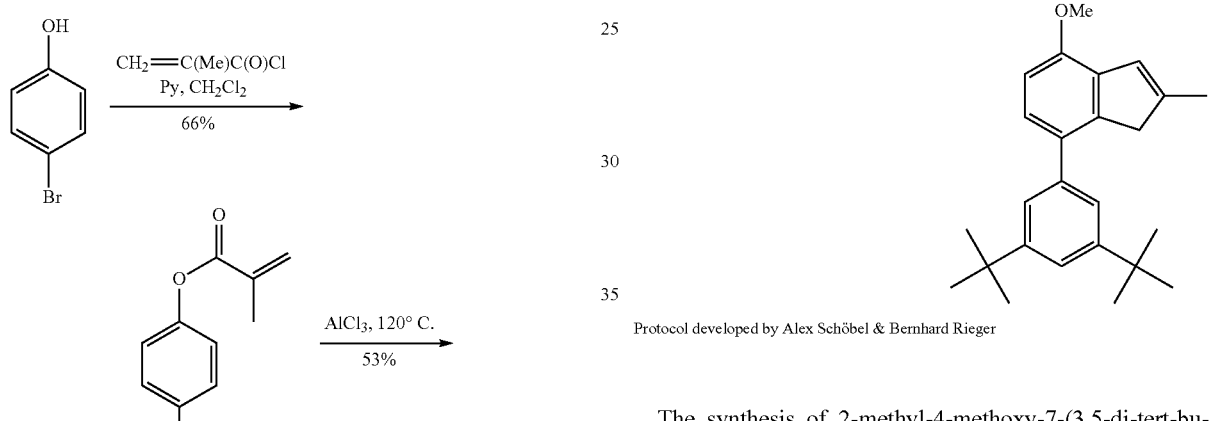

Scheme 5: synthesis of 2-Me-4-OMe-7-(3,5-tBu$_2$Ph)indene

Protocol developed by Alex Schöbel & Bernhard Rieger

The synthesis of 2-methyl-4-methoxy-7-(3,5-di-tert-butylphenyl)indene has now been improved with respect to the known one, as shown in the schemes below:

Scheme 6a: two alternative reaction sequences for the 2-step synthesis of 1-bromo-2-bromomethyl-4-methoxybenzene

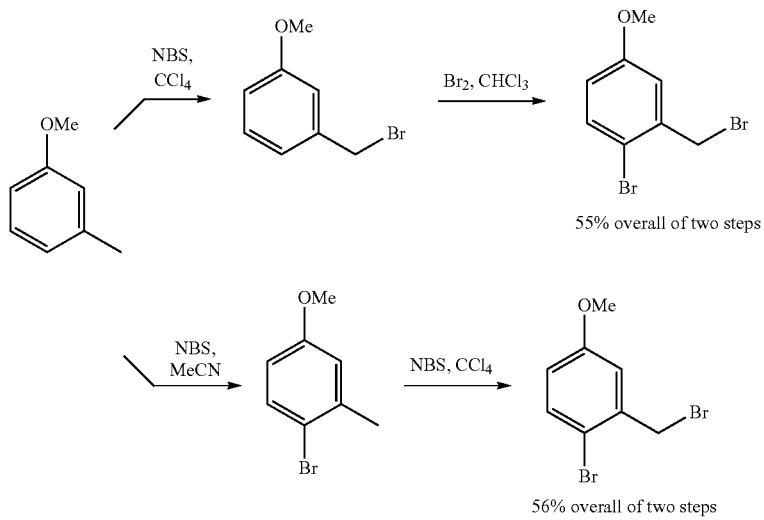

55% overall of two steps

56% overall of two steps

Scheme 6b: 1-step synthesis of 1-bromo-2-bromomethyl-4-methoxybenzene

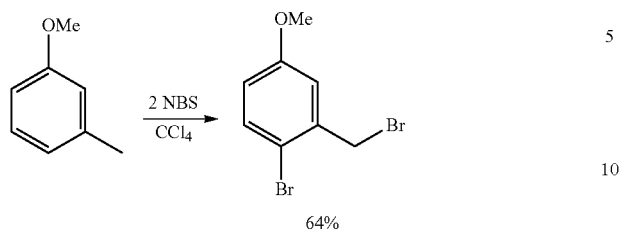

Scheme 7: synthesis of 2-Me-4-OMe-7-(3,5-tBu₂Ph)indene

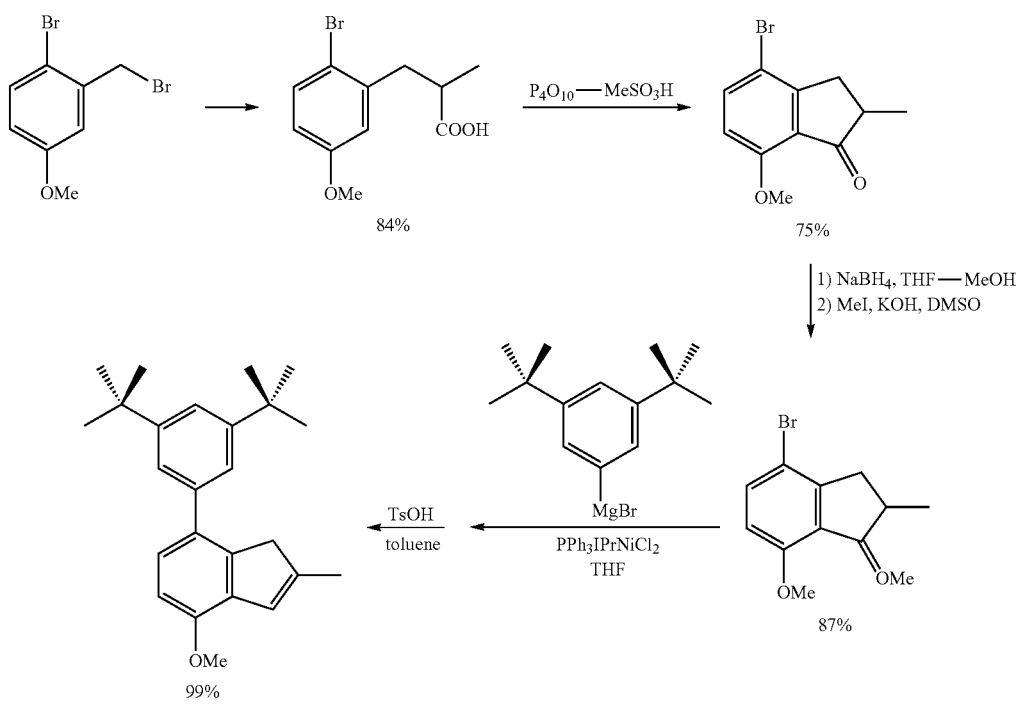

The overall yield of the combined sequences shown in schemes 6b and 7 is about 35%, more than twice as much as the one obtained following the sequence of scheme 5.

This reaction sequence is versatile with respect to the aryl substituent in position 7 (position 4 in the final ligand), and shows that the indenyl ligands chosen for this class of metallocenes can be made readily available.

As well as the last step in the process featuring the use of the Ni catalyst, the whole synthesis forms a further aspect of the invention.

Thus viewed from another aspect the invention provides a process involving the following transformations:

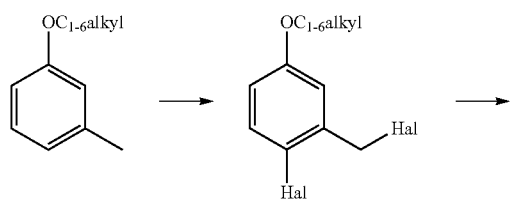

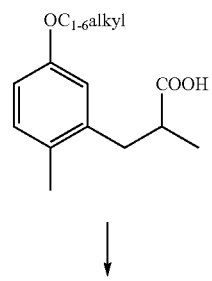

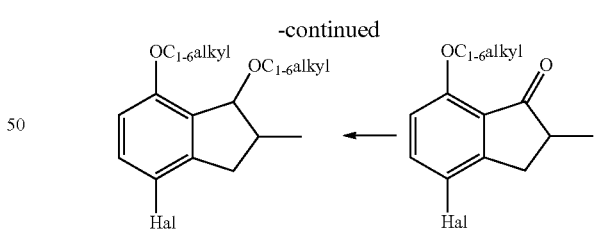

Ideally the product above is compound VII and is reacted with compound VIII in the process described above.

Intermediates

Whilst the invention primarily relates to catalysts, it will be appreciated that the complexes of the invention and the ligands used to form those complexes are also new. The invention further relates therefore to complexes of formula (I) to (V) from which the $MX_2$ coordination has been removed and the proton returned to the indenyl.

Ligands of interest are therefore of formula (I')

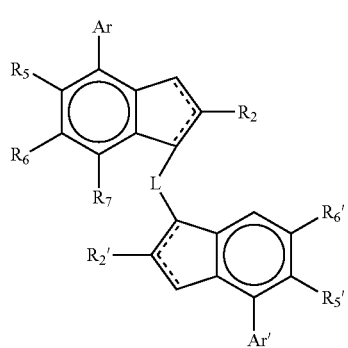

(I')

wherein the substituents are as hereinbefore defined and the dotted lines represent a double bond present in between carbons 1 and 2 or 2 and 3 of the indenyl ring. It will be appreciated therefore that this molecule contains double bond isomers. By double bond isomers is meant the compounds where the double bond is positioned between the 2 and 3 atoms rather than 1 and 2 atoms of the bicyclic ring. It may be that more than one double bond isomer is present in a sample. Preferred ligands are analogues of the complexes described above from which $MX_2$ coordination has been removed and the proton returned to the indenyl.

Cocatalyst

To form an active catalytic species it is normally necessary to employ a cocatalyst as is well known in the art. Cocatalysts comprising an organometallic compound of Group 13 metal, like organoaluminium compounds used to activate metallocene catalysts are suitable for use in this invention.

The olefin polymerisation catalyst system of the invention therefore comprises (i) a complex of the invention; and normally (ii) an aluminium alkyl compound (or other appropriate cocatalyst), or the reaction product thereof. Thus the cocatalyst is preferably an alumoxane, like MAO or an alumoxane other than MAO.

Alternatively, however, the catalysts of the invention may be used with other cocatalysts, e.g. boron compounds. It will be appreciated by the skilled man that where boron based cocatalysts are employed, it is normal to preactivate the complex by reaction thereof with an aluminium alkyl compound, such as TIBA. This procedure is well known and any suitable aluminium alkyl, e.g. $Al(C_{1-6}-alkyl)_3$, can be used.

Boron based cocatalysts of interest include those of formula $BY_3$ wherein Y is the same or different and is a hydrogen atom, an alkyl group of from 1 to about 20 carbon atoms, an aryl group of from 6 to about 15 carbon atoms, alkylaryl, arylalkyl, haloalkyl or haloaryl each having from 1 to 10 carbon atoms in the alkyl radical and from 6-20 carbon atoms in the aryl radical or fluorine, chlorine, bromine or iodine. Preferred examples for Y are methyl, propyl, isopropyl, isobutyl or trifluoromethyl, unsaturated groups such as aryl or haloaryl like phenyl, tolyl, benzyl groups, p-fluorophenyl, 3,5-difluorophenyl, pentachlorophenyl, pentafluorophenyl, 3,4,5-trifluorophenyl and 3,5-di(trifluoromethyl) phenyl. Preferred options are trifluoroborane, triphenylborane, tris(4-fluorophenyl)borane, tris(3,5-difluorophenyl)borane, tris(4-fluoromethylphenyl)borane, tris(2,4,6-trifluorophenyl)borane, tris(penta-fluorophenyl)borane, tris(tolyl)borane, tris(3,5-dimethyl-phenyl)borane, tris(3,5-difluorophenyl)borane and/or tris (3,4,5-trifluorophenyl)borane.

Particular preference is given to tris(pentafluorophenyl) borane.

It is preferred however if borates are used, i.e. compounds containing a borate 3+ ion. Such ionic cocatalysts preferably contain a non-coordinating anion such as tetrakis(pentafluorophenyl)borate and tetraphenylborate. Suitable counterions are protonated amine or aniline derivatives such as methylammonium, anilinium, dimethylammonium, diethylammonium, N-methylanilinium, diphenylammonium, N,N-dimethylanilinium, trimethylammonium, triethylammonium, tri-n-butylammonium, methyldiphenylammonium, pyridinium, p-bromo-N,N-dimethylanilinium or p-nitro-N,N-dimethylanilinium.

Preferred ionic compounds which can be used according to the present invention include: triethylammoniumtetra (phenyl)borate, tributylammoniumtetra(phenyl)borate, trimethylammoniumtetra(tolyl)borate, tributylammoniumtetra (tolyl)borate, tributylammoniumtetra(pentafluorophenyl) borate, tripropylammoniumtetra(dimethylphenyl)borate, tributylammoniumtetra(trifluoromethylphenyl)borate, tributylammoniumtetra(4-fluorophenyl)borate, N,N-dimethylcyclohexylammoniumtetrakis(pentafluorophenyl)borate, N,N-dimethylbenzylammoniumtetrakis(pentafluorophenyl) borate, N,N-dimethylaniliniumtetra(phenyl)borate, N,N-diethylaniliniumtetra(phenyl)borate, N,N-dimethylaniliniumtetrakis(pentafluorophenyl)borate, N,N-di(propyl)ammoniumtetrakis(pentafluorophenyl)borate, di(cyclohexyl)ammoniumtetrakist(pentafluorophenyl)borate, triphenylphosphoniumtetrakis(phenyl)borate, triethylphosphoniumtetrakis(phenyl)borate, diphenylphosphoniumtetrakis(phenyl)borate, tri(methylphenyl) phosphoniumtetrakis(phenyl)borate, tri(dimethylphenyl) phosphoniumtetrakis(phenyl)borate, triphenylcarbeniumtetrakis(pentafluorophenyl)borate, or ferroceniumtetrakis(pentafluorophenyl)borate. Preference is given to triphenylcarbeniumtetrakis(pentafluorophenyl)borate, N,N-dimethylcyclohexylammoniumtetrakis(pentafluorophenyl)borate or N5N-dimethylbenzylammoniumtetrakis (pentafluorophenyl)borate.

The use of $B(C_6F_5)_3$, $C_6H_5N(CH_3)_2H:B(C_6F_5)_4$, $(C_6H_5)_3C:B(C_6F_5)_4$ or $Ni(CN)_4[B(C_6F_5)_3]_4{}^{2-}$ is especially preferred.

Suitable amounts of borate cocatalyst will be well known to the skilled man.

The use of aluminoxanes, especially MAO, is highly preferred.

Suitable amounts of aluminoxane cocatalyst will be well known to the skilled man. Typically Al to M molar ratios are from 1:1 to 1000:1 mol/mol. Preferably when an aluminium alkyl is used as a coctalyst, the molar ratio of the aluminium in the activator to the transition metal in the complex is from 1 to 500 mol/mol, preferably from 10 to 400 mol/mol and in particular from 50 to 400 mol/mol.

Catalyst Manufacture

The metallocene complex of the present invention can be used in combination with a suitable cocatalyst as a catalyst for the polymerization of olefins, e.g. in a solvent such as toluene or an aliphatic hydrocarbon, (i.e. for polymerization in solution), as it is well known in the art. Preferably, polymerization of olefins, especially propylene, takes place in the condensed phase or in gas phase.

The catalyst of the invention can be used in supported or unsupported form. It is possible therefore to use a supported catalyst, as is well known in the art. The particulate support material used is preferably an organic or inorganic material, such as silica, alumina or zirconia or a mixed oxide such as silica-alumina, in particular silica, alumina or silica-alumina. The use of a silica support is preferred. The skilled man is aware of the procedures required to support a metallocene catalyst.

Especially preferably the support is a porous material so that the complex may be loaded into the pores of the support, e.g. using a process analogous to those described in WO94/14856 (Mobil), WO95/12622 (Borealis) and WO2006/097497. The particle size is not critical but is preferably in the range 5 to 200 μm, more preferably 20 to 80 μm. The use of these supports is routine in the art.

In a preferred embodiment, no support is used at all. Preferably however, the catalyst is still provided in solid particulate form. Such a catalyst can be prepared in solution, for example in an aromatic solvent like toluene, by contacting the metallocene (as a solid or as a solution) with the cocatalyst, for example methylaluminoxane or a borane or a borate salt previously dissolved in an aromatic solvent, or can be prepared by sequentially adding the dissolved catalyst components to the polymerization medium. In a preferred embodiment, the metallocene (when X differs from alkyl or hydrogen) is prereacted with an aluminum alkyl, in a ratio metal/aluminum of from 1:1 up to 1:500, preferably from 1:1 up to 1:250, and then combined with a solution of the borane or borate cocatalyst dissolved in an aromatic solvent, either in a separate vessel or directly into the polymerization reactor. Preferred metal/boron ratios are between 1:1 and 1:100, more preferably 1:1 to 1:10.

In one particular embodiment, no external carrier is used but the catalyst is still presented in solid particulate form. Thus, no external support material such as inert organic or inorganic carrier, such as for example silica as described above is employed.

In order to provide the catalyst of the invention in solid form but without using an external carrier, it is preferred if a liquid/liquid emulsion system is used. The process involves forming dispersing catalyst components (i) and (ii) in a solvent, and solidifying said dispersed droplets to form solid particles.

In particular, the method involves preparing a solution of one or more catalyst components; dispersing said solution in an solvent to form an emulsion in which said one or more catalyst components are present in the droplets of the dispersed phase; immobilising the catalyst components in the dispersed droplets, in the absence of an external particulate porous support, to form solid particles comprising the said catalyst, and optionally recovering said particles.

This process enables the manufacture of active catalyst particles with improved morphology, e.g. with a predetermined spherical shape, surface properties and particle size and without using any added external porous support material, such as an inorganic oxide, e.g. silica. By the term "preparing a solution of one or more catalyst components" is meant that the catalyst forming compounds may be combined in one solution which is dispersed to the immiscible solvent, or, alternatively, at least two separate catalyst solutions for each part of the catalyst forming compounds may be prepared, which are then dispersed successively to the solvent.

In a preferred method for forming the catalyst at least two separate solutions for each or part of said catalyst may be prepared, which are then dispersed successively to the immiscible solvent.

More preferably, a solution of the complex comprising the transition metal compound and the cocatalyst is combined with the solvent to form an emulsion wherein that inert solvent forms the continuous liquid phase and the solution comprising the catalyst components forms the dispersed phase (discontinuous phase) in the form of dispersed droplets. The droplets are then solidified to form solid catalyst particles, and the solid particles are separated from the liquid and optionally washed and/or dried. The solvent forming the continuous phase may be immiscible to the catalyst solution at least at the conditions (e. g. temperatures) used during the dispersing step.

The term "immiscible with the catalyst solution" means that the solvent (continuous phase) is fully immiscible or partly immiscible i.e. not fully miscible with the dispersed phase solution.

Preferably said solvent is inert in relation to the compounds of the catalyst system to be produced. Full disclosure of the necessary process can be found in WO03/051934 which is herein incorporated by reference.

The inert solvent must be chemically inert at least at the conditions (e.g. temperature) used during the dispersing step. Preferably, the solvent of said continuous phase does not contain dissolved therein any significant amounts of catalyst forming compounds. Thus, the solid particles of the catalyst are formed in the droplets from the compounds which originate from the dispersed phase (i.e. are provided to the emulsion in a solution dispersed into the continuous phase).

The terms "immobilisation" and "solidification" are used herein interchangeably for the same purpose, i.e. for forming free flowing solid catalyst particles in the absence of an external porous particulate carrier, such as silica. The solidification happens thus within the droplets. Said step can be effected in various ways as disclosed in said WO03/051934 Preferably solidification is caused by an external stimulus to the emulsion system such as a temperature change to cause the solidification. Thus in said step the catalyst component (s) remain "fixed" within the formed solid particles. It is also possible that one or more of the catalyst components may take part in the solidification/immobilisation reaction.

Accordingly, solid, compositionally uniform particles having a predetermined particle size range can be obtained.

Furthermore, the particle size of the catalyst particles of the invention can be controlled by the size of the droplets in the solution, and spherical particles with a uniform particle size distribution can be obtained.

The invention is also industrially advantageous, since it enables the preparation of the solid particles to be carried out as a one-pot procedure. Continuous or semicontinuous processes are also possible for producing the catalyst.

Dispersed Phase

The principles for preparing two phase emulsion systems are known in the chemical field. Thus, in order to form the two phase liquid system, the solution of the catalyst component (s) and the solvent used as the continuous liquid phase have to be essentially immiscible at least during the dispersing step. This can be achieved in a known manner e.g. by choosing said two liquids and/or the temperature of the dispersing step/solidifying step accordingly.

A solvent may be employed to form the solution of the catalyst component (s). Said solvent is chosen so that it dissolves said catalyst component (s). The solvent can be preferably an organic solvent such as used in the field, comprising an optionally substituted hydrocarbon such as linear or branched aliphatic, alicyclic or aromatic hydrocarbon, such as a linear or cyclic alkane, an aromatic hydrocarbon and/or a halogen containing hydrocarbon.

Examples of aromatic hydrocarbons are toluene, benzene, ethylbenzene, propylbenzene, butylbenzene and xylene. Toluene is a preferred solvent. The solution may comprise one or more solvents. Such a solvent can thus be used to facilitate the emulsion formation, and usually does not form part of the solidified particles, but e.g. is removed after the solidification step together with the continuous phase.

Alternatively, a solvent may take part in the solidification, e.g. an inert hydrocarbon having a high melting point (waxes), such as above 40° C., suitably above 70° C., e. g. above 80° C. or 90° C., may be used as solvents of the dispersed phase to immobilise the catalyst compounds within the formed droplets.

In another embodiment, the solvent consists partly or completely of a liquid monomer, e.g. liquid olefin monomer designed to be polymerised in a "prepolymerisation" immobilisation step.

Continuous Phase

The solvent used to form the continuous liquid phase is a single solvent or a mixture of different solvents and may be immiscible with the solution of the catalyst components at least at the conditions (e.g. temperatures) used during the dispersing step. Preferably said solvent is inert in relation to said compounds.

The term "inert in relation to said compounds" means herein that the solvent of the continuous phase is chemically inert, i.e. undergoes no chemical reaction with any catalyst forming component. Thus, the solid particles of the catalyst are formed in the droplets from the compounds which originate from the dispersed phase, i.e. are provided to the emulsion in a solution dispersed into the continuous phase.

It is preferred that the catalyst components used for forming the solid catalyst will not be soluble in the solvent of the continuous liquid phase. Preferably, said catalyst components are essentially insoluble in said continuous phase forming solvent.

Solidification takes place essentially after the droplets are formed, i.e. the solidification is effected within the droplets e.g. by causing a solidifying reaction among the compounds present in the droplets. Furthermore, even if some solidifying agent is added to the system separately, it reacts within the droplet phase and no catalyst forming components go into the continuous phase.

The term "emulsion" used herein covers both bi- and multiphasic systems.

In a preferred embodiment said solvent forming the continuous phase is an inert solvent including a halogenated organic solvent or mixtures thereof, preferably fluorinated organic solvents and particularly semi, highly or perfluorinated organic solvents and functionalised derivatives thereof. Examples of the above-mentioned solvents are semi, highly or perfluorinated hydrocarbons, such as alkanes, alkenes and cycloalkanes, ethers, e.g. perfluorinated ethers and amines, particularly tertiary amines, and functionalised derivatives thereof. Preferred are semi, highly or perfluorinated, particularly perfluorinated hydrocarbons, e.g. perfluorohydrocarbons of e.g. C3-C30, such as C4-C10. Specific examples of suitable perfluoroalkanes and perfluorocycloalkanes include perfluoro-hexane, -heptane, -octane and -(methylcyclohexane). Semi fluorinated hydrocarbons relates particularly to semifluorinated n-alkanes, such as perfluoroalkyl-alkane.

"Semi fluorinated" hydrocarbons also include such hydrocarbons wherein blocks of —C—F and —C—H alternate. "Highly fluorinated" means that the majority of the —C—H units are replaced with —C—F units. "Perfluorinated" means that all —C—H units are replaced with —C—F units. See the articles of A. Enders and G. Maas in "Chemie in unserer Zeit", 34. Jahrg. 2000, Nr. 6, and of Pierandrea Lo Nostro in "Advances in Colloid and Interface Science", 56 (1995) 245-287, Elsevier Science.

Dispersing Step

The emulsion can be formed by any means known in the art: by mixing, such as by stirring said solution vigorously to said solvent forming the continuous phase or by means of mixing mills, or by means of ultra sonic wave, or by using a so called phase change method for preparing the emulsion by first forming a homogeneous system which is then transferred by changing the temperature of the system to a biphasic system so that droplets will be formed.

The two phase state is maintained during the emulsion formation step and the solidification step, as, for example, by appropriate stirring.

Additionally, emulsifying agents/emulsion stabilisers can be used, preferably in a manner known in the art, for facilitating the formation and/or stability of the emulsion. For the said purposes e.g. surfactants, e.g. a class based on hydrocarbons (including polymeric hydrocarbons with a molecular weight e.g. up to 10 000 and optionally interrupted with a heteroatom(s)), preferably halogenated hydrocarbons, such as semi- or highly fluorinated hydrocarbons optionally having a functional group selected e.g. from —OH, —SH, NH$_2$, NR"$_2$. —COOH, —COONH$_2$, oxides of alkenes, —CR"=CH$_2$, where R" is hydrogen, or C1-C20 alkyl, C2-20-alkenyl or C2-20-alkynyl group, oxo-groups, cyclic ethers and/or any reactive derivative of these groups, like alkoxy, or carboxylic acid alkyl ester groups, or, preferably semi-, highly- or perfluorinated hydrocarbons having a functionalised terminal, can be used. The surfactants can be added to the catalyst solution, which forms the dispersed phase of the emulsion, to facilitate the forming of the emulsion and to stabilize the emulsion.

Alternatively, an emulsifying and/or emulsion stabilising aid can also be formed by reacting a surfactant precursor bearing at least one functional group with a compound reactive with said functional group and present in the catalyst solution or in the solvent forming the continuous phase. The obtained reaction product acts as the actual emulsifying aid and or stabiliser in the formed emulsion system.

Examples of the surfactant precursors usable for forming said reaction product include e.g. known surfactants which bear at least one functional group selected e.g. from —OH, —SH, NH$_2$, NR"$_2$. —COOH, —COONH$_2$, oxides of alkenes, —CR"=CH$_2$, where R" is hydrogen, or C1-C20 alkyl, C2-20-alkenyl or C2-20-alkynyl group, oxo-groups, cyclic ethers with 3 to 5 ring atoms, and/or any reactive derivative of these groups, like alkoxy or carboxylic acid alkyl ester groups; e.g. semi-, highly or perfluorinated hydrocarbons bearing one or more of said functional groups. Preferably, the surfactant precursor has a terminal functionality as defined above.

The compound reacting with such surfactant precursor is preferably contained in the catalyst solution and may be a further additive or one or more of the catalyst forming compounds. Such compound is e.g. a compound of group 13 (e.g. MAO and/or an aluminium alkyl compound and/or a transition metal compound).

If a surfactant precursor is used, it is preferably first reacted with a compound of the catalyst solution before the addition of the transition metal compound. In one embodiment e.g. a highly fluorinated C1-n (suitably C4-30- or C5-15) alcohol (e.g. highly fluorinated heptanol, octanol or nonanol), oxide (e.g. propenoxide) or acrylate ester is reacted with a cocatalyst to form the "actual" surfactant. Then, an additional amount of cocatalyst and the transition metal compound is added to said solution and the obtained solution is dispersed to the solvent forming the continuous phase. The "actual" surfactant solution may be prepared before the dispersing step or in the dispersed system. If said solution is made before the dispersing step, then the prepared "actual" surfactant solution and the transition metal solution may be dispersed successively (e. g. the surfactant solution first) to the immiscible solvent, or be combined together before the dispersing step.

Solidification

The solidification of the catalyst component(s) in the dispersed droplets can be effected in various ways, e.g. by causing or accelerating the formation of said solid catalyst forming reaction products of the compounds present in the droplets. This can be effected, depending on the used compounds and/or the desired solidification rate, with or without an external stimulus, such as a temperature change of the system.

In a particularly preferred embodiment, the solidification is effected after the emulsion system is formed by subjecting the system to an external stimulus, such as a temperature change. Temperature differences of e.g. 5 to 100° C., such as 10 to 100° C., or 20 to 90° C., such as 50 to 90° C. can be used.

The emulsion system may be subjected to a rapid temperature change to cause a fast solidification in the dispersed system. The dispersed phase may e. g. be subjected to an immediate (within milliseconds to few seconds) temperature change in order to achieve an instant solidification of the component (s) within the droplets. The appropriate temperature change, i. e. an increase or a decrease in the temperature of an emulsion system, required for the desired solidification rate of the components cannot be limited to any specific range, but naturally depends on the emulsion system, i. a. on the used compounds and the concentrations/ratios thereof, as well as on the used solvents, and is chosen accordingly. It is also evident that any techniques may be used to provide sufficient heating or cooling effect to the dispersed system to cause the desired solidification.

In one embodiment the heating or cooling effect is obtained by bringing the emulsion system with a certain temperature to an inert receiving medium with significantly different temperature, e. g. as stated above, whereby said temperature change of the emulsion system is sufficient to cause the rapid solidification of the droplets. The receiving medium can be gaseous, e. g. air, or a liquid, preferably a solvent, or a mixture of two or more solvents, wherein the catalyst component (s) is (are) immiscible and which is inert in relation to the catalyst component (s). For instance, the receiving medium comprises the same immiscible solvent used as the continuous phase in the first emulsion formation step.

Said solvents can be used alone or as a mixture with other solvents, such as aliphatic or aromatic hydrocarbons, such as alkanes. Preferably a fluorinated solvent as the receiving medium is used, which may be the same as the continuous phase in the emulsion formation, e. g. perfluorinated hydrocarbon.

Alternatively, the temperature difference may be effected by gradual heating of the emulsion system, e. g. up to 10° C. per minute, preferably 0.5 to 6° C. per minute and more preferably in 1 to 5° C. per minute.

In case a melt of e. g. a hydrocarbon solvent is used for forming the dispersed phase, the solidification of the droplets may be effected by cooling the system using the temperature difference stated above.

Preferably, the "one phase" change as usable for forming an emulsion can also be utilised for solidifying the catalytically active contents within the droplets of an emulsion system by, again, effecting a temperature change in the dispersed system, whereby the solvent used in the droplets becomes miscible with the continuous phase, preferably a fluorous continuous phase as defined above, so that the droplets become impoverished of the solvent and the solidifying components remaining in the "droplets" start to solidify. Thus the immisciblity can be adjusted with respect to the solvents and conditions (temperature) to control the solidification step.

The miscibility of e.g. organic solvents with fluorous solvents can be found from the literature and be chosen accordingly by a skilled person. Also the critical temperatures needed for the phase change are available from the literature or can be determined using methods known in the art, e. g. the Hildebrand-Scatchard-Theorie. Reference is also made to the articles of A. Enders and G. and of Pierandrea Lo Nostro cited above.

Thus according to the invention, the entire or only part of the droplet may be converted to a solid form. The size of the "solidified" droplet may be smaller or greater than that of the original droplet, e. g. if the amount of the monomer used for the prepolymerisation is relatively large.

The solid catalyst particles recovered can be used, after an optional washing step, in a polymerisation process of an olefin. Alternatively, the separated and optionally washed solid particles can be dried to remove any solvent present in the particles before use in the polymerisation step. The separation and optional washing steps can be effected in a known manner, e. g. by filtration and subsequent washing of the solids with a suitable solvent.

The droplet shape of the particles may be substantially maintained. The formed particles may have a mean size range of 1 to 500 μm, e.g. 5 to 500 μm, advantageously 5 to 200 μm or 10 to 150 μm. Even a mean size range of 5 to 60 μm is possible. The size may be chosen depending on the polymerisation the catalyst is used for. Advantageously, the mean particle size of the ready particulate catalysts of the invention are in the range of 2 to 150 μm, preferably 5 to 120 μm, more preferably 5 to 90 μm and especially in the range 10 to 70 μm. The particles are essentially spherical in shape, they have a low porosity and a low surface area.

The formation of solution can be effected at a temperature of 0-100° C., e.g. at 20-80° C. The dispersion step may be effected at −20° C.-100° C., e.g. at about −10-70° C., such as at −5 to 30° C., e.g. around 0° C.

To the obtained dispersion an emulsifying agent as defined above, may be added to improve/stabilise the droplet formation. The solidification of the catalyst component in the droplets is preferably effected by raising the temperature of the mixture, e.g. from 0° C. temperature up to 100° C., e.g. up to 60-90° C., gradually. E.g. in 1 to 180 minutes, e.g. 1-90 or 5-30 minutes, or as a rapid heat change. Heating time is dependent on the size of the reactor.

During the solidification step, which is preferably carried out at about 60 to 100° C., preferably at about 75 to 95° C., (below the boiling point of the solvents) the solvents may preferably be removed and optionally the solids are washed with a wash solution, which can be any solvent or mixture of solvents such as those defined above and/or used in the art, preferably a hydrocarbon, such as pentane, hexane or heptane, suitably heptane. The washed catalyst can be dried or it can be slurried into an oil and used as a catalyst-oil slurry in polymerisation process.

All or part of the preparation steps can be done in a continuous manner. Reference is made to WO2006/069733 describing principles of such a continuous or semicontinuous preparation methods of the solid catalyst types, prepared via emulsion/solidification method.

Polymerisation

The olefin polymerized using the catalyst of the invention is preferably propylene or a higher alpha-olefin or a mixture of ethylene and an α-olefin or a mixture of alpha olefins, for example $C_{2-20}$ olefins, e.g. ethylene, propylene, 1-butene, 1-hexene, 4-methyl-1-pentene, 1-octene etc. The olefins polymerized in the method of the invention may include any compound which includes unsaturated polymerizable groups. Thus, for example unsaturated compounds, such as $C_{6-20}$ olefins (including cyclic and polycyclic olefins (e.g. norbornene)), and polyenes, especially $C_{4-20}$ dienes, may be included in a comonomer mixture with lower olefins, e.g. $C_{2-5}$ α-olefins. Diolefins (i.e. dienes) are suitably used for introducing long chain branching into the resultant polymer. Examples of such dienes include α,ω linear dienes such as 1,5-hexadiene, 1,6-heptadiene, 1,8-nonadiene, 1,9-decadiene, etc.

The catalysts of the present invention are particularly suited for use in the manufacture of polypropylene polymers, especially isotactic polypropylene, random propylene copolymers and heterophasic propylene copolymers.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase reactors.

In case of propylene polymerisation for slurry reactors, the reaction temperature will generally be in the range 60 to 110° C. (e.g. 60-90° C.), the reactor pressure will generally be in the range 5 to 80 bar (e.g. 20-60 bar), and the residence time will generally be in the range 0.1 to 5 hours (e.g. 0.3 to 2 hours). The monomer is usually used as reaction medium.

For gas phase reactors, the reaction temperature used will generally be in the range 60 to 115° C. (e.g. 70 to 110° C.), the reactor pressure will generally be in the range 10 to 25 bar, and the residence time will generally be 0.5 to 8 hours (e.g. 0.5 to 4 hours) The gas used will be the monomer optionally as mixture with a non-reactive gas such as nitrogen or propane. In addition to actual polymerisation steps and reactors, the process can contain any additional polymerisation steps, like prepolymerisation step, and any further after reactor handling steps as known in the art.

Generally the quantity of catalyst used will depend upon the nature of the catalyst, the reactor types and conditions and the properties desired for the polymer product. As is well known in the art hydrogen can be used for controlling the molecular weight of the polymer. It is particularly notable that the catalyst of the present invention performs exceptionally well over a wide range of hydrogen concentration used during the polymerisation process, which makes the catalyst beneficial to be used for productions of a wide range of polymers The catalysts are useful at higher hydrogen concentrations as well with lower hydrogen concentrations to get polymer with higher molecular weight. The activity of the catalysts of the invention is also very high and the polymer productivity levels are excellent.

It is a feature of the invention that the claimed catalysts enable the formation of polymers with remarkably high melting points and with remarkably high molecular weight. These features can be achieved at commercially interesting polymerisation temperatures, e.g. 60° C. or more. It is a preferred feature of the invention that the catalysts of the invention are used to polymerise propylene at a temperature of at least 60° C., preferably at least 65° C., such as at least 70° C.

Catalyst activities of the order of 10.0 kg/g(cat)/h or more, such as 12 kg/g(cat)/h or more have been achieved on laboratory scale for homopolymerisation as disclosed in the examples and more than 25 kg/g(cat)/h (such as up to 70 kg/g(cat)/h) for random copolymers as disclosed in the examples.

The propylene polymers made using the catalysts of the invention may have high molecular weight. If the polymer is a propylene homopolymer, they may also be highly isotactic. Isotacticity is measured by 13C NMR or also by DSC. Thus, in the case of polypropylene homopolymers, isotacticity can be higher than 99.5% mm when measured by 13C NMR. When measured by standard DSC, the high isotacticity of the polypropylene homopolymers means a melting point (Tm) higher than 148° C.

The molecular weight of the polypropylene can be at least 200,000, preferably at least 300,000, especially at least 400,000. However, the molecular weight of the formed polymer is dependent on the amount of hydrogen employed, and in the case of propylene random copolymers, dependent on the amount of comonomer, as is well known in the art.

Polypropylenes made by the metallocenes of the invention can be made with $MFR_2$ values in the whole range of interest, that is from very high (as high as 2000, for example 1000 or 500) to very low, that is fractional values (<1). Hydrogen can be used to manipulate MFR as is well known.

In propylene random copolymers the amount comonomer (such as ethylene) is typically in the range of <1 wt-% to about 8 wt-%, like e.g. 1 wt-% to 6 wt-% (measured by FTIR)

Applications

The polymers made by the catalysts of the invention are useful in all kinds of end articles such as pipes, films (cast, blown and BOPP films), fibers, moulded articles (e.g. injection moulded, blow moulded, rotomoulded articles), extrusion coatings and so on. Film applications, such as those requiring BOPP (bi-oriented polyethylene) film, especially for capacitors are favoured.

The invention will now be illustrated by reference to the following non-limiting Examples.

Measurement Methods:

ICP Analysis

The elemental analysis of a catalyst was performed by taking a solid sample of mass, M, cooling over dry ice. Samples were diluted up to a known volume, V, by dissolving in nitric acid (HNO3, 65%, 5% of V) and freshly deionised (DI) water (5% of V). The solution was then added to hydrofluoric acid (HF, 40%, 3% of V), diluted with DI water up to the final volume, V, and left to stabilise for two hours.

The analysis was run at room temperature using a Thermo Elemental iCAP 6300 Inductively Coupled Plasma—Optical Emmision Spectrometer (ICP-OES) which was calibrated using a blank (a solution of 5% HNO3, 3% HF in DI water), and 6 standards of 0.5 ppm, 1 ppm, 10 ppm, 50 ppm, 100 ppm and 300 ppm of Al, with 0.5 ppm, 1 ppm, 5 ppm, 20 ppm, 50 ppm and 100 ppm of Hf and Zr in solutions of 5% HNO3, 3% HF in DI water.

Immediately before analysis the calibration is 'resloped' using the blank and 100 ppm Al, 50 ppm Hf, Zr standard, a quality control sample (20 ppm Al, 5 ppm Hf, Zr in a solution of 5% HNO3, 3% HF in DI water) is run to confirm the reslope. The QC sample is also run after every 5th sample and at the end of a scheduled analysis set.

The content of hafnium was monitored using the 282.022 nm and 339.980 nm lines and the content for zirconium using 339.198 nm line. The content of aluminium was monitored via the 167.079 nm line, when Al concentration in ICP sample was between 0-10 ppm (calibrated only to 100 ppm) and via the 396.152 nm line for Al concentrations above 10 ppm.

The reported values are an average of three successive aliquots taken from the same sample and are related back to the original catalyst by inputting the original mass of sample and the dilution volume into the software.

DSC Analysis

Melting temperature $T_m$ and crystallization temperature $T_c$ were measured on approx. 5 mg samples with a Mettler-Toledo 822e differential scanning calorimeter (DSC), according to ISO11357-3 in a heat/cool/heat cycle with a scan rate of 10° C./min in the temperature range of +23 to +225° C. under a nitrogen flow rate of 50 ml min$^{-1}$. Melting and crystallization temperatures were taken as the endotherm and exotherm peaks, respectively in the second heating and in the cooling step.

Calibration of the instrument was performed with $H_2O$, Lead, Tin, Indium, according to ISO 11357-1. The maximum error in temperature from calibration was less than 0.3° C.

Melt Flow Rate

The melt flow rate (MFR) is determined according to ISO 1133 and is indicated in g/10 min. The MFR is an indication of the flowability, and hence the processability, of the polymer. The higher the melt flow rate, the lower the viscosity of the polymer. The MFR is determined at 230° C. and may be determined at different loadings such as 2.16 kg ($MFR_2$) or 21.6 kg ($MFR_{21}$).

GPC: Molecular Weight Averages, Molecular Weight Distribution, and Polydispersity Index ($M_n$, $M_w$, $M_w/M_n$)

Molecular weight averages (Mw, Mn), Molecular weight distribution (MWD) and its broadness, described by polydispersity index, PDI=Mw/Mn (wherein Mn is the number average molecular weight and Mw is the weight average molecular weight) were determined by Gel Permeation Chromatography (GPC) according to ISO 16014-4:2003 and ASTM D 6474-99. A Waters GPCV2000 instrument, equipped with differential refractive index detector and online viscosimeter was used with 2×GMHXL-HT and 1× G7000HXL-HT TSK-gel columns from Tosoh Bioscience and 1,2,4-trichlorobenzene (TCB, stabilized with 250 mg/L 2,6-Di tert butyl-4-methyl-phenol) as solvent at 140° C. and at a constant flow rate of 1 mL/min. 209.5 µL of sample solution were injected per analysis. The column set was calibrated using universal calibration (according to ISO 16014-2:2003) with at least 15 narrow MWD polystyrene (PS) standards in the range of 1 kg/mol to 12 000 kg/mol. Mark Houwink constants for PS, PE and PP used are as per ASTM D 6474-99. All samples were prepared by dissolving 0.5-4.0 mg of polymer in 4 mL (at 140° C.) of stabilized TCB (same as mobile phase) and keeping for max. 3 hours at max. 160° C. with continuous gentle shaking prior sampling into the GPC instrument.

Catalyst Activity

The catalyst activity was calculated on the basis of following formula:

$$\text{Catalyst Activity(kg/(g(cat)} * \text{h))} = \frac{\text{amount of polymer produced(kg)}}{\text{catalyst loading(g)} \times \text{polymerisation time(h)}}$$

Quantification of Polypropylene Homopolymer Microstructure by NMR Spectroscopy

Quantitative nuclear-magnetic resonance (NMR) spectroscopy was used to quantify the isotacticity and content of regio-defects of the polypropylene homopolymers. Quantitative $^{13}C$ $\{^1H\}$ NMR spectra recorded in the solution-state using a Bruker Advance III 400 NMR spectrometer operating at 400.15 and 100.62 MHz for $^1H$ and $^{13}C$ respectively. All spectra were recorded using a $^{13}C$ optimised 10 mm selective excitation probehead at 125° C. using nitrogen gas for all pneumatics. Approximately 200 mg of material was dissolved in 1,2-tetrachloroethane-$d_2$ (TCE-$d_2$). This setup was chosen primarily for the high resolution needed for tacticity distribution quantification (Busico, V., Cipullo, R., Prog. Polym. Sci. 26 (2001) 443; Busico, V.; Cipullo, R., Monaco, G., Vacatello, M., Segre, A. L., Macromolecules 30 (1997) 6251). Standard single-pulse excitation was employed utilising the NOE and bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico, G., Macromol. Rapid Commun. 2007, 28, 11289). A total of 8192 (8 k) transients were acquired per spectra. Quantitative $^{13}C$ $\{^1H\}$ NMR spectra were processed, integrated and relevant quantitative properties determined from the integrals using proprietary computer programs. All chemical shifts are internally referenced to the methyl signal of the isotactic pentad mmmm at 21.85 ppm.

The tacticity distribution was quantified through integration of the methyl region between 23.6 and 19.7 ppm correcting for any sites not related to the stereo sequences of interest (Busico, V., Cipullo, R., Prog. Polym. Sci. 26 (2001) 443; Busico, V., Cipullo, R., Monaco, G., Vacatello, M., Segre, A. L., Macromolecules 30 (1997) 6251). The pentad isotacticity was determined through direct integration of the methyl region and reported as either the mole fraction or percentage of isotactic pentad mmmm with respect to all steric pentads i.e. [mmmm]=mmmm/sum of all steric pentads. When appropriate integrals were corrected for the presence of sites not directly associated with steric pentads.

Characteristic signals corresponding to regio irregular propene insertion were observed (Resconi, L., Cavallo, L., Fait, A., Piemontesi, F., Chem. Rev. 2000, 100, 1253). The presence of secondary inserted propene in the form of 2,1 erythro regio defects was indicated by the presence of the two methyl signals at 17.7 and 17.2 ppm and confirmed by the presence of other characteristic signals. The amount of 2,1 erythro regio defects was quantified using the average integral (e) of the e6 and e8 sites observed at 17.7 and 17.2 ppm respectively, i.e. e=0.5*(e6+e8). Characteristic signals corresponding to other types of regio irregularity were not observed (Resconi, L., Cavallo, L., Fait, A., Piemontesi, F., Chem. Rev. 2000, 100, 1253). The amount of primary inserted propene (p) was quantified based on the integral of all signals in the methyl region (CH3) from 23.6 to 19.7 ppm paying attention to correct for other species included in the integral not related to primary insertion and for primary insertion signals excluded from this region such that p=CH3+2*e. The relative content of a specific type of regio defect was reported as the mole fraction or percentage of said regio defect with respect all observed forms of propene insertion i.e. sum of all primary (1,2), secondary (2,1) and tertiary (3,1) inserted propene units, e.g. [21e]=e/(p+e+t+i). The total amount of secondary inserted propene in the form of 2,1-erythro or 2,1-threo regio defects was quantified as sum of all said regio irregular units, i.e. [21]=[21e]+[21t].

Quantification of Copolymer Microstructure by NMR Spectroscopy

Quantitative nuclear-magnetic resonance (NMR) spectroscopy was used to quantify the comonomer content and comonomer distribution of the copolymers, specifically propene-co-ethylene copolymers. Quantitative $^{13}C$ $\{^1H\}$ NMR spectra recorded in the solution-state using a Bruker Advance III 400 NMR spectrometer operating at 400.15 and 100.62 MHz for $^1H$ and $^{13}C$ respectively. All spectra were recorded using a $^{13}C$ optimised 10 mm selective excitation probehead at 125° C. using nitrogen gas for all pneumatics. Approximately 200 mg of material was dissolved in 1,2-tetrachloroethane-$d_2$ (TCE-$d_2$) with chromium-(III)-acetylacetonate (Cr(acac)$_3$) resulting in a 65 mM solution of relaxation agent in solvent (Singh, G., Kothari, A., Gupta, V., Polymer Testing 28 5 (2009), 475). This setup was chosen primarily for the high resolution and quantitative spectra needed for accurate ethylene content determination. Standard single-pulse excitation was employed without NOE, using an optimised tip angle, 1 s recycle delay and bi-level WALTZ16 decoupling scheme (Zhou, Z., Kuemmerle, R., Qiu, X., Redwine, D., Cong, R., Taha, A., Baugh, D. Winniford, B., J. Mag. Reson. 187 (2007) 225; Busico, V., Carbonniere, P., Cipullo, R., Pellecchia, R., Severn, J., Talarico, G., Macromol. Rapid Commun. 2007, 28, 11289). A total of 6144 (6 k) transients were acquired per spectra. Quantitative $^{13}C$ $\{^1H\}$ NMR spectra were processed, integrated and relevant quantitative properties determined from the integrals using proprietary computer programs. All chemical shifts were indirectly referenced to the central methylene group of the ethylene block (EEE) at 30.00 ppm using the chemical shift of the solvent. This approach allowed comparable referencing even when this structural unit was not present.

Characteristic signals corresponding to regio irregular propene insertion were observed (Resconi, L., Cavallo, L., Fait, A., Piemontesi, F., Chem. Rev. 2000, 100, 1253).].

Characteristic signals corresponding to the incorporation of ethylene were observed (Cheng, H. N., Macromolecules 17, 1984, 1950). The comonomer content was calculated as the mole fraction or percent of incorporated ethylene with respect to all monomer in the copolymer using the method of Wang et. al. (Wang, W.-J., Zhu, S., Macromolecules 33, 2000, 1157) through integration of multiple signals spanning the whole spectral $^{13}C$ spectra. This analyse method was chosen for its robust nature and ability to account for the presence of regio irregular propene insertion when needed. Integral regions were slightly adjusted to increase applicability across the whole range of encountered comonomer contents.

For systems where only isolated ethylene incorporation (PPEPP) was observed the method of Wang et. al. was modified to reduce the influence of non-zero integrals used to quantify higher order comonomer sequences. In such cases the term for the absolute ethylene content was determined based upon only E=0.5(S$\beta\beta$+S$\beta\gamma$+S$\beta\delta$+0.5(S$\alpha\beta$+S$\alpha\gamma$))) or E=0.5($I_H$+$I_G$+0.5($I_C$+$I_D$)) using the same notation as Wang et. al. (Wang, W.-J., Zhu, S., Macromolecules 33, 2000, 1157). The term used for absolute propylene content (P) was not modified and the mole fraction of ethylene calculated as [E]=E/(E+P). The comonomer content in weight percent was calculated from the mole fraction in the usual way i.e. [E wt %]=100*([E]*28.06)/ ((([E]*28.06)+((1−[E])*42.08)).

Ethylene Content from PP (FTIR $C_2$)

Ethylene content was measured with Fourier transform infrared spectroscopy (FTIR) calibrated to results obtained by $^{13}C$ NMR spectroscopy using a method which accounts for regio-irregular propene insertion. When measuring the ethylene content in polypropylene, a thin film of the sample (thickness about 0.220 to 0.250 mm) was prepared by hotpressing at 230° C. (preheat 5 min., press 1 min., cooling (cold water) 5 min.) using a Graseby Specac press. The FTIR spectra of the sample was recorded immediately with Nicolet Protégé 460 spectrometer from 4000 to 400 cm$^{-1}$, resolution 4 cm$^{-1}$, scans 64. The area of absorption peak at 733 cm$^{-1}$ (baseline from 700 cm$^{-1}$ to 760 cm$^{-1}$) and height of reference peak at 809 cm$^{-1}$ (baseline from 780 cm$^{-1}$ to 880 cm$^{-1}$) were evaluated. The result was calculated using the following formula $$E_{tot} = a \times A/R + b$$

where

A=area of absorption peak at 733 cm$^{-1}$

R=height of reference peak at 809 cm$^{-1}$ $E_{tot}$=C2 content (wt.-%)

a, b are calibration constants determined by correlation of multiple calibration standards of know ethylene content as determined by $^{13}C$ NMR spectroscopy to A/R.

The result was reported as an average of two measurements.

EXAMPLES

Chemicals

All the chemicals and chemical reactions were handled under an inert gas atmosphere using Schlenk and glovebox techniques, with oven-dried glassware, syringes, needles or cannulas.

MAO was purchased from Albermarle and used as a 30 wt-% solution in toluene.

The mixture of perfluoroalkylethyl acrylate esters (CAS 65605-70-1) used as the surfactant was purchased from the Cytonix corporation, dried over activated molecular sieves (2 times) and degassed by argon bubbling prior to use.

Perfluoro-1,3-dimethylcyclohexane (PFC, CAS 335-27-3) was dried over activated molecular sieves (2 times) and degassed by argon bubbling prior to use.

Triethylaluminum was purchased from Crompton and used in pure form. Hydrogen is provided by AGA and purified before use.

Propylene is provided by Borealis and adequately purified before use.

The following metallocene complexes are used in the comparative examples:

rac-dimethylsilanediylbis(2-methyl-4-phenylindenyl)zirconium dichloride, CAS no 153882-67-8 (CMCJ)

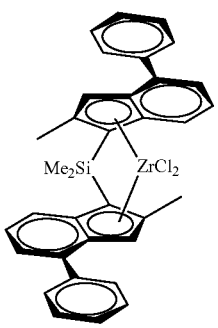

rac-Me$_2$Si[2-Me-4-(3,5-$^t$Bu$_2$Ph)Ind]$_2$ZrCl$_2$/MAO, (CMC2)

rac-Me$_2$Si[2-Me-4-(3,5-$^t$Bu$_2$Ph)-7-OMe-Ind]$_2$ZrCl$_2$/ MAO (CMC3)

Other Reagents:

2 M HCl, 12 M HCl (Reachim, Russia), silica gel 60 (40-63 um, Merck), K$_2$CO$_3$ (Merck), ZrCl$_4$(THF)$_2$ magnesium turnings (Acros), TsOH (Aldrich), nBuLi (Chemetall), n-hexane (Merck), were used as received. Toluene (Merck), THF (Merck), dichloromethane (Merck), were kept and distilled over Na/K alloy. Dichlorodimethylsilane (Merck) was distilled before use. CDCl$_3$, DMSO-d$_6$ and CD$_2$Cl$_2$ (Deutero GmbH) for NMR experiments were dried and kept over CaH$_2$. Methyl iodide is Acros. 1-bromo-3,5-di-tert-butylbenzene (Aldrich) has been used as received.

Bis(2,6-diisopropylphenyl)imidazolium chloride, i.e. IPr (HCl), and (IPr)NiCl$_2$(PPh$_3$) were synthesized as described in [Hintermann, L. Beilstein *J. Org. Chem.* 2007, 3, 1.] and [Matsubara, K.; Ueno, K.; Shibata, Y. *Organometallics* 2006, 25, 3422.], respectively.

4-Bromo-1-methoxy-2-methylindane was obtained as described in [Izmer, V. V.; Lebedev, A. Y.; Nikulin, M. V.; Ryabov, A. N.; Asachenko, A. F.; Lygin, A. V.; Sorokin, D. A.; Voskoboynikov, A. Z. *Organometallics* 2006, 25, 1217.].

Complex Synthesis MC1

1-Bromo-2-(bromomethyl)-4-methoxybenzene

Method 1

1-(Bromomethyl)-3-methoxybenzene

To a solution of 122 g (1.0 mol) of 1-methoxy-3-methylbenzene in 900 ml of CCl$_4$, 178 g (1.0 mol) of NBS and 1.0 g of (PhCO$_2$)$_2$ were added at room temperature. This mixture was refluxed for 3 h, cooled to room temperature, and the formed succinimide was filtered off. Succinimide was additionally washed by 2×150 ml of CCl$_4$. The combined filtrate was evaporated to dryness, and the residue was distilled in vacuum, b.p. 112-125° C./8 mm Hg. This procedure gave 152.5 g of 1-(bromomethyl)-3-methoxybenzene contaminated with ca. 25% of the isomeric product, i.e. 1-bromo-4-methoxy-2-methylbenzene.

Anal. calc. for C$_8$H$_9$BrO: C, 47.79; H, 4.51. Found: C, 47.93; H, 4.65.

$^1$H NMR (CDCl$_3$): δ 7.26 (m, 1H, 5-H), 6.98 (m, 1H, 6-H), 6.94 (m, 1H, 2-H), 6.85 (m, 1H, 4-H), 4.47 (s, 2H, CH$_2$Br), 3.81 (s, 3H, OMe).

1-Bromo-2-(bromomethyl)-4-methoxybenzene

To a solution of above-described crude 1-(bromomethyl)-3-methoxybenzene (152.5 g) in 1 L of chloroform a solution of 134 g (0.841 mol) of bromine in 200 ml of chloroform was added dropwise by vigorous stirring at room temperature. The reaction mixture was stirred overnight at ambient temperature and then evaporated to dryness. The residue was triturated with 1000 ml of n-hexane, and the precipitate was filtered off, washed with 100 ml of n-hexane, and then dried in vacuum. An additional amount of the product was obtained by evaporation of mother liquor followed by treatment of the residue with 200 ml of n-hexane. In total, this procedure gave 153 g (55% overall yield for two stages) of 1-bromo-2-(bromomethyl)-4-methoxybenzene. (average of two runs)

Anal. calc. for C$_8$H$_8$Br$_2$O: C, 34.32; H, 2.88. Found: C, 34.30; H, 3.01.

1H NMR (CDCl$_3$): δ 4.48 (d, J=8.8 Hz, 1H, 6-H), 7.02 (d, J=3.0 Hz, 1H, 3-H), 6.76 (dd, J=8.8 Hz, J=3.0 Hz, 1H, 5-H), 4.58 (s, 2H, CH2Br), 3.83 (s, 3H, OMe).

Method 2

1-Bromo-4-methoxy-2-methylbenzene

To a solution of 122 g (1.0 mol) of 1-methoxy-3-methylbenzene in 1 L of acetonitrile 178 g (1.0 mol) of NBS was added in small portions by vigorous stirring for 1 h at 10° C. The reaction mixture was stirred at ambient temperature overnight and then evaporated to dryness. The residue was dissolved in 1 L of n-hexane and filtered through glass frit (G2). The precipitate was additionally washed by 2×150 ml of n-hexane. The combined filtrate was evaporated to dryness to give 173 g (86%) of 1-bromo-4-methoxy-2-methylbenzene.

Anal. calc. for C$_8$H$_9$BrO: C, 47.79; H, 4.51. Found: C, 47.83; H, 4.69.

1H NMR (CDCl$_3$): δ 7.43 (d, J=8.8 Hz, 1H, 6-H), 6.82 (d, J=2.9 Hz, 1H, 3-H), 6.64 (dd, J=8.8 Hz, J=2.9 Hz, 1H, 5-H), 3.80 (s, 3H, OMe), 2.40 (s, 3-H, 2-Me).

1-Bromo-2-(bromomethyl)-4-methoxybenzene

To a solution of 173 g (0.86 mol) of 1-bromo-4-methoxy-2-methylbenzene in 850 ml of CCl$_4$ 153 g (0.86 mol) of NBS and 1.0 g of (PhCOO)$_2$ were added at room temperature. This mixture was refluxed for 16 h, cooled to room temperature, and then filtered through glass frit (G2). The precipitate was additionally washed by 2×150 ml of CCl$_4$. The combined filtrate was evaporated to dryness, and the residue was triturated with 600 ml of n-hexane. The precipitate was filtered off (G3 glass frit), washed by 50 ml of n-hexane, and dried in vacuum. This procedure gave 121 g of the title product. Additional amount of the product was obtained by evaporation of a mother liquor followed by crystallization of the residue from 200 ml of n-hexane at −25° C. In total, 157 g (65%; or 56% overall yield for two stages) of 1-bromo-2-(bromomethyl)-4-methoxybenzene has been isolated.

Anal. calc. for C$_8$H$_8$Br$_2$O: C, 34.32; H, 2.88. Found: C, 34.44; H, 2.95.

Method 3

1-Bromo-2-(bromomethyl)-4-methoxybenzene. N-Bromosuccinimide (45.9 g) was added to a solution of 15.1 g (123 mmol) of 3-methylanisole in 240 ml of tetrachloromethane. The mixture was refluxed for 14 h with 0.3 g of benzoyl peroxide. The resulting mixture was filtered through glass frit (G3), to the filtrate 100 ml of dichloromethane and 300 ml of cold water were added. The organic layer was separated, dried over Na$_2$SO$_4$, and then evaporated to dryness. The residue was recrystallized from hot hexanes to give 16.0 g of the title compound. The mother liquor was evaporated to dryness, and the residue was recrystallized from hexanes to give additional 6.1 g of the title material. Total yield 22.1 g (64%) of a white crystalline solid.

Anal. calc. for C$_8$H$_8$Br$_2$O: C, 34.32; H, 2.88. Found: C, 34.47; H, 3.02.

3-(2-Bromo-5-methoxyphenyl)-2-methylpropanoic acid

To a solution of sodium ethoxide obtained from 15.2 g (0.661 mol) of sodium and 540 ml of dry ethanol 115 g (0.658 mol) of diethyl methylmalonate was added. This mixture was stirred for 15 min; then, 184 g (0.659 mol) of 1-bromo-2-(bromomethyl)-4-methoxybenzene was added with vigorous stirring at such a rate to maintain gentle reflux. This mixture was refluxed for an additional 2 h and then cooled to room temperature. A solution of 130 g of KOH in 400 ml of water was added. The resulting mixture was refluxed for 4 h to saponificate the formed ester. Ethanol and water were distilled off until the vapor temperature reached 95° C. To the residue cooled to room temperature 1500 ml of water and then 12 M HCl (to pH 1) were added. The formed precipitate of (2-bromo-5-methoxybenzyl)(methyl)malonic acid was filtered off, washed with 2×200 ml of cold water, and dried on air. Decarboxylation of the substituted methylmalonic acid at 180° C. gave 152 g (84%) of the title product.

Anal. calc. for C$_{11}$H$_{13}$BrO$_3$: C, 48.37; H, 4.80. Found: C, 48.21; H, 4.92.

1H NMR (CDCl$_3$): δ 7.45 (d, J=8.8 Hz, 1H, 3-H in aryl), 6.82 (d, J=3.0 Hz, 1H, 6-H in aryl), 6.69 (dd, J=8.8 Hz, J=3.0 Hz, 1H, 4-H in aryl), 3.79 (s, 3H, OMe), 3.17 (dd, J=13.6 Hz, J=7.1 Hz, 1H, CHH'CH), 2.94 (m, 1H, CHMe), 2.82 (dd, J=13.6 Hz, J=7.5 Hz, 1H, CHH'CH), 1.26 (d, J=7.1 Hz, 3H, CHMe).

2-methyl-4-Bromo-7-methoxy-indan-1-one

To Eaton's reagent obtained from 153 g of P$_4$O$_{10}$ and 780 ml of MeSO$_3$H 149 g (0.544 mol) of 3-(2-bromo-5-methoxyphenyl)-2-methylpropanoic acid was added by vigorous stirring for 50 min at 60-62° C. The resulting mixture was additionally stirred for 30 min at the same temperature and then poured in a mixture of 2 kg of ice and 2000 cm$^3$ of cold water. The crude product was extracted with 800 ml of dichloromethane, the aqueous layer was then additionally extracted with 2×200 ml of dichloromethane per each 2 L of the aqueous phase. The combined organic extract was washed by aqueous K$_2$CO$_3$, dried over K$_2$CO$_3$, and then evaporated to dryness. The resulting red oil was distilled in vacuum at 155-170° C./5 mm Hg to yield 104 g (75%) of 2-methyl-4-bromo-7-methoxy-indan-1-one as yellow oil which crystallizes slowly at room temperature.

Anal. calc. for C$_{11}$H$_{11}$BrO$_2$: C, 51.79; H, 4.35. Found: C, 51.84; H, 4.40.

$^1$H NMR (CDCl$_3$): δ 7.64 (d, J=8.6 Hz, 1H, 5-H), 6.73 (d, J=8.6 Hz, 1H, 6-H), 3.94 (s, 3H, OMe), 3.27 (dd, J=17.7 Hz, J=8.1 Hz, 1H, CHH'CH), 2.70 (m, 1H, CHMe), 2.59 (dd, J=17.7 Hz, J=3.9 Hz, 1H, CHH'CH), 1.31 (d, J=7.5 Hz, 3H, 2-Me).

2-methyl-4-Bromo-1,7-dimethoxyindane

To a mixture of 104 g (0.407 mmol) of 2-methyl-4-bromo-7-methoxyindan-1-one and 15.0 g (0.397 mmol) of NaBH$_4$ in a mixture of 410 ml of THF 205 ml of methanol was added dropwise with vigorous stirring for 4 h at +5° C. This mixture was stirred overnight at room temperature and then added to 1 liter of cold water. The resulting mixture was carefully acidified by 2 M HCl to pH 5.0, and the formed indan-1-ol was extracted with 500 ml of dichloromethane.

The aqueous layer was additionally extracted with 2×200 ml of dichloromethane. The combined organic extract was evaporated to dryness. To the resulting yellowish liquid of the crude 2-methyl 4-bromo-7-methoxyindan-1-ol 800 ml of DMSO, 92.0 g (1.64 mol, 4.0 eq) of KOH, and 116 g (0.817 mol, 2.0 eq) of MeI were added. This mixture was stirred for 3 h at ambient temperature and then added to 3 L of cold water. The crude product was extracted with dichloromethane (500 ml, then 3×250 ml). The combined organic extract was washed 5 times by 1 liter of water and then evaporated to dryness. The product was isolated by flash chromatography on silica gel 60 (40-63 μm; eluent: hexanes-dichloromethane=2:1, then 1:2 and, finally, 1:5, vol.) followed by rectification in vacuum, 149-154° C./8 mm Hg. Yield 96.0 g (87%) of a ca. 1 to 2 mixture of two diastereomers.

Anal. calc. for C$_{12}$H$_{15}$BrO$_2$: C, 53.15; H, 5.58. Found: C, 53.08; H, 5.65.

$^1$H NMR (CDCl$_3$), major diastereomer: δ 7.36 (d, J=8.6 Hz, 1H, 5-H), 6.62 (d, J=8.6 Hz, 1H, 6-H), 4.68 (d, J=1.3 Hz, 1H, CHOMe), 3.82 (s, 3H, 7-OMe), 3.38 (s, 3H, 1-OMe), 3.27 (dd, J=16.7 Hz, J=7.3 Hz, 1H, 3-H), 2.54 (m, 1H, 2-H), 2.41 (dd, J=16.7 Hz, J=2.0 Hz, 1H, 3'-H), 1.03 (d, J=7.3 Hz, 3H, 2-Me); minor diastereomer: δ 7.33 (d, J=8.6 Hz, 1H, 5-H), 6.61 (d, J=8.6 Hz, 1H, 6-H), 4.69 (d, J=5.6 Hz, 1H, CHOMe), 3.81 (s, 3H, 7-OMe), 3.38 (s, 3H, 1-OMe), 3.27 (dd, J=16.0 Hz, J=7.8 Hz, 1H, 3-H), 2.41 (dd, J=16.0 Hz, J=9.6 Hz, 1H, 3'-H), 2.54 (m, 1H, 2-H), 1.22 (d, J=6.9 Hz, 3H, 2-Me).

2-methyl-4-methoxy-7-(3,5-Di-tert-butylphenyl)-1H-indene

To a solution of 3,5-di-tert-butylphenylmagnesium bromide obtained from 59.3 g (0.220 mol) of 1-bromo-3,5-di-tert-butylbenzene and 7.60 g (0.313 mol, 1.42 eqv.) of magnesium turnings in 450 ml of THF 1.00 g (1.28 mmol, 0.65 mol. %) NiCl$_2$(PPh$_3$)IPr and a solution of 53.4 g (0.197 mol) of 2-methyl-4-bromo-1,7-dimethoxyindane in 50 ml of THF were added. A vigorous reflux occurs approximately after ca. 30 sec and ceased after the following 30 sec. This mixture was stirred for 30 min at room temperature. Finally, 1000 ml of water and then 50 ml of 12 M HCl were added. The product was extracted with 500 ml of dichloromethane, organic layer was separated, the aqueous layer was additionally extracted with 200 ml of dichloromethane.

The combined organic extract was dried over K$_2$CO$_3$, passed through a short column with silica gel 60 (40-63 μm), and then evaporated to dryness. To the residue dissolved in 700 ml of toluene 1.4 g of TsOH was added. This solution was refluxed using Dean-Stark head for 20 min, cooled to room temperature, washed with 200 ml of 10% aqueous NaHCO$_3$. The organic layer was separated, the aqueous layer was extracted with 2×100 ml of dichloromethane. The combined organic solution was evaporated to dryness. The product was isolated by flash chromatography on silica gel 60 (40-63 um; eluent: hexane-dichloromethane=10:1, then 1:1, vol.). This procedure gave 67.6 g (99%) of 2-methyl-4-methoxy-7-(3,5-di-tert-butylphenyl)-1H-indene as a yellowish crystalline powder. The latter can be recrystallized from n-hexane with marginal loss of weight.

Anal. calc. for $C_{25}H_{32}O$: C, 86.15; H, 9.25. Found: C, 86.09; H, 9.23.

$^1$H NMR (CDCl$_3$): δ 7.40 (m, 1H, 4-H in tBu$_2$C$_6$H$_3$), 7.35 (m, 2H, 2,6-H in tBu$_2$C$_6$H$_3$), 7.15 (d, J=8.4 Hz, 1H, 6-H in indenyl), 6.88 (d, J=8.4 Hz, 1H, 5-H in indenyl), 6.70 (m, 1H, 3-H in indenyl), 3.92 (s, 3H, OMe), 3.41 (m, 2H, 2,2'-H in indenyl), 2.15 (s, 3H, 2-Me in indenyl), 1.38 (s, 18H, tBu).

Chloro[2-methyl-4-(3,5-di-tert-butylphenyl)-7-methoxy-1H-inden-1-yl]dimethylsilane To a solution of 13.1 g (37.5 mmol) of 2-methyl-4-methoxy-7-(3,5-di-tert-butylphenyl)-1H-indene in 200 ml of toluene 15.0 ml (37.5 mmol) of 2.5 M nBuLi in hexanes was added at room temperature. The resulting viscous solution was stirred for 2 h, and then 10 ml of THF was added. The formed suspension was stirred for 12 h at room temperature, ca. 2 h at 60° C., cooled to −20° C., and 24.0 g (0.186 mol, 5 eq) of dichlorodimethylsilane was added in one portion. The resulting solution was warmed to room temperature, stirred for 2 h at this temperature, evaporated to ca. ½ of its volume, and then filtered through glass frit (G3). The precipitate was additionally washed by 2×30 ml of toluene. The combined filtrate was evaporated to dryness to give a viscous yellowish oil which contained ca. 90% of chloro[2-methyl-4-(3,5-di-tert-butylphenyl)-7-methoxy-1H-inden-1-yl]dimethylsilane. This product was further used without any additional purification.

Anal. calc. for $C_{27}H_{37}ClOSi$: C, 73.51; H, 8.45. Found: C, 73.70; H, 8.57.

$^1$H NMR (CDCl$_3$): δ 7.41 (m, 1H, 4-H in tBu$_2$C$_6$H$_3$), 7.34 (m, 2H, 2,6-H in tBu$_2$C$_6$H$_3$), 7.29 (d, J=8.5 Hz, 1H, 6-H in indenyl), 6.76 (m, 1H, 3-H in indenyl), 6.74 (d, J=8.5 Hz, 1H, 5-H in indenyl), 3.89 (s, 3H, OMe), 3.84 (s, 1H, 1-H in indenyl), 2.31 (s, 3H, 2-Me in indenyl), 1.40 (s, 18H, tBu), 0.64 (s, 3H, SiMeMe'Cl), 0.01 (s, 3H, SiMeMe'Cl).

[2-methyl-4-(4-tert-Butylphenyl)-1H-inden-1-yl]-[2-methyl-4-(3,5-di-tert-butylphenyl)-7-methoxy-1H-inden-1-yl]dimethylsilane To a solution of 9.84 g (37.5 mmol) of 2-methyl-7-(4-tert-butylphenyl)-1H-indene in 200 ml of ether 15.0 ml (37.5 mmol) of 2.5 M nBuLi in hexanes was added in one portion at −40° C. This mixture was stirred overnight at room temperature, then cooled to −40° C., and 270 mg of CuCN was added. The resulting mixture was stirred for 1 h at −20° C., then cooled to −30° C., and a solution of the above obtained chloro[2-methyl-4-(3,5-di-tert-butylphenyl)-7-methoxy-1H-inden-1-yl]dimethylsilane (37.5 mmol) in 200 ml of ether was added in one portion. This mixture was stirred overnight at ambient temperature, then 0.5 ml of water was added. This solution was filtered through a pad of silica gel 60 (40-63 um) which was additionally washed by dichloromethane. The combined organic elute was evaporated to dryness and dried in vacuum.

This procedure gave 25.1 g of the title compound of ca. 90% purity as a yellowish glass. This product was further used without an additional purification.

Anal. calc. for $C_{47}H_{58}OSi$: C, 84.63; H, 8.76. Found: C, 84.93; H, 8.96.

$^1$H NMR (CDCl$_3$): δ 7.17-7.69 (m, 24H), 6.77-6.90 (m, 4H), 4.12 (s, 1H), 4.02 (s, 1H), 3.98 (s, 1H), 3.96 (s, 3H), 3.95 (s, 1H), 3.92 (s, 3H), 2.42 (s, 3H), 2.25 (s, 3H), 2.24 (s, 3H), 2.10 (s, 3H), 1.45-1.46 (m, 54H), −0.11 (s, 3H), −0.12 (s, 3H), −0.21 (s, 3H), −0.26 (s, 3H).

Dimethylsilanediyl[2-methyl-4-(4-tert-butylphenyl)-1H-inden-1-yl]-[2-methyl-4-(3,5-di-tert-butylphenyl)-7-methoxy-1H-inden-1-yl]zirconium dichloride Complex MC1

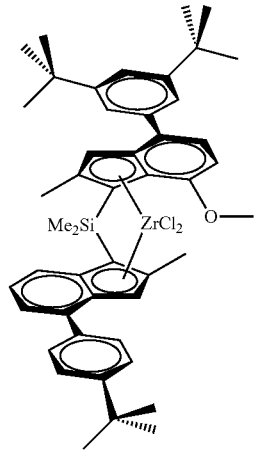

30.0 ml (75.0 mmol) of 2.5 M nBuLi in hexanes was added at room temperature to a solution of 25.1 g (ca. 37.5 mmol, 90% purity) of [2-methyl-4-(4-tert-butylphenyl)-1H-inden-1-yl][2-methyl-4-(3,5-di-tert-butylphenyl)-7-methoxy-1H-inden-1-yl]dimethylsilane in 300 ml of toluene. This mixture was stirred overnight at room temperature, then cooled to −25° C., and 14.2 g (37.5 mmol) of ZrCl$_4$(THF)$_2$ was added. This mixture was stirred for 24 h, then 20 ml of THF was added, and the resulting mixture was stirred for 2 h at 60° C. On the evidence of NMR spectroscopy, this procedure gave a solution including ca. 45 to 55 mixture of anti- and syn zirconocenes. This mixture was evaporated to dryness, a solution of the residue in 250 ml of THF was refluxed for 48 h and then evaporated to dryness. To the residue 200 ml of toluene was added, the formed mixture was stirred for 15 min at 50° C. and then filtered (at 50° C.) through glass frit (G4). This procedure gave, on the evidence of NMR spectroscopy, a pure solution of ca. 55 to 45 mixture of anti- and syn zirconocenes. This solution was evaporated to dryness. Multiple crystallizations of the residue from toluene-hexane mixtures (from 1:1 till 50:1, vol.) gave 22.0 g (71%) of a ca. 1 to 1 mixture of syn- and anti-complexes. The mother liquor was evaporated to dryness to give a ca. 9:1 mixture of anti- and syn-complexes contaminated by some impurities. This solid material was taken up in 40 ml of hot hexane, and the obtained mixture was filtered through glass frit (G4). Crystals precipitated after 24 h at room temperature from the filtrate were collected and dried in vacuum. This procedure gave 0.45 g of the anti isomer of the zirconocene.

Additional amount of this complex was obtained after evaporation of the mother liquor followed by crystallization of the residue from 15 ml of hexane. Total yield 0.65 g (2%) of pure anti-isomer as a reddish-orange crystalline solid.

Anal. calc. for $C_{47}H_{56}Cl_2OSiZr$: C, 68.25; H, 6.82. Found: C, 68.29; H, 6.89.

$^1$H NMR (CDCl$_3$): δ 7.68 (m, 1H, 7-H in indenyl bearing 4-tBuC$_6$H$_4$), 7.59-7.61 (m, 2H, 2,6-H in 4-tBuC$_6$H$_4$), 7.45-7.47 (m, 4H, 2,6-H in 3,5-tBu$_2$C$_6$H$_3$ and 5-H in indenyl bearing 3,5-tBu$_2$C$_6$H$_3$ and 3-H in indenyl), 7.36-7.39 (m, 3H, 7-H in indenyl bearing 4-tBuC$_6$H$_4$ and 4-H in 3,5-tBu$_2$C$_6$H$_3$ and 3-H in indenyl), 7.10 (dd, J=8.8 Hz, J=7.1 Hz, 1H, 6-H in indenyl bearing 4-tBuC$_6$H$_4$), 6.98-7.01 (m, 2H, 3,5-H in 4-tBuC6H4), 6.43 (d, J=Hz, 1H, 5-H in indenyl bearing 3,5-tBu$_2$C$_6$H$_3$), 3.91 (s, 3H, OMe), 2.30 (s, 3H, 2-Me in indenyl), 2.14 (s, 3H, 2-Me in indenyl), 1.35 (s, 9H, tBu in 4-tBuC$_6$H$_4$), 1.34 (s, 3H, SiMeMe'), 1.33 (s, 18H, tBu in 3,5-tBu$_2$C$_6$H$_3$), 1.22 (s, 3H, SiMeMe').

Complex Synthesis of MC2

5-Bromo-2-methylbenzaldehyde

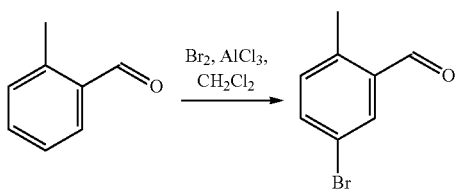

To a suspension of 344 g (2.58 mol, 1.5 eq.) of AlCl$_3$ in 1100 cm$^3$ of dichloromethane 206.8 g (1.72 mol) of 2-methylbenzaldehyde was added dropwise by vigorous stirring for 15 min at 5° C. The resulting mixture was stirred for 15 min at 5° C., and then 88.9 ml (276 g, 1.73 mol) of bromine was added for 1 h at this temperature. The final mixture was additionally stirred for 6 h at room temperature and then poured on 2 kg of ice. The organic layer was separated, the aqueous layer was extracted with 2×200 ml of dichloromethane. The combined organic extract was washed by aqueous NaHCO$_3$, dried over Na$_2$SO$_4$, and then evaporated to dryness to yield reddish liquid. This crude product was distilled in vacuum, b.p. 100-120° C./5 mm Hg. The obtained colorless liquid (which crystallizes at 5° C.) was dissolved in 900 ml of n-hexane. Crystals precipitated from this solution for 3 days at 5° C. were collected and dried in vacuum. On the evidence of NMR spectroscopy this mixture consists of 5-bromo-2-methylbenzaldehyde and 3-bromo-2-methylbenzaldehyde in ratio equal ca. 3 to 1. This mixture was recrystallized from 500 ml of hot n-hexane. White crystals precipitated at 5° C. were collected, washed by 150 ml of cold (+5° C.) n-hexane, and dried in vacuum (~60° C./20 mm Hg) to give colorless liquid which crystallizes at room temperature. Yield 80.9 g (24%) of 5-bromo-2-methylbenzaldehyde including ca. 2% of 3-bromo-2-methylbenzaldehyde.

Anal. calc. for C$_8$H$_7$BrO: C, 48.27; H, 3.54. Found: C, 48.05; H, 3.41.

$^1$H NMR (CDCl$_3$): δ 10.21 (s, 1H, CHO), 7.90 (d, J=2.2 Hz, 1H, 6-H), 7.57 (dd, J=8.2 Hz, J=2.3 Hz, 1H, 4-H), 7.14 (d, J=8.2 Hz, 1H, 3-H), 2.61 (s, 3H, Me).

$^{13}$C{$^1$H} NMR (CDCl$_3$): δ 191.0, 139.3, 136.4, 135.5, 134.1, 133.4, 120.0, 18.85.

5-Bromo-2-methylbenzyl chloride

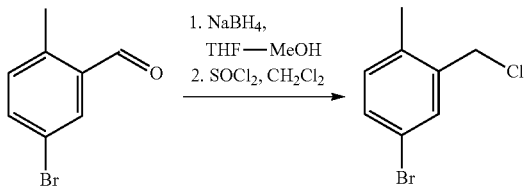

To a mixture of 80.9 g (0.406 mol) of 5-bromo-2-methylbenzaldehyde and 7.80 g (0.206 mol) of NaBH$_4$ in 300 ml of THF 200 ml of methanol was added dropwise by vigorous stirring for 5 h at 0-5° C. This mixture was stirred overnight at room temperature and then added to 1 liter of cold water. The resulting mixture was acidified by 2 M HCl to pH~1, and the formed (5-bromo-2-methylphenyl)methanol was extracted with 3×250 ml of dichloromethane. The combined organic extract was dried over Na$_2$SO$_4$ and evaporated to dryness. To the residue dissolved in 450 ml of dichloromethane 37 ml of SOCl$_2$ was added dropwise at +5° C. The resulting solution was stirred overnight at room temperature, evaporated to dryness, the residue was dissolved in 500 ml CH$_2$Cl$_2$, and the obtained solution was washed with 500 ml of water. The organic layer was separated, the aqueous layer was additionally extracted with 2×100 ml of dichloromethane. The combined organic extract was passed through a short pad of silica gel 60 (40-63 um), the filtrate was evaporated to dryness, and the residue was dried in vacuum to yield 5-bromo-2-methylbenzyl chloride as a slightly yellowish liquid which was further used without an additional purification.

Anal. calc. for C$_8$H$_8$BrCl: C, 43.77; H, 3.67. Found: C, 43.89; H, 3.80.

$^1$H NMR (CDCl$_3$): δ 7.45 (d, J=2.0 Hz, 1H, 3-H), 7.35 (dd, J=8.2 Hz, J=2.0 Hz, 1H, 5-H), 7.06 (d, J=8.2 Hz, 1H, 6-H), 4.53 (s, 2H, CH$_2$Cl), 2.36 (s, 3H, Me).

$^{13}$C{$^1$H} NMR (CDCl$_3$): δ 137.5, 136.0, 132.4, 132.3, 131.7, 119.5, 43.8, 18.3.

3-(5-Bromo-2-methylphenyl)-2-methylpropanoyl chloride

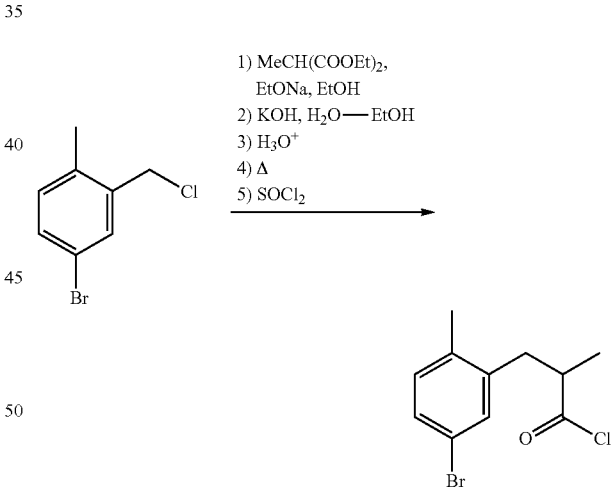

In a three-necked round-bottom flask 9.50 g (0.413 mol) of sodium metal was dissolved in 260 ml of dry ethanol. To the resulting solution 72.0 g (0.413 mol) of diethyl methylmalonate was added. This mixture was stirred for 15 min, then 5-bromo-2-methylbenzyl chloride prepared above was added by vigorous stirring at such a rate as to maintain gentle reflux. This mixture was refluxed for an additional 2 h and then cooled to room temperature. A solution of 85 g of KOH in 250 ml of water was added. The resulting mixture was refluxed for 4 h to saponificate the ester formed. Ethanol and water were distilled off until temperature reached 95° C., and 1000 ml of water and then 12 M HCl (to pH 1) were added to the residue. The precipitated substituted methylmalonic acid was filtered off, washed with 3×100 ml of water, and then decarboxylated at 180° C. to give 3-(5-bromo-2-methylphenyl)-2-methylpropanoic. A mixture of this acid and 105 ml of SOCl$_2$ was stirred at room temperature for 24 hours. After evaporation of an excess of thionyl chloride, the residue was distilled in vacuum to give 85.3 g (75% from 5-bromo-2-methylbenzaldehyde) 3-(5-bromo-2-methylphenyl)-2-methylpropanoyl chloride, b.p. 115° C./1 mm Hg.

Anal. calc. for C$_{11}$H$_{12}$BrClO: C, 47.94; H, 4.39. Found: C, 48.12; H, 4.45.

$^1$H NMR (CDCl$_3$): δ 7.28-7.26 (m, 2H, 6,4-H in Ph), 7.03 (d, J=7.7 Hz, 1H, 3-H in Ph), 3.18 (dd, J=13.8 Hz, J=5.9 Hz, 1H, ArCHH'), 3.10 (m, 1H, CHCOCl), 2.65 (dd, J=13.8 Hz, J=8.1 Hz, 1H, ArCHH'), 2.28 (s, 3H, ArMe), 1.29 (d, J=6.7 Hz, 3H, CHMe). $^{13}$C{$^1$H} NMR (CDCl$_3$): δ 176.9, 138.1, 135.2, 132.4, 132.2, 130.0, 119.5, 51.8, 36.1, 19.0, 16.6.

2,4-dimethyl-7-Bromo-indan-1-one

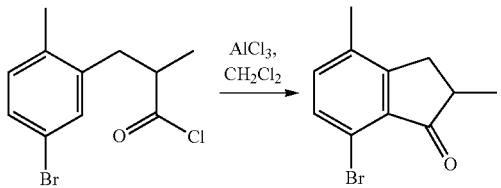

To a stirred suspension of 49.5 g (0.371 mol, 1.2 eq.) of AlCl$_3$ in 300 ml of dichloromethane a solution of 85.3 g (0.310 mol) of 3-(5-bromo-2-methylphenyl)-2-methylpropanoyl chloride in 50 ml of dichloromethane was added dropwise. This mixture was stirred overnight at room temperature and then poured on 500 g of ice. The organic layer was separated, and the aqueous layer was additionally extracted with 3×75 ml of dichloromethane. The combined organic extract was washed by aqueous K$_2$CO$_3$, dried over K$_2$CO$_3$, passed through a short pad of silica gel, and then evaporated to dryness. This procedure gave 74.0 g (>99%) of 2,4-dimethyl-7-bromo-indan-1-one as a light-orange liquid, solidified at room temperature, which was further used without an additional purification.

Anal. calc. for C$_{11}$H$_{11}$BrO: C, 55.25; H, 4.64. Found: C, 55.40; H, 4.81.

$^1$H NMR (CDCl$_3$): δ 7.41 (d, J=8.0 Hz, 1H, 6-H in indan-1-one), 7.21 (d, J=8.0 Hz, 1H, 5-H in indan-1-one), 3.24 (dd, J=17.3 Hz, J=7.9 Hz, 3-H in indan-1-one), 2.73 (m, 1H, 2-H in indan-1-one), 2.54 (dd, J=17.3 Hz, J=4.1 Hz, 1H, 3'-H in indan-1-one), 2.29 (s, 3H, 4-Me in indan-1-one), 1.33 (d, J=7.3 Hz, 3H, 2-Me in indan-1-one). $^{13}$C{$^1$H} NMR (CDCl$_3$): δ 207.0, 155.0, 135.6, 134.8, 133.1, 132.3, 116.5, 42.4, 33.0, 17.4, 16.4.

1-methoxy-2,4-dimethyl-7-Bromoindane

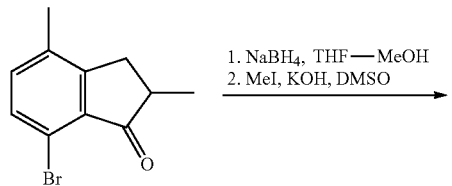

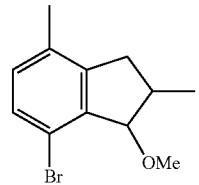

To a mixture of 74.0 g (0.310 mol) of 2,4-dimethyl-7-bromoindan-1-one and 5.86 g (0.155 mol) of NaBH$_4$ in 310 ml of THF 155 ml of methanol was added dropwise by vigorous stirring for 5 h at 0-5° C. This mixture was stirred overnight at room temperature and then added to 1 liter of cold water. The resulting mixture was acidified by 2 M HCl to pH-5, and then it was extracted with 3×250 ml of dichloromethane. The combined organic extract was dried over Na$_2$SO$_4$ and evaporated. The resulting orange oil was dissolved in 600 ml of DMSO, then 70 g (1.25 mol) of KOH and 88 g (0.62 mol) of MeI were added to the resulting solution. This mixture was stirred for 3 h at ambient temperature. Further on, the solution was decanted from an excess of KOH, the latter was washed with 2×200 ml of dichloromethane, and 2000 cm$^3$ of water was added to the combined solution. The organic layer was separated, and the aqueous layer was additionally extracted with 2×100 ml of dichloromethane. The combined organic extract was additionally washed with 5×1500 ml of water, dried over Na$_2$SO$_4$, and evaporated to dryness. Fractional distillation of the residue in vacuum gave 72.3 g (92%) of 1-methoxy-2,4-dimethyl-7-bromoindane, b.p. 107-112° C./5 mm Hg.

Anal. calc. for C$_{12}$H$_{15}$BrO: C, 56.49; H, 5.93. Found: C, 56.43; H, 6.02.

$^1$H NMR (CDCl$_3$): δ 7.26 (d, J=8.6 Hz, 1H, 6-H of anti-isomer), 7.24 (d, J=8.6 Hz, 1H, 6-H of syn-isomer), 6.94 (d, J=8.6 Hz, 1H, 5H of anti-isomer), 6.92 (d, J=8.6 Hz, 1H, 5H of syn-isomer), 4.57 (d, J=5.5 Hz, 1H, 1-H of syn-isomer), 4.42 (m, 1H, 1-H of anti-isomer), 3.53 (s, 3H, OMe of syn-isomer), 3.45 (s, 3H, OMe of anti-isomer), 3.27 (dd, J=16.6 Hz, J=7.3 Hz, 1H, 3-H of anti-isomer), 2.87 (dd, J=15.7 Hz, J=7.5 Hz, 1H, 3-H of syn-isomer), 2.68 (dd, J=15.7 Hz, J=9.8 Hz, 1H, 3'-H of syn-isomer), 2.57 (m, 1H, 2-H of anti-isomer), 2.44 (m, 1H, 2-H of syn-isomer), 2.39 (dd, J=16.6 Hz, J=1.4 Hz, 3'-H of anti-isomer), 2.18 (s, 6H, 4-Me of syn- and anti-isomers), 1.26 (d, J=6.9 Hz, 3H, 2-Me of syn-isomer), 1.05 (d, J=7.3 Hz, 2-Me of anti-isomer).

2,7-dimethyl-4-(3,5-Di-tert-butylphenyl)-1H-indene

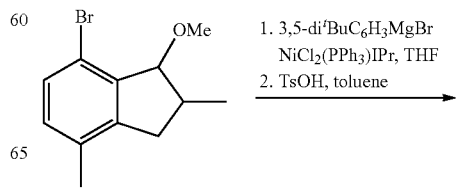

-continued

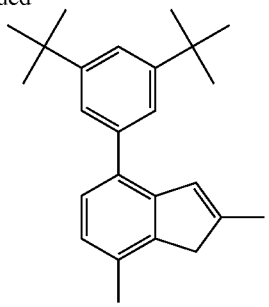

To a solution of 3,5-di-tert-butylphenylmagnesium bromide obtained from 59.0 g (0.219 mol) of 1-bromo-3,5-di-tert-butylbenzene and 9.31 g (0.383 mol, 1.75 eq.) of magnesium turnings in 550 ml of THF 1.0 g (1.28 mmol, 0.71 mol. %) NiCl$_2$(PPh$_3$)IPr and a solution of 46.1 g (0.181 mol) of 1-methoxy-2,4-dimethyl-7-bromoindane in 50 ml of THF were added. A moderate reflux occurs approximately after one minute which ceased after the following 30 sec. This mixture was refluxed additionally for 1 h. Finally, 50 ml of water was added, and the main part of THF was distilled off on rotary evaporator. Further on, 500 ml of dichloromethane and 500 ml of 2 M HCl were added to the residue. The organic layer was separated, the aqueous layer was additionally extracted with 100 ml of dichloromethane. The combined organic extract was evaporated to dryness to give a yellowish oil. To a solution of this oil in 700 ml of toluene 0.8 g of TsOH was added. The resulting mixture was refluxed using Dean-Stark head for 20 min, one more portion (0.8 g) of TsOH was added, and the mixture was refluxed for another 20 min. The resulting mixture cooled to room temperature was washed with 200 ml of 10% aqueous NaHCO$_3$. The organic layer was separated, the aqueous layer was additionally extracted with 2×100 ml of dichloromethane. The combined organic extract was evaporated to dryness, a solution of the residue in 500 ml of dichloromethane was passed through a short pad of silica gel 60 (40-63 um) and then evaporated to dryness to give yellowish crystalline material. This crude product was re-crystallization from 200 ml of hot n-hexane. Crystals precipitated from this solution at 5° C. were collected and dried in vacuum. This procedure gave 49.8 g of white microcrystalline product. The mother liquor was evaporated to dryness, and the main part of 1,3-di-tert-butylbenzene was distilled off at elevated temperature on rotary evaporator. The residue was then re-crystallized from 80 ml of hot n-hexane. This gave additional 6.21 g of the product. Thus, the total yield of 2,7-dimethyl-4-(3,5-di-tert-butylphenyl)-1H-indene was 56.0 g (93%).

Anal. calc. for C$_{25}$H$_{32}$: C, 90.30; H, 9.70. Found: C, 90.44; H, 9.89.

$^1$H NMR (CDCl$_3$): δ (t, J=1.8 Hz, 1H, 4-H in C$_6$H$_3$$^t$Bu$_2$), 7.33 (d, J=1.8 Hz, 2H, 2,6-H in C$_6$H$_3$$^t$Bu$_2$), 7.24 (d, J=7.7 Hz, 1H, 5-H in indenyl), 7.01 (d, J=7.7 Hz, 1H, 6-H in indenyl), 6.67 (m, 1H, 3-H in indenyl), 3.27 (s, 2H, 1-H in indenyl), 2.37 (s, 3H, 7-Me in indenyl), 2.16 (s, 3H, 2-Me in indenyl), 1.37 (s, 18H, $^t$Bu). $^{13}$C{$^1$H} NMR (CDCl$_3$): δ 150.5, 146.0, 143.1, 142.4, 140.2, 133.0, 131.3, 127.2, 126.7, 125.2, 123.3, 120.4, 42.0, 34.9, 31.5, 18.5, 17.0.

A Mixture of chloro[2,7-dimethyl-4-(3,5-di-tert-butylphenyl)-1H-inden-1-yl]dimethylsilane and chloro[2,4-dimethyl-7-(3,5-di-tert-butylphenyl)-1H-inden-1-yl]dimethylsilane

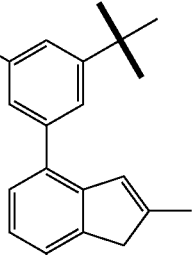

→

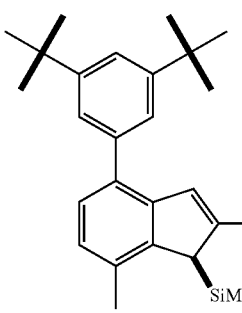

+

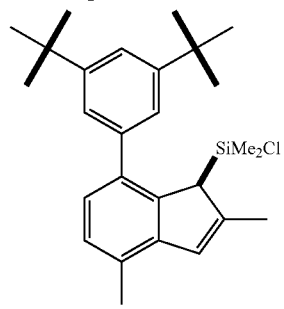

Method 1

To a solution of 12.5 g (37.5 mmol) of 2,7-dimethyl-4-(3,5-di-tert-butylphenyl)-1H-indene in 200 ml of toluene 15.0 ml (37.5 mmol) of 2.5 M $^n$BuLi in hexanes was added at room temperature. The obtained viscous solution was stirred for 10 h, and then 10 ml of THF was added. The resulting mixture was stirred for 2 h at 60° C., then cooled to −20° C., and 24.0 g (186 mmol, 5 eq.) of dichlorodimethylsilane was added in one portion. The formed solution was warmed to room temperature, refluxed for 1 h, then evaporated to ca. ½ of its volume, and finally filtered through glass frit (G3). The precipitate was additionally washed by 2×30 ml of toluene. The combined filtrate was evaporated to dryness to give a ca. 60:40 mixture of chloro [2,7-dimethyl-4-(3,5-di-tert-butylphenyl)-1H-inden-1-yl]dimethylsilane and chloro[2,4-dimethyl-7-(3,5-di-tert-butylphenyl)-1H-inden-1-yl]dimethylsilane. This mixture was further used without an additional purification.

Anal. calc. for C$_{27}$H$_{37}$ClSi: C, 76.28; H, 8.77. Found: C, 76.59; H, 9.02.

$^1$H NMR (CDCl$_3$): δ 7.48-7.44 (m, 4H, 2,4,6-H in C$_6$H$_3$$^t$Bu$_2$ of 1-st isomer and 4-H in C$_6$H$_3$$^t$Bu$_2$ of 2-nd isomer), 7.39 (d, J=1.8 Hz, 2H, 2,6-H in C$_6$H$_3$$^t$Bu$_2$ of 2-nd isomer), 7.29 (d, J=7.7 Hz, 1H, 6-H in indenyl of 2-nd isomer), 7.18 (d, J=7.7 Hz, 1H, 5-H in indenyl of 1-st isomer), 7.16 (d, J=7.7 Hz, 1H, 6-H in indenyl of 1-st isomer), 7.07 (d, J=7.7 Hz, 1H, 5-H in indenyl of 2-nd isomer), 6.83 (m, 1H, 3-H in indenyl of 2-nd isomer), 6.81 (m, 1H, 3-H in indenyl of 1-st isomer), 4.26 (s, 1H, 1-H in indenyl of 1-st isomer), 3.87 (s, 1H, 1-H in indenyl of 2-nd isomer), 2.51 (s, 3H, 7-Me in indenyl of 1-st isomer), 2.50 (s, 3H, 4-Me in indenyl of 2-nd isomer), 2.41 (s, 3H, 2-Me in indenyl of 1-st isomer), 2.34 (s, 3H, 2-Me in indenyl of 2-nd isomer), 1.44 (s, 18H, $^t$Bu of 2-nd isomer), 1.43 (s, 18H, $^t$Bu of 1-st isomer), 0.49 (s, 3H, SiMeMe'Cl of 2-nd isomer), 0.20 (s, 3H, SiMeMe'Cl of 2-nd isomer), −0.25 (s, 3H, SiMeMe'Cl of 1-st isomer), −0.25 (s, 3H, SiMeMe'Cl of 1-st isomer).

Method 2

To a solution of 12.5 g (37.5 mmol) of 2,7-dimethyl-4-(3,5-di-tert-butylphenyl)-1H-indene in 200 ml of ether 15.0 ml (37.5 mmol) of 2.5 M $^n$BuLi in hexanes was added at −30° C. The obtained yellowish solution was stirred for 12 h at room temperature, then cooled to −78° C., and 24.0 g (186 mmol, 5 eq.) of dichlorodimethylsilane was added in one portion. The resulting solution was slowly warmed to room temperature and then evaporated to dryness. The residue was dissolved in 100 ml of toluene, and the obtained mixture was filtered through glass frit (G3). The precipitate was additionally washed by 2×10 ml of toluene. The combined filtrate was evaporated to dryness to give a ca. 60:40 mixture of chloro[2,7-dimethyl-4-(3,5-di-tert-butylphenyl)-1H-inden-1-yl]dimethylsilane and chloro[2,4-dimethyl-7-(3,5-di-tert-butylphenyl)-1H-inden-1-yl]dimethylsilane. This mixture was further used without an additional purification.

Anal. calc. for $C_{27}H_{37}ClSi$: C, 76.28; H, 8.77. Found: C, 76.44; H, 8.95.

A Mixture of [2-methyl-4-(4-tert-butylphenyl)-1H-inden-1-yl][2,7-dimethyl-4-(3,5-di-tert-butylphenyl)-1H-inden-1-yl]dimethylsilane and [2-methyl-4-(4-tert-butylphenyl)-1H-inden-1-yl][2,4-dimethyl-7-(3,5-di-tert-butylphenyl)-1H-inden-1-yl]dimethylsilane

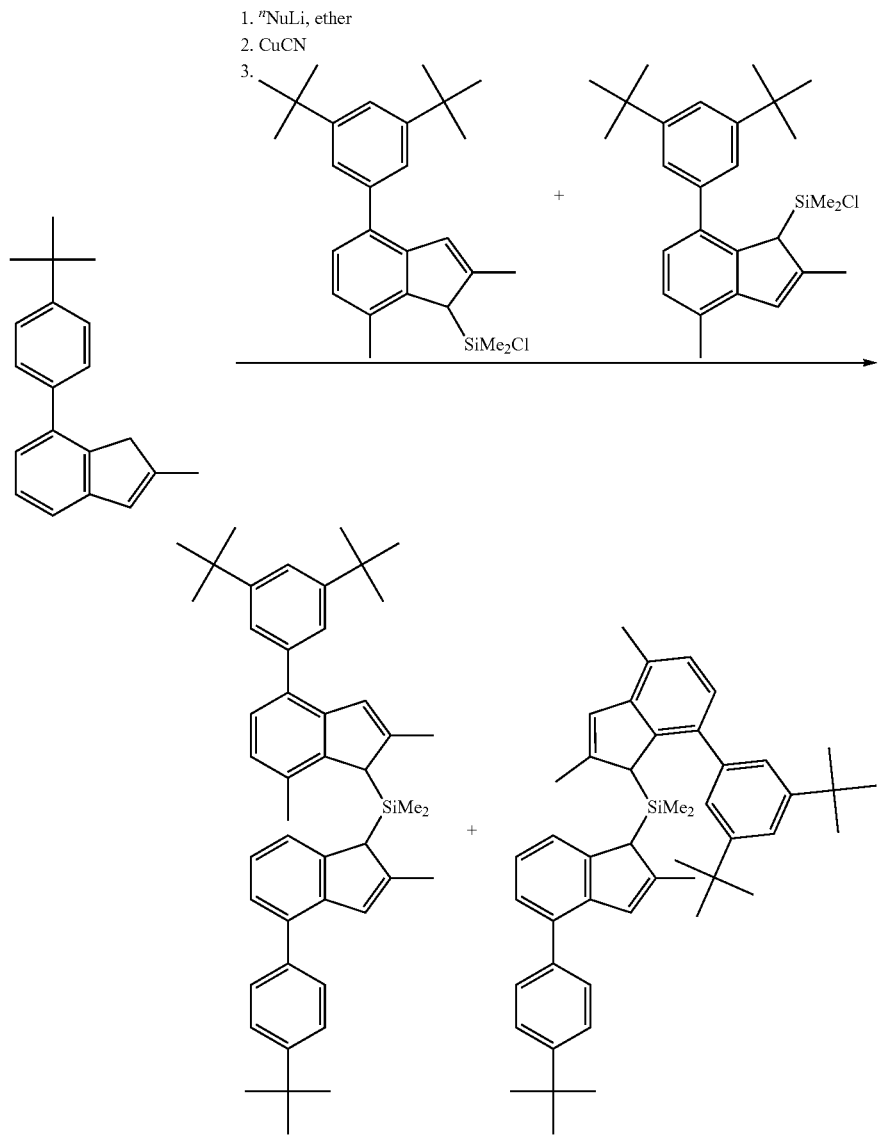

To a solution of 9.84 g (37.5 mmol) of 2-methyl-7-(4-tert-butylphenyl)-1H-indene in 200 ml of ether 15.0 ml (37.5 mmol) of 2.5 M $^n$BuLi in hexanes was added in one portion at −40° C. This mixture was stirred overnight at room temperature, then cooled to −40° C., and 270 mg of CuCN was added. The resulting mixture was stirred for 1 h at −20° C., then cooled to −30° C., and a solution of the above-described mixture of chloro[2,7-dimethyl-4-(3,5-di-tert-butylphenyl)-1H-inden-1-yl]dimethylsilane and chloro[2,4-dimethyl-7-(3,5-di-tert-butylphenyl)-1H-inden-1-yl]dimethylsilane (37.5 mmol) in 200 ml of ether was added in one portion. Further on, this mixture was stirred overnight at ambient temperature, then 0.5 ml of water was added. The obtained solution was filtered through a pad of silica gel 60 (40-63 um) which was additionally washed by 2×50 ml of dichloromethane. The combined organic elute was evaporated to dryness, and the residue was dried in vacuum at 50° C. This procedure gave 24.4 g of a ca. 1 to 1 mixture of [2-methyl-4-(4-tert-butylphenyl)-1H-inden-1-yl][2,7-dimethyl-4-(3,5-di-tert-butylphenyl)-1H-inden-1-yl]dimethylsilane and [2-methyl-4-(4-tert-butylphenyl)-1H-inden-1-yl][2,4-dimethyl-7-(3,5-di-tert-butylphenyl)-1H-inden-1-yl]dimethylsilane (>90% purity by NMR) which was further used without an additional purification.

Anal. calc. for $C_{47}H_{58}Si$: C, 86.71; H, 8.98. Found: C, 86.98; H, 9.13.

$^1$H NMR (CDCl$_3$): δ 7.52-7.36 (m), 7.29-6.93 (m), 6.83 (s), 6.80 (s), 6.77 (s), 6.73 (s), 6.61 (s), 6.59 (s), 4.40 (s), 4.32 (s), 4.01 (s), 3.90 (s), 3.74 (s), 3.73 (s), 3.11 (s), 2.93 (s), 2.46 (s), 2.39 (s), 2.31 (s), 2.30 (s), 2.29 (s), 2.24 (s), 2.11 (s), 1.91 (s), 1.81 (s), 1.38 (s), 1.35 (s), 1.33 (s), 1.29 (s), −0.17 (s), −0.27 (s), −0.59 (s), −0.63 (s), −0.69 (s).

Dimethylsilanediyl[2-methyl-4-(4-tert-butylphenyl)-inden-1-yl]-[2,7-dimethyl-4-(3,5-di-tert-butylphenyl)-inden-1-yl]zirconium dichloride (Complex MC2)

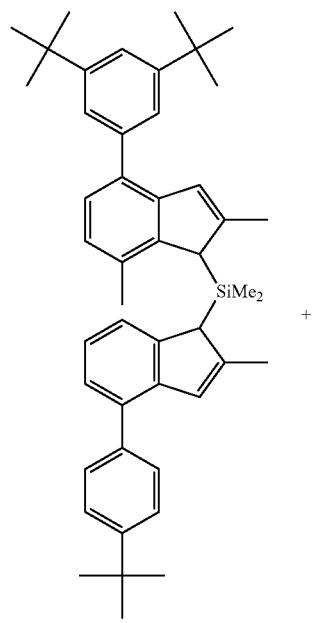

+

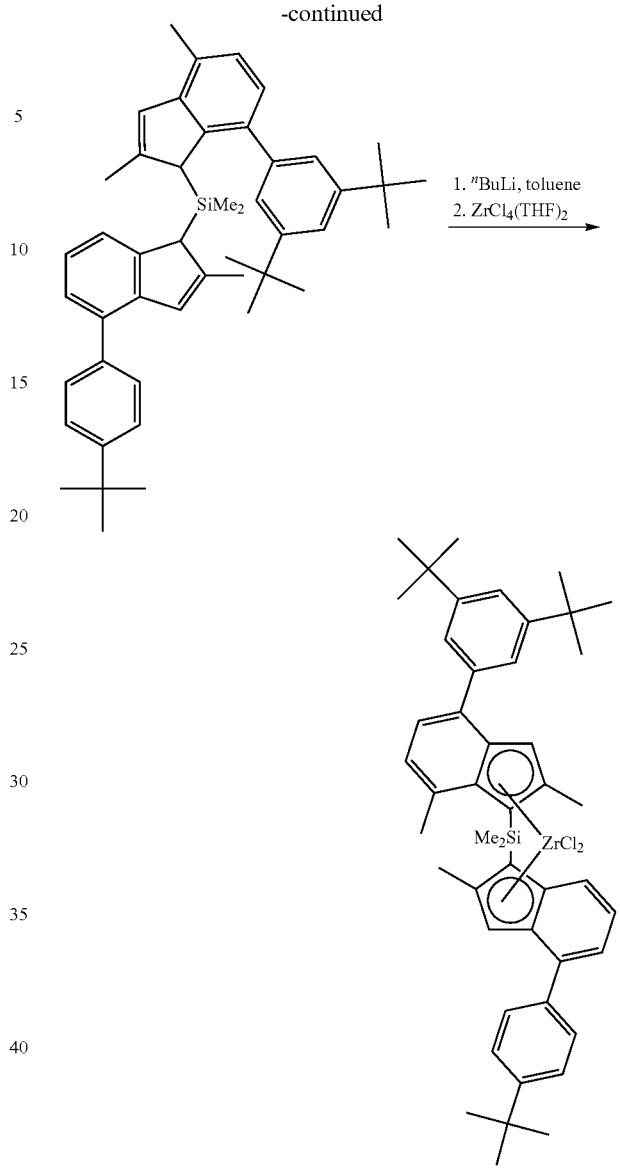

To a solution of 24.4 g (37.5 mmol, >90% purity) of a mixture of [2-methyl-4-(4-tert-butylphenyl)-1H-inden-1-yl][2,7-dimethyl-4-(3,5-di-tert-butylphenyl)-1H-inden-1-yl]-dimethylsilane and [2-methyl-4-(4-tert-butylphenyl)-1H-inden-1-yl][2,4-dimethyl-7-(3,5-di-tert-butylphenyl)-1H-inden-1-yl]dimethylsilane (as described above) in 300 ml of toluene 30.0 ml (75.0 mmol) of 2.5 M $^n$BuLi in hexanes was added in one portion at room temperature. This mixture was stirred overnight at this temperature, then 15 ml of THF was added, and the resulting mixture was stirred for 2 h at 60° C. Further on, 14.2 g (37.5 mmol) of ZrCl$_4$(THF)$_2$ was added at −25° C. The formed mixture was stirred for 24 h at room temperature, ca. 50 ml of the solvents was distilled off in vacuum, and the resulting solution was warmed to 80° C. and filtered through glass frit (G4). On the evidence of NMR spectroscopy, the obtained filtrate included a ca. 1 to 1 mixture of anti- and syn-zirconocenes. This solution was evaporated to dryness, the residue was poured on 100 ml of n-octane, and the formed mixture was filtered through glass frit (G3) at 80-90° C. The yellow-orange precipitate was washed with 2×30 ml of n-hexane and dried in vacuum. This procedure gave 13.2 g of a ca. 1:1 mixture of syn- and anti-zirconocenes. Crystals precipitated from the filtrate at room temperature were collected and dried in vacuum to give 1.43 g of a pure anti-zirconocene. The mother liquor was evaporated to dryness to give 0.45 g of a ca. 85:15 mixture of anti- and syn-zirconocenes. Thus, the total yield of ansa-zirconocenes was 15.1 g (50%). Further on, 13.2 g of a mixture of syn- and anti-zirconocenes was recrystallized from hot solvent consisting of 40 ml of toluene with 70 ml of n-hexane. Crystals precipitated at room temperature were collected, washed with 2×10 ml of n-hexane, and dried in vacuum. This procedure gave 7.32 g of syn-zirconocene contaminated with 5% of anti-isomer (analytically pure syn-isomer was obtained via re-crystallization of this product from a mixture of 50 ml of toluene and 10 ml of n-octane). Additionally, 0.72 g of a pure anti-zirconocene, 1.53 g of anti-zirconocene contaminated with 5% of syn-isomer, and 2.45 g of a ca. 2:1 mixture of anti- and syn-zirconocenes were obtained from the mother liquor by fractional crystallizations. Assignment in NMR spectra was made using the following abbreviations: $L^1$ for 2-methyl-4-(4-tert-butylphenyl)-1H-inden-1-yl and $L^2$ for 2,7-dimethyl-4-(3,5-di-tert-butylphenyl)-1H-inden-1-yl.

Anti-Zirconocene.

Anal. calc. for $C_{47}H_{56}Cl_2SiZr$: C, 69.59; H, 6.96. Found: C, 69.71; H, 7.19.

$^1$H NMR (CDCl$_3$): δ 7.66 (d, J=8.7 Hz, 1H, 7-H in L$^1$), 7.60-7.57 (m, 2H, 2,6-H in C$_6$H$_4{^t}$Bu), 7.50 (d, J=1.8 Hz, 2H, 2,6-H in C$_6$H$_3{^t}$Bu$_2$), 7.47-7.45 (m, 2H, 3,5-H in C$_6$H$_4{^t}$Bu), 7.41-7.39 (m, 2H, 5-H in L$^1$ and 4-H in C$_6$H$_3{^t}$Bu$_2$), 7.34 (d, J=7.1 Hz, 1H, 5-H in L$^2$), 7.13 (dd, J=8.7 Hz, J=7.1 Hz, 1H, 6-H in L$^1$), 7.07 (s, 1H, 3-H in L$^2$), 7.04 (s, 1H, 3-H in L$^1$), 7.01 (dd, J=7.1 Hz, J=0.8 Hz, 1H, 6-H in L$^2$), 2.67 (s, 3H, 7-Me in L$^2$), 2.36 (s, 3H, 2-Me in L$^2$), 2.17 (s, 3H, 2-Me in L$^1$), 1.38 (s, 3H, SiMeMe'), 1.35 (s, 9H, $^t$Bu in C$_6$H$_4{^t}$Bu), 1.32 (s, 18H, $^t$Bu in C$_6$H$_3{^t}$Bu$_2$), 1.30 (s, 3H, SiMeMe').

Syn-Zirconocene.

Anal. calc. for $C_{47}H_{56}Cl_2SiZr$: C, 69.59; H, 6.96. Found: C, 69.77; H, 7.24.

$^1$H NMR (CDCl$_3$): δ 7.77 (d, J=8.7 Hz, 1H, 7-H in L$^1$), 7.52-7.50 (m, 2H, 2,6-H in C$_6$H$_4{^t}$Bu), 7.45-7.43 (m, 4H, 3,5-H in C$_6$H$_4{^t}$Bu and 2,6-H in C$_6$H$_3{^t}$Bu$_2$), 7.38 (t, J=1.8 Hz, 4-H in C$_6$H$_3{^t}$Bu$_2$), 7.18 (d, J=6.8 Hz, 1H, 5-H in L$^1$), 7.11 (d, J=7.1 Hz, 1H, 5-H in L$^2$), 6.98 (s, 1H, 3-H in L$^2$), 6.93 (s, 1H, 3-H in L$^1$), 6.89 (dd, J=8.7 Hz, J=6.8 Hz, 1H, 6-H in L$^1$), 6.80 (dd, J=7.1 Hz, J=0.6 Hz, 1H, 6-H in L$^2$), 2.75 (s, 3H, 7-Me in L$^2$), 2.50 (s, 3H, 2-Me in L$^1$), 2.49 (s, 3H, 2-Me in L$^2$), 1.40 (s, 3H, SiMeMe'), 1.35 (s, 9H, $^t$Bu in C$_6$H$_4{^t}$Bu), 1.34 (s, 18H, $^t$Bu in C$_6$H$_3{^t}$Bu$_2$), 1.27 (s, 3H, SiMeMe').

Complex Synthesis MC2 with Hf

[2-methyl-4-(4-tert-Butylphenyl)-1H-inden-1-yl](chloro)dimethylsilane

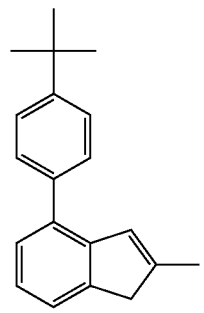

1. $^n$BuLi, toluene-THF
2. Me$_2$SiCl$_2$

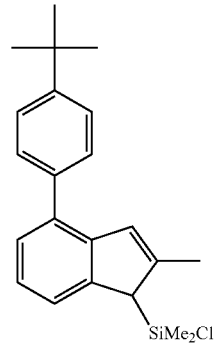

To a solution of 9.84 g (37.5 mmol) of 2-methyl-7-(4-tert-butylphenyl)-1H-indene in a mixture of 200 ml of toluene and 10 ml of THF 15.0 ml (37.5 mmol) of 2.5 M $^n$BuLi in hexanes was added at room temperature. The resulting solution was stirred for 2 h at 60° C., then cooled to 0° C., and 24.0 g (186 mmol, 5 eq.) of dichlorodimethylsilane was added in one portion. The formed solution was refluxed for 1 h, then evaporated to ca. 150 ml, and filtered through glass frit (G3). The precipitate was additionally washed by 2×30 ml of toluene. The combined filtrate was evaporated to dryness to give [2-methyl-4-(4-tert-butylphenyl)-1H-inden-1-yl](chloro)dimethylsilane as viscous yellowish oil which was further used without an additional purification.

Anal. calc. for $C_{22}H_{27}ClSi$: C, 74.44; H, 7.67. Found: C, 74.75; H, 7.89.

$^1$H NMR (CDCl$_3$): δ 7.54 (m, 4H, 2,3,5,6-H in C$_6$H$_4{^t}$Bu), 7.49 (d, J=7.5 Hz, 1H, 7-H in indenyl), 7.35 (d, J=7.3 Hz, 5-H in indenyl), 7.24 (t, J=7.5, 6-H in indenyl), 6.91 (m, 1H, 3-H in indenyl), 3.72 (s, 1H, 1-H in indenyl), 2.33 (s, 3H, 2-Me in indenyl), 1.45 (s, 9H, $^t$Bu), 0.49 (s, 3H, SiMeMe'), 0.24 (s, 3H, SiMeMe'). $^{13}C\{^1H\}$ NMR (CDCl$_3$): δ 149.7, 146.1, 143.1, 142.9, 138.1, 134.1, 128.5, 126.7, 126.1, 125.3, 123.3, 122.3, 50.4, 34.5, 31.4, 17.6, 1.0, 0.7.

A Mixture of [2-methyl-4-(4-tert-butylphenyl)-1H-inden-1-yl][2,7-dimethyl-4-(3,5-di-tert-butylphenyl)-1H-inden-1-yl]dimethylsilane and [2-methyl-4-(4-tert-butylphenyl)-1H-inden-1-yl][2,4-dimethyl-7-(3,5-di-tert-butylphenyl)-1H-inden-1-yl]dimethylsilane

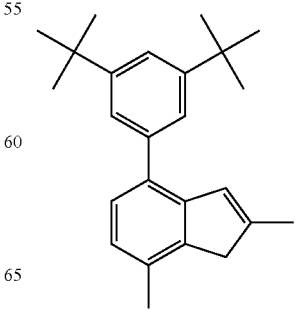

1. $^n$BuLi, ether
2. CuCN
3.

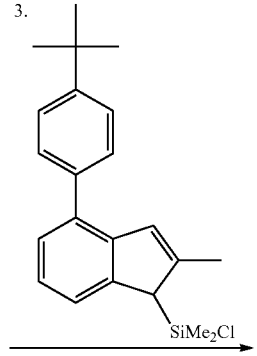

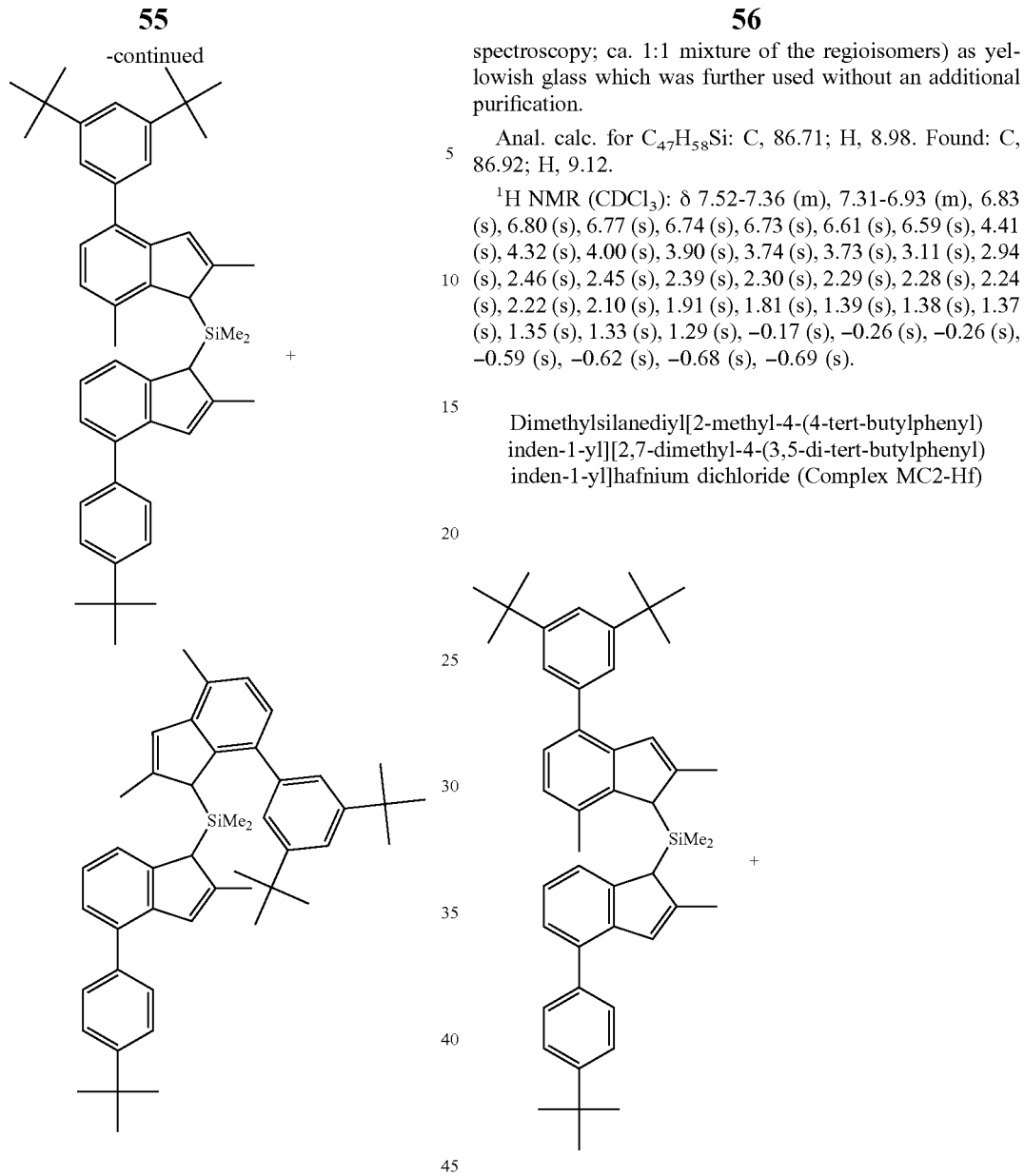

spectroscopy; ca. 1:1 mixture of the regioisomers) as yellowish glass which was further used without an additional purification.

Anal. calc. for $C_{47}H_{58}Si$: C, 86.71; H, 8.98. Found: C, 86.92; H, 9.12.

$^1$H NMR (CDCl$_3$): δ 7.52-7.36 (m), 7.31-6.93 (m), 6.83 (s), 6.80 (s), 6.77 (s), 6.74 (s), 6.73 (s), 6.61 (s), 6.59 (s), 4.41 (s), 4.32 (s), 4.00 (s), 3.90 (s), 3.74 (s), 3.73 (s), 3.11 (s), 2.94 (s), 2.46 (s), 2.45 (s), 2.39 (s), 2.30 (s), 2.29 (s), 2.28 (s), 2.24 (s), 2.22 (s), 2.10 (s), 1.91 (s), 1.81 (s), 1.39 (s), 1.38 (s), 1.37 (s), 1.35 (s), 1.33 (s), 1.29 (s), −0.17 (s), −0.26 (s), −0.26 (s), −0.59 (s), −0.62 (s), −0.68 (s), −0.69 (s).

Dimethylsilanediyl[2-methyl-4-(4-tert-butylphenyl)inden-1-yl][2,7-dimethyl-4-(3,5-di-tert-butylphenyl)inden-1-yl]hafnium dichloride (Complex MC2-Hf)

To a solution of 12.5 g (37.5 mmol) of 2,7-dimethyl-4-(3,5-di-tert-butylphenyl)-1H-indene in 200 ml of ether 15.0 ml (37.5 mmol) of 2.5 M $^n$BuLi in hexanes was added in one portion at −40° C. The resulting mixture was stirred overnight at room temperature, then cooled to −40° C., and 1.68 g (18.8 mmol, 0.5 eq.) of CuCN was added. The formed mixture was stirred for 1 h at −20° C., then cooled to −40° C., and then a solution 13.3 g (37.5 mmol) of [2-methyl-4-(4-tert-butylphenyl)-1H-inden-1-yl](chloro)dimethylsilane in 200 ml of ether was added in one portion. Further on, this mixture was stirred overnight at ambient temperature, and then 0.5 ml of water was added. The formed mixture was filtered through a pad of silica gel 60 (40-63 um) which was additionally washed by dichloromethane. The combined organic elute was evaporated to dryness and dried in vacuum. This procedure gave 24.0 g (36.9 mmol, 98%) of a mixture of [2-methyl-4-(4-tert-butylphenyl)-1H-inden-1-yl][2,7-dimethyl-4-(3,5-di-tert-butylphenyl)-1H-inden-1-yl]dimethylsilane and [2-methyl-4-(4-tert-butylphenyl)-1H-inden-1-yl][2,4-dimethyl-7-(3,5-di-tert-butylphenyl)-1H-inden-1-yl]dimethylsilane (>90% purity by NMR

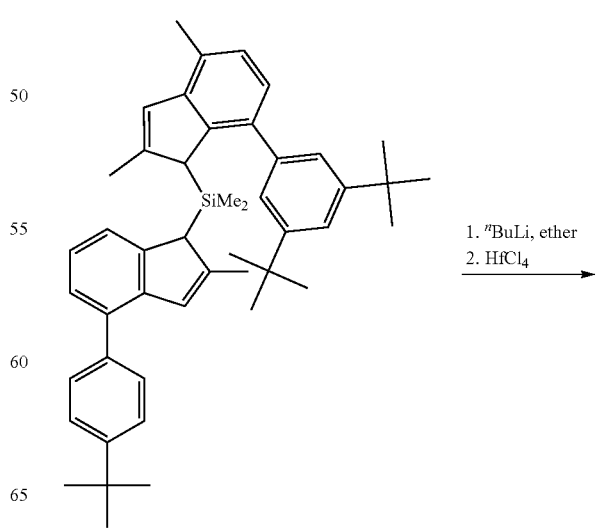

1. $^n$BuLi, ether
2. HfCl$_4$
→

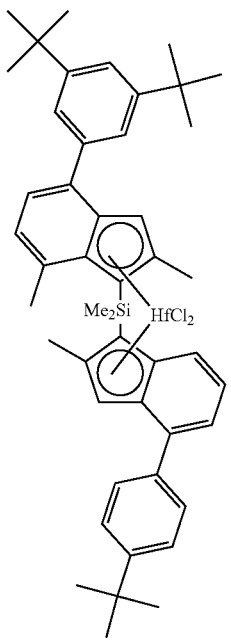

To a solution of 24.0 g (36.9 mmol, >90% purity) of a mixture of [2-methyl-4-(4-tert-butylphenyl)-1H-inden-1-yl][2,7-dimethyl-4-(3,5-di-tert-butylphenyl)-1H-inden-1-yl]dimethylsilane and [2-methyl-4-(4-tert-butylphenyl)-1H-inden-1-yl][2,4-dimethyl-7-(3,5-di-tert-butylphenyl)-1H-inden-1-yl]dimethylsilane (as described above) in 250 ml of ether 29.5 ml (73.8 mmol) of 2.5 M $^n$BuLi in hexanes was added in one portion at −20° C. This mixture was stirred overnight at room temperature, then cooled to −60° C., and 11.8 g (36.9 mmol) of HfCl$_4$ was added. The resulting mixture was stirred for 24 h, then filtered through glass frit (G4), and the precipitate was washed with 30 ml of ether. On the evidence of NMR spectroscopy, this precipitate was pure syn-zirconocene while the filtrate included a mixture of three isomeric complexes, i.e. the desired anti-hafnocene (55%), anti-hafnocene (25%), and one more isomeric ansa-hafnocene of unknown structure (20%). The precipitate was dissolved in 100 ml of hot toluene, and the formed suspension was filtered through glass frit (G4). The filtrate was evaporated to ca. 30 ml and then heated to obtain clear solution. Crystals precipitated from this solution at room temperature were collected, washed by 15 ml of cold n-hexane, and then dried in vacuum. This procedure gave 4.30 g (13%) of pure syn-complex. The mother liquor was evaporated to ca. 5 ml, and 80 ml of n-hexane was added. Crystals precipitated from the formed solution at room temperature were collected and dried in vacuum. This procedure gave 1.38 g (4%) of syn-complex contaminated with ca. 8% of anti-isomer. The mother liquor was evaporated to dryness, the residue was re-crystallized from 40 ml of hot n-hexane. Crystals precipitated from this solution after 4 h at room temperature were collected and dried in vacuum to give 0.28 g (1%) of the desired anti-complex contaminated with ca. 5% of syn-isomer. Additional crystalline material was obtained from the mother liquor after 3 days at room temperature. These crystals were collected and dried in vacuum to give 1.31 g (4%) of anti-complex of ca. 93% purity (i.e. 7% of unknown impurity). Assignment in NMR spectra was made using the following abbreviations: L$^1$ for 2-methyl-4-(4-tert-butylphenyl)-1H-inden-1-yl and L$^2$ for 2,7-dimethyl-4-(3,5-di-tert-butylphenyl)-1H-inden-1-yl.

Anti-Zirconocene.

Anal. calc. for C$_{47}$H$_{56}$Cl$_2$HfSi: C, 62.83; H, 6.28. Found: C, 62.87; H, 6.39.

$^1$H NMR (CDCl$_3$): δ 7.69 (d, J=8.5 Hz, 1H, 7-H in L$^1$), 7.58-7.56 (m, 2H, 2,6-H in C$_6$H$_4$$^t$Bu), 7.48 (d, J=1.1 Hz, 2H, 2,6-H in C$_6$H$_3$$^t$Bu$_2$), 7.46-7.44 (m, 2H, 3,5-H in C$_6$H$_4$$^t$Bu), 7.40-7.36 (m, 2H, 5-H in L$^1$ and 4-H in C$_6$H$_3$$^t$Bu$_2$), 7.31 (d, J=7.1 Hz, 1H, 5-H in L$^2$), 7.09 (dd, J=8.5 Hz, J=7.3 Hz, 1H, 6-H in L$^1$), 7.01-6.94 (m, 3H, 3-H in L$^2$, 3-H in L$^1$, 6-H in L$^2$), 2.68 (s, 3H, 7-Me in L$^2$), 2.45 (s, 3H, 2-Me in L$^2$), 2.24 (s, 3H, 2-Me in L$^1$), 1.38 (s, 3H, SiMeMe'), 1.35 (s, 9H, $^t$Bu in C$_6$H$_4$$^t$Bu), 1.32 (s, 18H, $^t$Bu in C$_6$H$_3$$^t$Bu$_2$), 1.29 (s, 3H, SiMeMe').

Syn-Zirconocenes.

Anal. calc. for C$_{47}$H$_{56}$Cl$_2$HfSi: C, 62.83; H, 6.28. Found: C, 62.98; H, 6.44.

$^1$H NMR (CDCl$_3$): δ 7.79 (d, J=8.7 Hz, 1H, 7-H in L$^1$), 7.51-7.49 (m, 2H, 2,6-H in C$_6$H$_4$$^t$Bu), 7.45-7.43 (m, 4H, 3,5-H in C$_6$H$_4$$^t$Bu and 2,6-H in C$_6$H$_3$$^t$Bu$_2$), 7.38 (s, 4-H in C$_6$H$_3$$^t$Bu$_2$), 7.16 (d, J=6.9 Hz, 1H, 5-H in L$^1$), 7.11 (d, J=6.9 Hz, 1H, 5-H in L$^2$), 6.88-6.86 (m, 2H, 3-H in L$^2$ and 6-H in L$^1$), 6.84 (s, 1H, 3-H in L$^1$), 6.77 (d, J=6.9 Hz, 1H, 6-H in L$^2$), 2.77 (s, 3H, 7-Me in L$^2$), 2.61 (s, 3H, 2-Me in L$^1$), 2.61 (s, 3H, 2-Me in L$^2$), 1.39 (s, 3H, SiMeMe'), 1.35 (s, 9H, $^t$Bu in C$_6$H$_4$$^t$Bu), 1.34 (s, 18H, $^t$Bu in C$_6$H$_3$$^t$Bu$_2$), 1.28 (s, 3H, SiMeMe').

Complex Synthesis of MC3

[2-methyl-4-(4-tert-butylphenyl)-6-tert-Butyl-1H-inden-1-yl][2-methyl-4-(3,5-di-tert-butylphenyl)-7-methoxy-1H-inden-1-yl]dimethylsilane

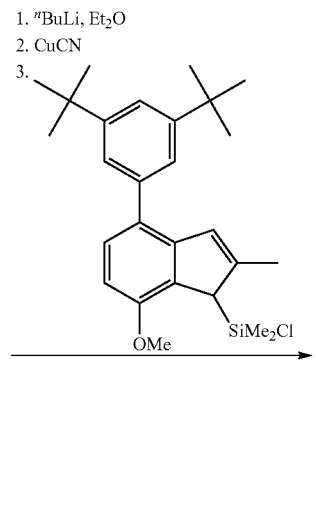

Dimethylsilanediyl[2-methyl-4-(4-tert-butylphenyl)-6-tert-butyl-inden-1-yl]-[2-methyl-4-(3,5-di-tert-butylphenyl)-7-methoxy-inden-1-yl]zirconium dichloride (complex MC3)

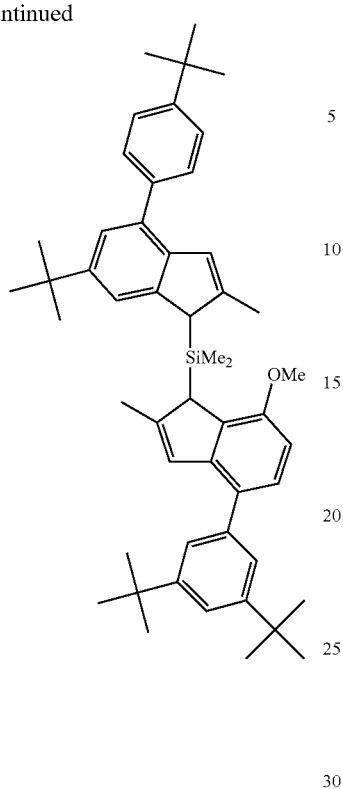

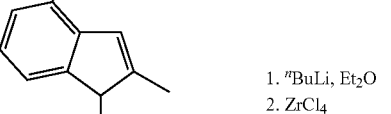

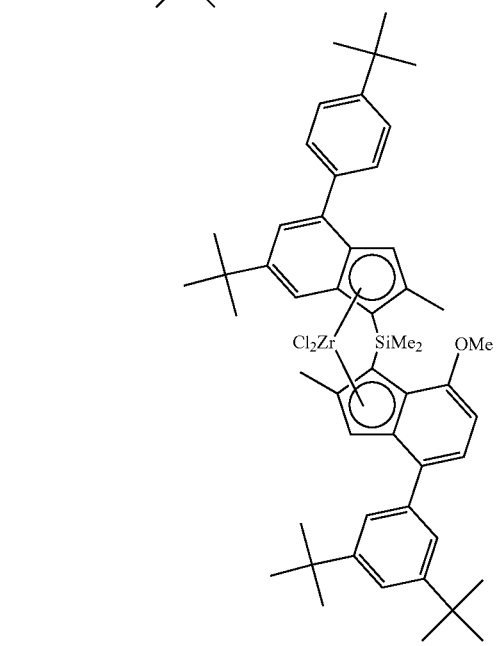

To a solution of 11.9 g (37.5 mmol) of 2-methyl-5-tert-butyl-7-(4-tert-butylphenyl)-1H-indene in 200 ml of ether 15.0 ml (37.5 mmol) of 2.5 M ⁿBuLi in hexanes was added in one portion at −40° C. This mixture was stirred overnight at room temperature, then cooled to −40° C., and 200 mg of CuCN was added. The resulting mixture was stirred for 1 h at −20° C., then cooled to −30° C., and a solution of 37.5 mmol of chloro[2-methyl-4-(3,5-di-tert-butylphenyl)-7-methoxy-1H-inden-1-yl]dimethylsilane (obtained as described in synthesis of complex D8, i.e. a ca. 90:10 mixture of the isomers) in 200 ml of ether was added in one portion. Further on, this mixture was stirred overnight at ambient temperature, then 0.5 ml of water was added. This solution was filtered through a pad of silica gel 60 (40-63 um) which was additionally washed by 50 ml of dichloromethane. The combined organic elute was evaporated to dryness, and the residue was dried in vacuum. The product was isolated by flash-chromatography on silica gel 60 (40-63 um; eluent:hexanes-dichloromethane=10:1, vol., then 3:1, vol.). This procedure gave 14.3 g (53%) of [2-methyl-4-(4-tert-butylphenyl)-6-tert-butyl-1H-inden-1-yl][2-methyl-4-(3,5-di-tert-butylphenyl)-7-methoxy-1H-inden-1-yl]dimethylsilane of ca. 90% purity (on the evidence of NMR spectroscopy).

Anal. calc. for $C_{51}H_{66}OSi$: C, 84.70; H, 9.20. Found: C, 84.99; H, 9.46.

$^1$H NMR (CDCl$_3$): δ 7.71 (s), 7.51-7.23 (m), 6.79 (m), 6.76-6.73 (m), 6.69 (m), 4.06 (s), 3.92 (s), 3.87 (s), 3.86 (s), 2.34 (s), 2.15 (s), 2.14 (s), 1.99 (s), 1.39 (s), 1.39 (s), 1.38 (s), 1.34 (s), −0.19 (s), −0.21 (s), −0.28 (s), −0.33 (s).

To a solution of 14.3 g (ca. 19.8 mmol) of [2-methyl-6-tert-butyl-4-(4-tert-butylphenyl)-1H-inden-1-yl][2-methyl-4-(3,5-di-tert-butylphenyl)-7-methoxy-1H-inden-1-yl]dimethylsilane of 90% purity in 250 ml of ether 15.8 ml (39.5 mmol) of 2.5 M ⁿBuLi in hexanes was added in one portion at −30° C. This mixture was stirred overnight at room temperature, then cooled to −35° C., and 4.61 g (19.8 mmol) of ZrCl$_4$ was added. The reaction mixture was stirred for 24 h, then evaporated to dryness, and the residue was dissolved in 250 ml of warm toluene. The formed hot suspension was filtered through glass frit (G4). On the evidence of NMR spectroscopy the filtrate included a ca. 60 to 40 mixture of anti- and syn-zirconocenes. This filtrate was evaporated to 75 ml, and 75 ml of n-hexane was added. Crystals precipitated at room temperature were collected, washed with 30 ml of a ca. 1 to 1 mixture toluene-n-hexane, 30 ml of n-hexane, and then dried in vacuum. This procedure gave 3.00 g (17%) of syn-zirconocene contaminated with ca. 4% of anti-isomer. The mother liquor was evaporated to dryness, and the residue was re-crystallized from a hot mixture of 30 ml of toluene and 100 ml of n-hexane. Crystals precipitated at room temperature were collected, washed with 20 ml of a ca. 1:2 mixture of toluene and n-hexane, 20 ml of n-hexane, and then dried in vacuum. This procedure gave 2.30 g (13%) of pure anti-zirconocene. The mother liquor was evaporated to dryness, and 50 ml of n-hexane was added to the residue. The formed suspension was filtered through glass frit (G3), and the precipitate was dried in vacuum. This procedure gave 6.60 g of a ca. 65:35 mixture of anti- and syn-zirconocenes. Thus, the total yield of ansa-zirconocenes was 11.9 g (68%). Assignment in NMR spectra was made using the following abbreviations: $L^1$ for 2-methyl-4-(4-tert-butylphenyl)-6-tert-butyl-1H-inden-1-yl and $L^2$ for 2-methyl-4-(3,5-di-tert-butylphenyl)-7-methoxy-1H-inden-1-yl.

Anti-Zirconocene.

Anal. calc. for $C_{51}H_{64}Cl_2OSiZr$: C, 69.35; H, 7.30. Found: C, 69.59; H, 7.35.

$^1$H NMR (CDCl$_3$): δ 7.61 (s, 1H, 7-H in $L^1$), 7.61-7.58 (m, 2H, 2,6-H in $C_6H_4{}^tBu$), 7.48-7.44 (m, 5H, 5-H in $L^1$, 2,6-H in $C_6H_3{}^tBu_2$, 3,5-H in $C_6H_4{}^tBu$), 7.37 (t, J=1.6 Hz, 1H, 4-H in $C_6H_3{}^tBu_2$), 7.34 (d, J=7.7 Hz, 5-H in $L^2$), 6.95 (s, 1H, 3-H in $L^2$), 6.94 (s, 1H, 3-H in $L^1$), 6.41 (d, J=7.7 Hz, 1H, 6-H in $L^2$), 3.90 (s, 3H, OMe), 2.30 (s, 3H, 2-Me in $L^2$), 2.11 (s, 3H, 2-Me in $L^1$), 1.35 (s, 9H, $^tBu$ in $C_6H_4{}^tBu$), 1.34 (s, 3H, SiMeMe'), 1.33 (s, 9H, 6-$^tBu$ in $L^1$), 1.33 (s, 18H, $^tBu$ in $C_6H_3{}^tBu_2$), 1.26 (s, 3H, SiMeMe').

Syn-Zirconocenes.

Anal. calc. for $C_{51}H_{64}Cl_2OSiZr$: C, 69.35; H, 7.30. Found: C, 69.51; H, 7.49.

$^1$H NMR (CDCl$_3$): δ 7.77 (s, 1H, 7-H in $L^1$), 7.52-7.50 (m, 2H, 2,6-H in $C_6H_4{}^tBu$), 7.46-7.44 (m, 4H, 3,5-H in $C_6H_4{}^tBu$ and 2,6-H in $C_6H_3{}^tBu_2$), 7.34 (s, 1H, 5-H in $L^1$), 7.28 (s, 1H, 4-H in $C_6H_3{}^tBu_2$), 7.13 (d, J=7.8 Hz, 5-H in $L^2$), 6.89 (s, 1H, 3-H in $L^2$), 6.87 (s, 1H, 3-H in $L^1$), 6.31 (d, J=7.8 Hz, 1H, 6-H in $L^2$), 4.01 (s, 3H, OMe), 2.48 (s, 3H, 2-Me in $L^2$), 2.44 (s, 3H, 2-Me in $L^1$), 1.36 (s, 9H, $^tBu$ in $C_6H_4{}^tBu$), 1.33 (s, 21H, $^tBu$ in $C_6H_3{}^tBu_2$ and SiMeMe'), 1.21 (s, 12H, 6-$^tBu$ in $L^1$ and SiMeMe').

Complex Synthesis of MC4

1-methoxy-2-methyl-4-Bromo-6-tert-butyl-indane

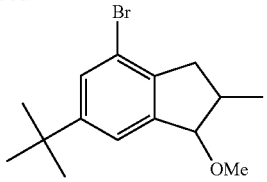

To a mixture of 260 g (925 mmol) of 2-methyl-4-bromo-6-tert-butylindan-1-one and 18 g (476 mmol) of NaBH$_4$ in 1000 ml of THF 500 ml of methanol was added dropwise by vigorous stirring for 5 h at 0-5° C. This mixture was stirred overnight at room temperature. The resulting mixture was evaporated to dryness, and the residue wad partitioned between 1000 ml of dichloromethane and 1000 ml of 0.5 M HCl. The organic layer was separated, the aqueous layer was additionally extracted with 2×250 ml of dichloromethane. The combined organic extract was dried over Na$_2$SO$_4$ and evaporated to dryness to give a colourless oil. The resulting oil was dissolved in 1200 ml of DMSO, then 207 g (3.69 mol) of KOH and 262 g (1.85 mol) of MeI were added. This mixture was stirred overnight at ambient temperature. Further on, the solution was decanted from an excess of KOH, the latter was washed with 3×300 ml of dichloromethane, and 4000 cm$^3$ of water was added to the combined organic solution. The organic layer was separated, and the aqueous layer was additionally extracted with 3×300 ml of dichloromethane. The combined organic extract was washed with 5×2000 ml of water, dried over Na$_2$SO$_4$, and evaporated to dryness. Fractional distillation of the residue in vacuum gave 266 g (97%) of a yellowish oily liquid of 1-methoxy-2-methyl-4-bromo-6-tert-butyl-indane (as a ca. 3 to 2 mixture of two diastereomers), b.p. 157-158° C./10 mm Hg.

Anal. calc. for $C_{15}H_{21}BrO$: C, 60.61; H, 7.12. Found: C, 60.43; H, 6.25.

Anti-Isomer $^1$H NMR (CDCl$_3$): δ 7.43 (s, 1H, 5-H), 7.31 (s, 1H, 7-H), 4.43 (d, J=4.3 Hz, 1H, 1-H), 3.45 (s, 3H, OMe), 3.18 (dd, J=16.3 Hz, J=7.76 Hz, 1H, 3-H), 2.50 (m, 1H, 2-H), 2.40 (dd, J=16.3 Hz, J=5.31 Hz, 1H, 2-H), 1.3 (s, 9H, 6-$^tBu$), 1.17 (d, J=6.94 Hz, 2-Me).

Syn-Isomer $^1$H NMR (CDCl$_3$): δ 7.41 (s, 1H, 5-H), 7.30 (s, 1H, 7-H), 4.56 (d, J=5.5 Hz, 1H, 1-H), 3.41 (s, 3H, OMe), 2.90 (dd, J=17.6 Hz, J=8.98 Hz, 1H, 3-H), 2.63 (m, 2H, 3'-H and 2-H), 1.3 (s, 9H, 6-$^tBu$), 1.07 (d, J=6.52 Hz, 2-Me).

$^{13}$C{$^1$H} NMR (CDCl$_3$)[1]: δ (152.10, 151.80, tert.), (144.15, 143.73, tert.), (140.41, 140.28, tert.), (128.63, 128.33, CH), (121.04, 120.91, CH), (120.09, 120.05, tert.), (92.15, 86.86, OMe), (56.91, 56.45, CH), (39.28, 38.95, CH$_2$), (39.19, 37.84, CH), 34.69 (2 tert.), 31.39 (2 $^tBu$), (19.43, 13.53, CH$_3$).

[1] Signals in brackets refer to the signals of chemically equivalent carbon atom from the two diastereomers.

2-methyl-5-tert-Butyl-7-(3,5-di-tert-butylphenyl)-1H-indene

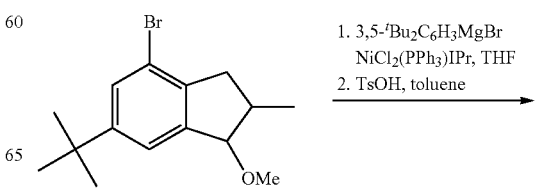

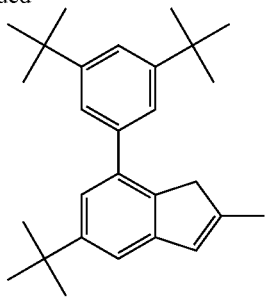

To a solution of 3,5-di-tert-butylphenylmagnesium bromide (obtained from 59.3 g (0.220 mom)) of 1-bromo-3,5-di-tert-butylbenzene and 7.60 g (0.313 mol, 1.42 eq.) of magnesium turnings in 500 ml of THF) 1.10 g (1.40 mmol, 0.7 mol. %) of $NiCl_2(PPh_3)IPr$ and a solution of 59.2 g (0.199 mol) of 1-methoxy-2-methyl-4-bromo-6-tert-butyl-indane in 50 ml of THF were added. A moderate reflux occurs after gentle warming of the reaction mixture which ceased after the following minute. This mixture was refluxed for 1 h, and then 600 ml of water was added. The product was extracted with 1000 ml of dichloromethane. The organic layer was separated, the aqueous layer was additionally extracted with 250 ml of dichloromethane. The combined organic extract was evaporated to dryness to give a yellowish oil with some amount of precipitate. This product was dissolved in 800 ml of toluene, 1.4 g of TsOH was added. The obtained solution was refluxed using a Dean-Stark head for 15 min, then additional 1.0 g of TsOH was added, and this mixture was refluxed for another 20 min. The latter procedure was repeated one more time. Further on, the obtained mixture was washed by 200 ml of 10% aqueous $NaHCO_3$. The organic layer was separated, the aqueous layer was additionally extracted with 2×100 ml of dichloromethane. The combined organic solution was evaporated to dryness. The residue was dissolved in 300 ml of dichloromethane, and the formed solution was passed through a short pad of silica gel 60 (40-63 um). The filtrate was evaporated to dryness. The product was isolated by re-crystallization of the residue from 200 ml of hot n-hexane. Crystals precipitated at room temperature were collected and then dried in vacuum. This procedure gave 42.7 g of 5-tert-butyl-7-(3,5-di-tert-butylphenyl)-2-methyl-1H-indene. The mother liquor was evaporated, and the residue was re-crystallized from 100 ml of hot n-hexane. Crystals precipitated at room temperature were collected and then dried in vacuum. This procedure gave additional 20.8 g of the title product. Again, the mother liquor was evaporated, the residue dried was dried in vacuum from 1,3-di-tert-butylbenzene, then re-crystallized from 35 ml of hot n-hexane to give 6.04 g of the target indene. Finally, 1.77 g of the product (containing a small amount of the isomeric indene) was isolated via re-crystallization of the residue obtained from evaporated mother liquor from 5 ml of n-hexane. Thus, the total yield of the title product was 71.3 g (96%).

Anal. calc. for $C_{28}H_{38}$: C, 89.78; H, 10.22. Found: C, 89.91; H, 10.41.

$^1$H NMR ($CDCl_3$): δ 7.42 (t, J=1.8 Hz, 1H, 4-H in $C_6H_3{}^tBu_2$), 7.38 (d, J=1.8 Hz, 2H, 2,6-H in $C_6H_3{}^tBu_2$), 7.30 (d, J=1.7 Hz, 1H, 6-H in indenyl), 7.19 (d, J=1.7 Hz, 1H, 4-H in indenyl), 6.52 (m, 1H, 3-H in indenyl), 3.34 (s, 2H, 1-H in indenyl), 2.12 (s, 3H, 2-Me in indenyl), 1.39 (s, 9H, 5-$^t$Bu in indenyl), 1.38 (s, 18H, $^t$Bu in $C_6H_3{}^tBu_2$).

[2-methyl-4-(3,5-di-tert-butylphenyl)-6-tert-butyl-1H-inden-1-yl](chloro)dimethylsilane

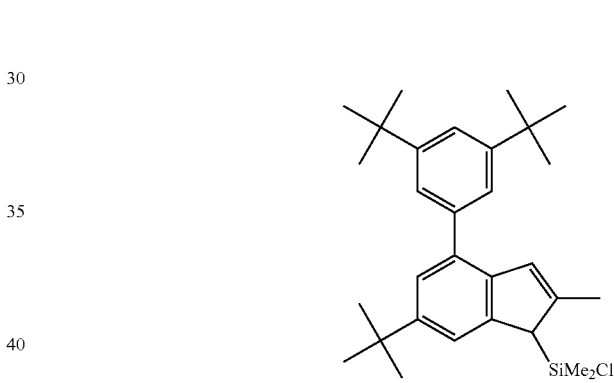

To a solution of 14.1 g (37.5 mmol) of 2-methyl-5-tert-butyl-7-(3,5-di-tert-butylphenyl)-1H-indene in mixture of 200 ml of toluene and 10 ml of THF 15.0 ml (37.5 mmol) of 2.5 M $^n$BuLi in hexanes was added at room temperature. The resulting mixture was stirred for 2 h at 60° C., then cooled to −20° C., and 25.0 g (194 mmol, 5 eq.) of dichlorodimethylsilane was added in one portion. The formed mixture was warmed to room temperature, refluxed for 0.5 h, and then filtered through glass frit (G3). The precipitate was additionally washed by 2×30 ml of toluene. The combined filtrate was evaporated to dryness to give 17.5 g (99%) of [2-methyl-4-(3,5-di-tert-butylphenyl)-6-tert-butyl-1H-inden-1-yl](chloro)dimethylsilane as colorless thick oil which was further used without an additional purification.

Anal. calc. for $C_{30}H_{43}ClSi$: C, 77.12; H, 9.28. Found: C, 77.39; H, 9.20.

$^1$H NMR ($CDCl_3$): δ 7.57 (s, 1H, 5-H in indenyl), 7.50 (t, J=1.6 Hz, 1H, 4-H in $C_6H_3{}^tBu_2$), 7.44 (d, J=1.6 Hz, 2H, 2,6-H in $C_6H_3{}^tBu_2$), 7.40 (d, J=1.6 Hz, 1H, 7-H in indenyl), 6.83 (m, 1H, 3-H in indenyl), 3.71 (s, 1H, 1-H in indenyl), 2.33 (s, 3H, 2-Me in indenyl), 1.47 (s, 18H, $^t$Bu in $C_6H_3{}^tBu_2$), 1.47 (s, 9H, 6-$^t$Bu in indenyl), 0.52 (s, 3H, SiMeMe'Cl), 0.26 (s, 3H, SiMeMe'Cl).

[2-methyl-4-(3,5-di-tert-butylphenyl)-6-tert-Butyl-1H-inden-1-yl][2-methyl-4-(4-tert-butylphenyl)-1H-inden-1-yl]dimethylsilane

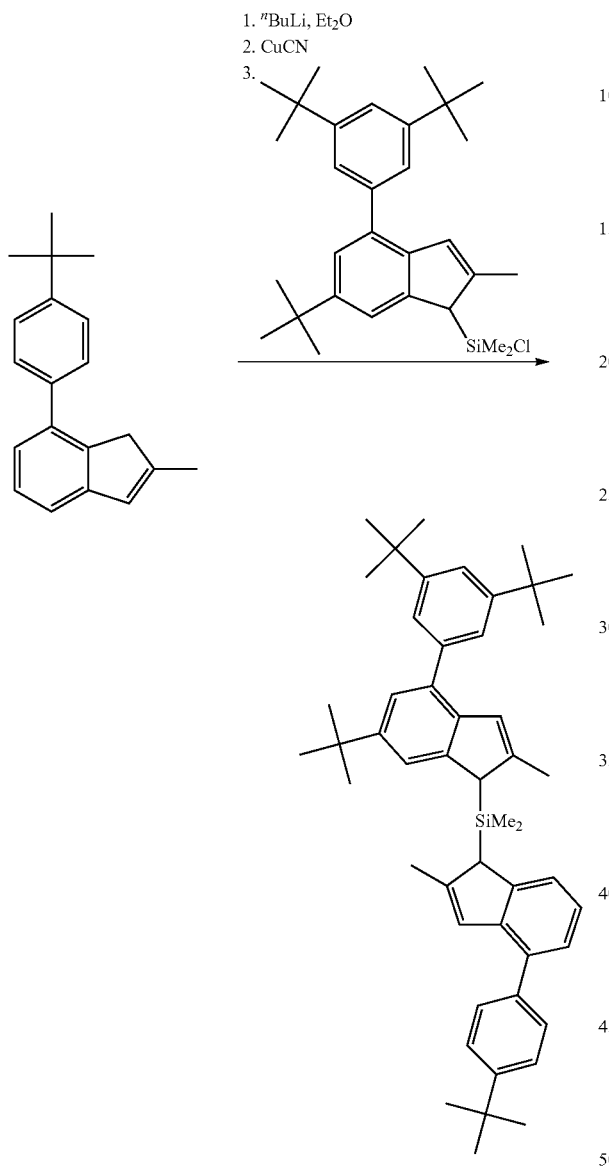

To a solution of 9.84 g (37.5 mmol) of 2-methyl-7-(4-tert-butylphenyl)-1H-indene in 200 ml of ether 15.0 ml (37.5 mmol) of 2.5 M $^n$BuLi in hexanes was added in one portion at −40° C. This mixture was stirred overnight at room temperature, then cooled to −40° C., and 200 mg of CuCN was added. The resulting mixture was stirred for 1 h at −20° C., then cooled to −40° C., and a solution of 17.5 g (37.5 mmol) of [2-methyl-4-(3,5-di-tert-butylphenyl)-6-tert-butyl-1H-inden-1-yl](chloro)dimethylsilane in 200 ml of ether was added in one portion. Further on, this mixture was stirred overnight at ambient temperature, then 0.5 ml of water were added. This solution was filtered through a pad of silica gel 60 (40-63 um) which was additionally washed by 2×75 ml of dichloromethane. The combined filtrate was evaporated under the reduced pressure, and the residue was dried in vacuum at elevated temperature. This procedure gave 26.1 g of [2-methyl-4-(3,5-di-tert-butylphenyl)-6-tert-butyl-1H-inden-1-yl][2-methyl-4-(4-tert-butylphenyl)-1H-inden-1-yl]dimethylsilane (on the evidence of NMR spectroscopy it has >90% purity and is a ca. 1:1 mixture of the diastereomers) as yellowish glass which was further used without an additional purification.

Anal. calc. for $C_{30}H_{43}ClSi$: C, 86.64; H, 9.31. Found: C, 86.90; H, 9.62.

$^1$H NMR (CDCl$_3$): δ 7.53 (s), 7.48-7.23 (m), 7.18-7.13 (m), 6.84 (s), 6.83 (s), 6.76 (s), 3.77 (s), 3.76 (s), 2.24 (s), 2.23 (s), 2.20 (s), 1.40 (s), 1.40 (s), 1.39 (s), 1.37 (s), 1.36 (s), −0.17 (s), −0.18 (s), −0.19 (s), −0.22 (s).

Dimethylsilanediyl[2-methyl-4-(4-tert-butylphenyl)inden-1-yl]-[2-methyl-6-tert-butyl-4-(3,5-di-tert-butylphenyl)inden-1-yl]zirconium dichloride (complex MC4)

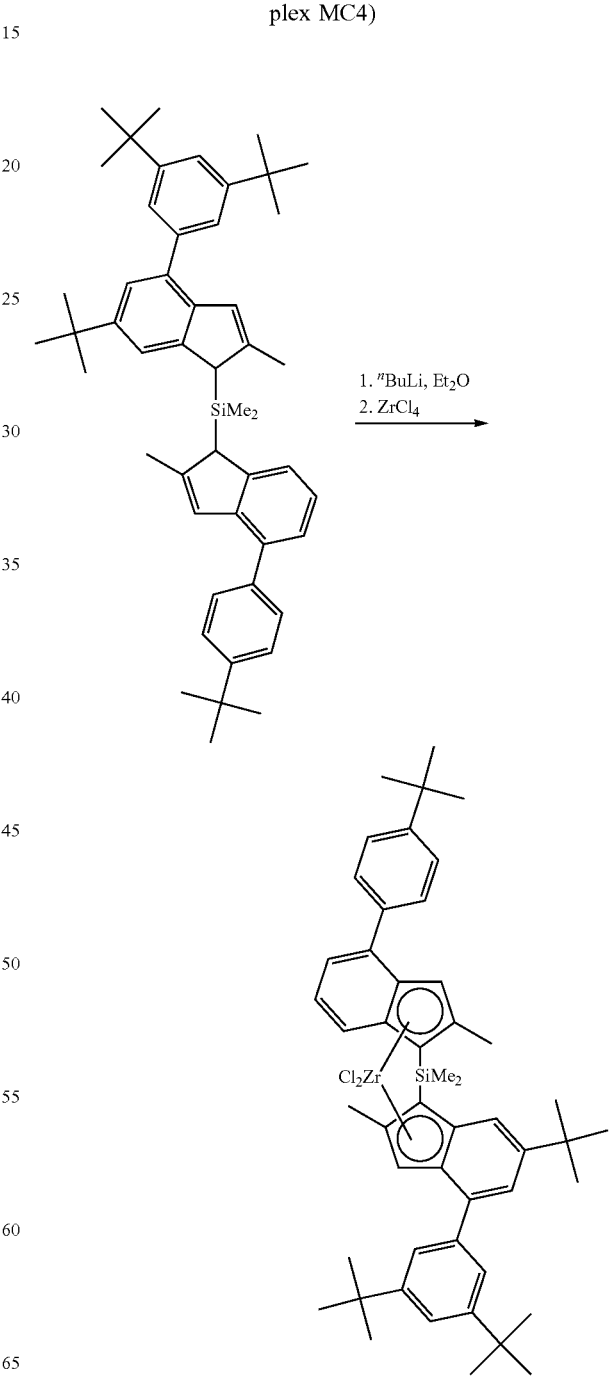

To a solution of 26.1 g (ca. 37.5 mmol) of [2-methyl-4-(3,5-di-tert-butylphenyl)-6-tert-butyl-1H-inden-1-yl][2-methyl-4-(4-tert-butylphenyl)-1H-inden-1-yl]dimethylsilane (prepared as described above) in 180 ml of ether 30.0 ml (75.0 mmol) of 2.5 M $^n$BuLi in hexanes was added in one portion. This mixture was stirred overnight at room temperature, then cooled to −50° C., and 8.74 g (37.5 mmol) of ZrCl$_4$ was added. The reaction mixture was stirred for 24 h, then evaporated to dryness, and the residue was dissolved in 250 ml of warm toluene. The formed hot suspension was filtered through glass frit (G4). On the evidence of NMR spectroscopy the filtrate included a ca. 1 to 1 mixture of anti- and syn-zirconocenes. This solution was evaporated to 50 ml, then 200 ml of n-hexane was added. Crystals precipitated at room temperature were collected and dried in vacuum. This procedure gave 4.00 g (13%) of syn-zirconocene which contained ca. 2% of anti-isomer. The mother liquor was evaporated to dryness, and the residue was dissolved in 50 ml of hot toluene. Crystals precipitated at room temperature were collected and dried in vacuum. This procedure gave anti-zirconocene with 5% admixture of syn-isomer. Additionally, two portions of anti-zirconocene with the same content of syn-isomer were obtained by successive addition of small amount of n-hexane to the filtrate. This procedure gave totally 7.80 g of anti-zirconocene contaminated with syn-zirconocene. This crude product was re-crystallized from 60 ml of a ca. 1 to 1 mixture of toluene-n-hexane. Thus, 3.61 g (11%) of pure anti-zirconocene as mono-solvate with toluene was isolated. The combined mother liquor was evaporated to dryness, and to the residue 100 ml of n-hexane was added. The formed precipitate was separated and then dried in vacuum. This procedure gave 21.0 g of a ca. 1 to 1 mixture of anti- and syn-zirconocenes. Thus, the total yield of the isolated ansa-zirconocenes was 28.6 g (89%). Assignment in NMR spectra was made using the following abbreviations: $L^1$ for 2-methyl-4-(4-tert-butylphenyl)-1H-inden-1-yl and $L^2$ for 2-methyl-4-(3,5-di-tert-butylphenyl)-6-tert-butyl-1H-inden-1-yl.

Anti-Zirconocene, Toluene Mono-Solvate.

Anal. calc. for $C_{57}H_{70}Cl_2SiZr$: C, 72.42; H, 7.46. Found: C, 72.08; H, 7.23.

$^1$H NMR (CDCl$_3$): δ 7.64 (d, J=8.5 Hz, 1H, 7-H in $L^1$), 7.60-7.58 (m, 3H, 2,6-H in $C_6H_4{}^t$Bu and 7-H in $L^2$), 7.51 (s, 1H, 5-H in $L^2$), 7.48 (d, J=1.25 Hz, 2H, 3,5-H in $C_6H_3{}^t$Bu$_2$), 7.45-7.42 (m, 3H, 3,5-H in $C_6H_4{}^t$Bu and 4-H in $C_6H_3{}^t$Bu$_2$), 7.38 (d, J=7.0 Hz, 1H, 5-H in $L^1$), 7.08 (dd, J=8.5 Hz, J=7.0 Hz, 1H, 6-H in $L^1$), 6.99 (s, 1H, 3-H in $L^1$), 6.88 (s, 1H, 3-H in $L^2$), 2.29 (s, 3H, 2-Me in $L^2$), 2.25 (s, 3H, 2-Me in $L^1$), 1.36-1.32 (m, 42H, SiMeMe', SiMeMe', $^t$Bu in $C_6H_4{}^t$Bu, 6-$^t$Bu in $L^2$, $^t$Bu in $C_6H_3{}^t$Bu$_2$).

Syn-Zirconocene.

Anal. calc. for $C_{50}H_{62}Cl_2SiZr$: C, 70.38; H, 7.32. Found: C, 70.48; H, 7.41.

$^1$H NMR (CDCl$_3$): δ 7.67 (d, J=8.5 Hz, 1H, 7-H in $L^1$), 7.55 (s, 1H, 7-H in $L^2$), 7.51 (d, J=8.1 Hz, 2H, 2,6-H in $C_6H_4{}^t$Bu), 7.44-7.40 (m, 5H, 5-H in $L^2$, 3,5-H in $C_6H_3{}^t$Bu$_2$, 3,5-H in $C_6H_4{}^t$Bu), 7.23 (m, 1H, 4-H in $C_6H_3{}^t$Bu$_2$), 7.10 (d, J=6.9 Hz, 1H, 5-H in $L^1$), 6.87-6.83 (m, 2H, 6-H in $L^1$ and 3-H in $L^1$), 6.74 (s, 1H, 3-H in $L^2$), 2.44 (s, 6H, 2-Me in $L^2$ and 2-Me in $L^1$), 1.47 (s, 3H, SiMeMe'), 1.34 (s, 18H, $^t$Bu in $C_6H_3{}^t$Bu$_2$), 1.34 (s, 9H, $^t$Bu in $C_6H_4{}^t$Bu), 1.27 (s, 9H, 6-$^t$Bu in $L^2$), 1.24 (s, 3H, SiMeMe').

Comparative Complex for Comparative Example CE1 rac-dimethylsilanediylbis(2-methyl-4-phenylindenyl)zirconium dichloride, described e.g. in EP-A-0576970, CAS no 153882-67-8, provided by Norquaytech. (CMC1)

Comparative Complex for Comparative Example CE2 metallocene rac-Me$_2$Si[2-Me-4-(3,5-$^t$Bu$_2$Ph)Ind]$_2$ZrCl$_2$ (CMC2)

7-(3,5-di-tert-butylphenyl)-2-methyl-1H-indene

To a solution of 3,5-di-tert-butylphenylmagnesium bromide obtained from 29.6 g (0.110 mol) of 1-bromo-3,5-di-tert-butylbenzene and 3.80 g (0.156 mol) of magnesium turnings in 200 ml of THF, 0.40 g (0.512 mmol, 0.5 mol. %) of NiCl$_2$(PPh$_3$)(IPr) and 24.1 g (0.10 mol) of 4-bromo-1-methoxy-2-methylindane were added. A vigorous reflux occurred approximately after 30 sec which ceased after the following 30 sec. This mixture was stirred at room temperature for 30 min. Finally, 1000 ml of water and then 50 ml of 12 M HCl were added. The product was extracted with 500 ml of dichloromethane, organic layer was separated, the aqueous layer was additionally extracted with 2×150 ml of dichloromethane. The combined organic extract was dried over K$_2$CO$_3$ and evaporated to dryness. To the residue dissolved in 300 ml of toluene 0.4 g of TsOH was added. The resulting solution was refluxed using Dean-Stark head for 15 min, then another 0.5 g of TsOH was added, and the obtained mixture was refluxed for 0.5 h. The reaction mixture was cooled to room temperature and then washed by 200 ml of 10% aqueous K$_2$CO$_3$.

The organic layer was separated, the aqueous layer was additionally extracted with 2×100 ml of dichloromethane. The combined organic extract was evaporated to dryness. The product was isolated by flash chromatography on silica gel 60 (40-63 um; eluent: hexane, then hexanedichloromethane=10:1, vol.). This procedure gave 31.9 g (99%) of 7-(3,5-di-tert-butylphenyl)-2-methyl-1H-indene as a white crystalline powder. The latter was recrystallized from n-hexane with almost no loss in mass.

Anal. calc. for $C_{24}H_{30}$: C, 90.51; H, 9.49. Found: C, 90.48; H, 9.44.

$^1$H NMR (CDCl$_3$): δ 7.41 (t, J=1.8 Hz, 1H, 4-H in 3,5-tBu$_2$C$_6$H$_3$), 7.37 (d, J=1.8 Hz, 2H, 2,6-H in 3,5-tBu$_2$C$_6$H$_3$), 7.31 (t, J=7.5 Hz, 1H, 5-H in indene), 7.24 (dd, J=7.5 Hz, J=1.0 Hz, 1H, 6-H in indene), 7.15 (dd, J=7.5 Hz, J=1.1 Hz, 1H, 4-H in indene), 6.54 (m, 1H, 3-H in indene), 3.38 (m, 2H, 1,1'-H in indene), 2.14 (m, 3H, 2-Me in indene), 1.38 (s, 18H, tBu).

Bis[4-(3,5-di-tert-butylphenyl)-2-methyl-1H-inden-1-yl]dimethylsilane 15.0 ml (37.5 mmol) of 2.5 M nBuLi in hexanes was added in one portion at room temperature to a solution of 11.9 g (37.5 mmol) of 7-(3,5-di-tert-butylphenyl)-2-methyl-1H-indene in 200 ml of toluene. This mixture was stirred overnight at room temperature, then 10 ml of THF was added, and the resulting mixture was refluxed for 2 h. The resulting mixture was cooled to room temperature, and 2.42 g (18.8 mmol) of dichlorodimethylsilane was added in one portion. Further on, this mixture was refluxed for 1 h, then 0.5 ml of water was added, and the formed solution was filtered through a pad of silica gel 60 (40-63 um) which was additionally washed by dichloromethane. The combined organic elute was evaporated to dryness and dried in vacuum. This procedure gave 13.0 g (100% of ca. 90% purity) of bis[4-(3,5-di-tert-butylphenyl)-2-methyl-1H-inden-1-yl]dimethylsilane as a yellowish glass. This product was further used without an additional purification.

Anal. calc. for $C_{50}H_{64}Si$: C, 86.64; H, 9.31. Found: C, 87.05; H, 9.55.

$^1$H NMR (CDCl3): δ 7.21-7.57 (m), 6.89 (m), 6.88 (m), 3.91 (s), 3.87 (s), 2.31 (s), 2.29 (s), 1.45 (s), 1.44 (s), −0.13 (s), −0.15 (s), −0.19 (s).

Rac-dimethylsilanediylbis[4-(3,5-di-tert-butylphenyl)-2-methyl-1H-inden-1-yl]zirconium dichloride

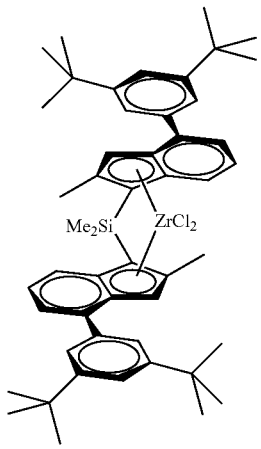

To a solution of 10.7 g (15.4 mmol) of bis[4-(3,5-di-tert-butylphenyl)-2-methyl-1H-inden-1-yl]dimethylsilane in 150 ml of toluene, 12.3 ml (30.8 mmol) of 2.5 M nBuLi in hexanes was added in one portion at room temperature. This mixture was stirred overnight at room temperature, the resulting light orange solution was then cooled to −25° C., and 5.81 g (15.4 mmol) of $ZrCl_4(THF)_2$ was added. The resulting dark red mixture was stirred for 24 h, then 10 ml of THF was added. The obtained mixture was stirred for 2 h at 60° C. After evaporation of ca. 50 ml of the solvents, the resulting solution warmed to 80° C. was filtered through glass frit (G4). The filtrate was evaporated to dryness, and then 250 ml of n-hexane was added to the residue. The obtained suspension was stirred overnight at room temperature and then filtered through a glass frit (G3). The filtrate was evaporated to dryness, and 25 ml of n-hexane was added to the residue. The formed yellow precipitate was filtered off, washed with 5×15 ml of n-hexane, and dried in vacuum. This procedure gave rac-zirconocene contaminated with ca. 4% of meso-form. To purify it, this product was dissolved in 20 ml of hot toluene, and to the obtained solution 100 ml of n-hexane was added. The formed precipitate was filtered off and then dried in vacuum. This procedure gave 2.29 g (17%) of pure rac-complex.

Anal. calc. for $C_{50}H_{62}Cl_2SiZr$: C, 70.38; H, 7.32. Found: C, 70.29; H, 7.38.

$^1$H NMR (CDCl$_3$): δ 7.66 (d, J=8.4 Hz, 2H, 5-H in indenyl), 7.54 (m, 4H, 2,6-H in 3,5-tBu$_2$C$_6$H$_3$), 7.40-7.43 (m, 4H, 7-H in indenyl and 4-H in 3,5-tBu$_2$C$_6$H$_3$), 7.12 (dd, J=8.4 Hz, J=6.9 Hz, 2H, 6-H in indenyl), 6.97 (s, 2H, 3-H in indenyl), 2.26 (s, 6H, 2-Me in indenyl), 1.34 (s, 6H, SiMe$_2$), 1.32 (s, 36H, tBu).

Comparative Complex for Comparative Example CE3 rac-dimethylsilanediylbis(2-methyl-4-(3,5-di-tert-butylphenyl)-7-methoxyindenyl)zirconium dichloride (CMC3)

rac-dimethylsilanediylbis(2-methyl-4-(3,5-di-tert-butyl-phenyl)-7-methoxyindenyl)zirconium dichloride was synthesized as described by Schobel, Rieger et al. in Chemistry-A European Journal, vol. 18, pages 4174-4178 (2012).

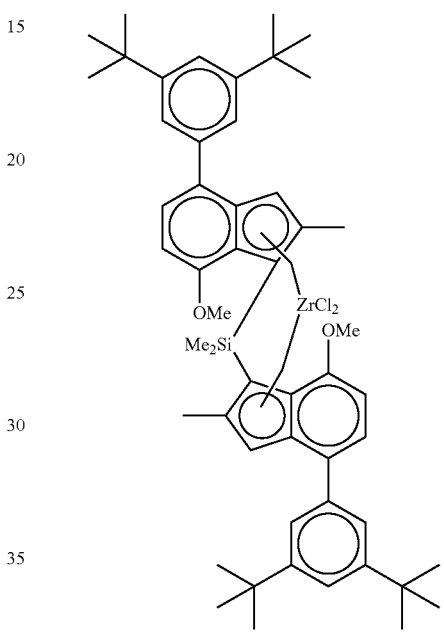

Catalyst Example E1, metallocene MC1 rac-anti-Me$_2$Si(2-Me-4-(3,5-tBu$_2$Ph)-7-OMe-Ind)(2-Me-4-(p-tBuPh)-Ind)ZrCl$_2$ Inside the glovebox, 80 μL of dry and degassed surfactant solution were mixed with 2 mL of MAO in a septum bottle and left to react overnight. The following day, 62.9 mg of the metallocene MC1 (0.076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.45 g of a purple free flowing powder was obtained.

Catalyst Example E2, Metallocene MC2

Catalyst was prepared in the same manner as E1 using 61.7 mg of metallocene MC2. 0.45 g of a red free flowing powder was obtained.

Catalyst Example E3, Metallocene MC3

Catalyst was prepared in the same manner as E1 using 67.3 mg of metallocene MC3. 0.55 g of a purple free flowing powder was obtained.

Catalyst Example E4, Metallocene MC4

Catalyst was prepared in the same manner as E1 using 64.9 mg of metallocene MC2. 0.41 g of a red free flowing powder was obtained.

Comparative Example CE1, Metallocene CMC1 rac-dimethylsilanediylbis(2-methyl-4-phenylindenyl) zirconium dichloride

Inside the glovebox, 80 µL of dry and degassed surfactant solution were mixed with 2 mL of MAO in a septum bottle and left to react overnight. The following day, 47.8 mg of the metallocene. rac-dimethylsilanediylbis(2-methyl-4-phenyl-indenyl)zirconium dichloride, (0.076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately and stirred during 15 minutes at 0° C./600 rpm.

Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.51 g of a red free flowing powder was obtained.

Comparative Example CE2, Metallocene CMC2 rac-Me$_2$Si[2-Me-4-(3,5-$^t$Bu$_2$Ph)Ind]$_2$ZrCl$_2$

Inside the glovebox, 80 µL of dry and degassed surfactant solution were mixed with 2 mL of MAO in a septum bottle and left to react overnight. The following day, 64.9 mg of the metallocene rac-Me$_2$Si[2-Me-4-(3,5-$^t$Bu$_2$Ph)Ind]$_2$ZrCl$_2$/MAO (0.076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.45 g of a red free flowing powder was obtained.

Comparative Example CE3, Metallocene rac-Me$_2$Si[2-Me-4-(3,5-$^t$Bu$_2$Ph)-7-OMe-Ind]$_2$ZrCl$_2$ Inside the glovebox, 80 µL of dry and degassed surfactant solution were mixed with 2 mL of MAO in a septum bottle and left to react overnight. The following day, 69.4 mg of the metallocene, rac-Me$_2$Si[2-Me-4-(3,5-$^t$Bu$_2$Ph)-7-OMe-Ind]$_2$ZrCl$_2$/MAO, (0.076 mmol, 1 equivalent) were dissolved with 4 mL of the MAO solution in another septum bottle and left to stir inside the glovebox.

After 60 minutes, 1 mL of the surfactant solution and the 4 mL of the MAO-metallocene solution were successively added into a 50 mL emulsification glass reactor containing 40 mL of PFC at −10° C. and equipped with an overhead stirrer (stirring speed=600 rpm). Total amount of MAO is 5 mL (300 equivalents). A red-orange emulsion formed immediately and stirred during 15 minutes at 0° C./600 rpm. Then the emulsion was transferred via a 2/4 teflon tube to 100 mL of hot PFC at 90° C., and stirred at 600 rpm until the transfer is completed, then the speed was reduced to 300 rpm. After 15 minutes stirring, the oil bath was removed and the stirrer turned off. The catalyst was left to settle up on top of the PFC and after 45 minutes the solvent was siphoned off. The remaining red catalyst was dried during 2 hours at 50° C. over an argon flow. 0.74 g of a red free flowing powder was obtained.

Catalyst properties are described in Table 1

| Catalyst name | Zr (%) | Al (%) | Al/Zr (molar) |
|---|---|---|---|
| E1 | 0.36 | 26.60 | 250 |
| E2 | 0.33 | 27.90 | 286 |
| E3 | 0.35 | 26.30 | 254 |
| E4 | 0.32 | 29.00 | 306 |
| CE1 | 0.25 | 18.6 | 251 |
| CE2 | 0.29 | 24.0 | 280 |
| CE3 | 0.29 | 23.7 | 276 |

Polymerisations

Homopolymerisation

The polymerisations were performed in a 5 L reactor. 200 µL of triethylaluminum was fed as a scavenger in 5 mL of dry and degassed pentane. The desired amount of hydrogen was then loaded (measured in mmol) and 1100 g of liquid propylene was fed into the reactor.

Procedure A: The temperature was set to 30° C. The desired amount of catalyst (5 to 30 mg) in 5 mL of PFC is flushed into the reactor with a nitrogen overpressure. The temperature is then raised to 70° C. over a period of 15 minutes. The polymerisation is stopped after 30 minutes by venting the reactor and flushing with nitrogen before the polymer is collected.

Procedure B: The temperature was set to 20° C. The desired amount of catalyst (3 to 30 mg) in 5 mL of PFC is flushed into the reactor with a nitrogen overpressure. After 5 minutes of the temperature is raised to 70° C. over a period of 15 minutes. The polymerisation is stopped after 60 minutes by venting the reactor and flushing with nitrogen before the polymer is collected.

The catalyst activity was calculated on the basis of the 30 (or 60) minutes period according to the following formula:

$$\text{Catalyst Activity}(\text{kg}/(\text{g(cat)} * \text{h})) = \frac{\text{amount of polymer produced}(\text{kg})}{\text{catalyst loading}(\text{g}) \times \text{polymerisation time}(\text{h})}$$

Homopolymerisation results are disclosed in table 2

TABLE 2

Homopolymerization results with catalyst CE1, CE2, CE3 and E1, E2, E3, E4, Polymerisations PC1-PC9, and PE1-PE12

| Catalyst type | | Cat. (mg) | Time (min) | $H_2$ (mmol)*** | Pol. Yield (g) | A cat (kg/g/h) | A Mt (kg/gMt/h) | $MFR_2$ (g/10) | $M_w$ (kg/mol) | $M_w/M_n$ | $T_m$ (° C.) | $T_c$ (° C.) |
|---|---|---|---|---|---|---|---|---|---|---|---|---|
| CE1 | PC1 | 13.5 | 30 | 1 | 61 | 9.1 | 3639 | 3.6** | 676 | 2.4 | 149.3 | 110.5 |
| | PC2 | 22.9 | 60* | 6 | 178 | 7.8 | 3106 | 64.0** | 382 | 2.4 | 150.1 | 106.5 |
| | PC3 | 25.4 | 60* | 15 | 206 | 8.1 | 3249 | 4.8 | 252 | 2.6 | 150.7 | 108.9 |
| CE2 | PC4 | 11.1 | 60* | 1 | 99 | 9.0 | 3088 | 9.4** | 574 | 2.5 | 156.5 | 111.9 |
| | PC5 | 5.5 | 60* | 6 | 100 | 18.2 | 6270 | 1.9 | 302 | 2.4 | 158.9 | 112.2 |
| | PC6 | 10.7 | 60* | 15 | 218 | 20.4 | 7025 | 21.0 | 179 | 2.4 | 156.6 | 112.7 |
| CE3 | PC7 | 18.3 | 30 | 1 | 50 | 5.5 | 1888 | 1.9 | 347 | 2.0 | 159.4 | 113.5 |
| | PC8 | 16.1 | 30 | 6 | 120 | 15.0 | 5157 | 19.0 | 190 | 2.1 | 156.2 | 113.8 |
| | PC9 | 13.6 | 30 | 15 | 114 | 16.8 | 5781 | 120 | 106 | 2.2 | 156.6 | 116.5 |
| E1 | PE1 | 11.2 | 60* | 1 | 146 | 13.0 | 3624 | 17.0** | 483 | 2.6 | 150.7 | 110.4 |
| | PE2 | 9.3 | 60* | 6 | 252 | 27.1 | 7518 | 2.0 | 308 | 2.5 | 153.8 | 109.0 |
| | PE3 | 15.1 | 60* | 15 | 408 | 27.0 | 7506 | 14.0 | 203 | 2.5 | 151.2 | 111.4 |
| E2 | PE4 | 10.8 | 60* | 1 | 154 | 14.3 | 4332 | 22.0** | 481 | 2.4 | 148.9 | 109.3 |
| | PE5 | 9.6 | 60* | 6 | 247 | 25.8 | 7809 | 120.0** | 303 | 2.4 | 150.4 | 111.2 |
| | PE6 | 10.0 | 60* | 15 | 299 | 29.9 | 9067 | 13.0 | 204 | 2.4 | 149.6 | 110.3 |
| E3 | PE7 | 10.2 | 60* | 1 | 153 | 15.0 | 4277 | 19.0** | 607 | 2.1 | 148.3 | 109.0 |
| | PE8 | 10.4 | 60* | 6 | 264 | 25.4 | 7245 | 2.7 | 316 | 2.3 | 149.6 | 107.2 |
| | PE9 | 9.7 | 60* | 15 | 294 | 30.3 | 8669 | 21.0 | 174 | 2.5 | 149.8 | 110.4 |
| E4 | PE10 | 10.2 | 60* | 1 | 143 | 14.1 | 4393 | 9.4** | 756 | 2.3 | 148.4 | 107.7 |
| | PE11 | 9.6 | 60* | 6 | 239 | 24.9 | 7767 | 91.0** | 390 | 2.4 | 150.3 | 108.3 |
| | PE12 | 10.7 | 60* | 15 | 320 | 29.9 | 9352 | 11.0 | 220 | 2.4 | 149.2 | 109.7 |

*procedure B,
**$MFR_{21}$ (g/10 min),

Mt=metal present in the specified catalyst.
NMR results for homoPP from polymeriastion runs with 6 mmol H2 are disclosed in Table 3

TABLE 3

NMR results

| Catalyst Recipe | 2.1e % | mmmm % |
|---|---|---|
| E1 | 0.87 | 99.32 |
| E2 | 1.04 | 99.26 |
| E3 | 1.04 | 99.56 |
| E4 | 1.01 | 99.44 |
| CE3 | 0.45 | 99.06 |
| CE2 | 0.41 | 99.35 |
| CE1 | 0.98 | 99.14 |

Random Polymerisation

The polymerisations were performed in a 5 L reactor. 200 μl of triethylaluminum was fed as a scavenger in 5 mL of dry and degassed pentane. The desired amount of hydrogen (6 mmol) was then loaded (measured in mmol) and 1100 g of liquid propylene was fed into the reactor. The desired amount of ethylene was fed to the reactor.

Procedure A: The temperature was set to 30° C. The desired amount of catalyst (5 to 30 mg) in 5 mL of PFC is flushed into the reactor with a nitrogen overpressure. The temperature is then raised to 70° C. over a period of 15 minutes. The polymerisation is stopped after 30 minutes by venting the reactor and flushing with nitrogen before the polymer is collected.

Catalyst activity was defined as above on the basis of the 30 minutes period. Results of random polymerisation are disclosed in Table 4:

TABLE 4

C3/C2 random polymerisation results with CE2-CE3 and E1, E3 and E4.

| Catalyst Recipe | | Cat (mg) | $C_2$ (g) Feed | Polymer (g) yield | Activity (kg/(g(cat) * h)) | A Mt (kg/$g_{Mt}$/h) | $MFR_2$ (g/10 min) | $MFR_{21}$ (g/10 min) | $M_w$ (kg/mol) | $M_w/M_n$ | $T_m$ (° C.) | $T_c$ (° C.) | FTIR $C_2$ (wt.-%) | NMR $C_2$ (wt.-%) |
|---|---|---|---|---|---|---|---|---|---|---|---|---|---|---|
| E1 | PE13 | 11.7 | 19.9 | 306 | 52.3 | 14525 | 1.5 | | 345 | 2.3 | 139.3 | 99.7 | 1.5 | 1.6 |
| | PE14 | 9.6 | 39.9 | 144 | 30.1 | 8356 | 1.2 | | 356 | 2.6 | 128.0 | 90.0 | 3.1 | 3.0 |
| | PE15 | 10.6 | 50.0 | 135 | 25.5 | 7070 | 1.3 | | 344 | 2.7 | 122.8 | 84.9 | 4.4 | 3.7 |
| E3 | PE16 | 7.9 | 20.0 | 258 | 65.3 | 18662 | 2.8 | | 306 | 2.3 | 136.3 | 96.6 | 1.6 | 1.8 |
| | PE17 | 8.2 | 39.9 | 176 | 42.9 | 12251 | 2.7 | | 293 | 2.4 | 124.5 | 86.3 | 4.0 | 3.2 |
| | PE18 | 10.5 | 50.2 | 219 | 41.7 | 11918 | | 142.0 | 308 | 2.4 | 117.4 | 79.7 | 4.7 | 3.5 |
| E4 | PE19 | 10.6 | 19.9 | 295 | 55.7 | 17412 | 1.3 | 160.0 | 317 | 2.3 | 137.1 | 98.8 | 1.5 | 1.6 |
| | PE20 | 8.9 | 40.0 | 168 | 37.7 | 11770 | 2.1 | | 305 | 2.2 | 126.7 | 89.2 | 3.3 | 3.1 |
| | PE21 | 10.0 | 50.0 | 199 | 39.8 | 12431 | | 120.0 | 321 | 2.2 | 128.0 | 82.9 | 4.1 | 3.6 |
| CE2 | PC10 | 9.9 | 20.0 | 137 | 27.8 | 9572 | 4.9 | | 251 | 2.2 | 142.9 | 102.0 | 1.5 | 1.5 |
| | PC11 | 12.3 | 39.9 | 110 | 17.9 | 6162 | 11.0 | | 208 | 2.3 | 130.8 | 91.5 | 3.0 | 2.8 |
| | PC12 | 10.5 | 50.0 | 68 | 12.9 | 4433 | 13.0 | | 205 | 2.3 | 124.7 | 88.3 | 4.3 | 3.7 |
| CE3 | PC13 | 10.6 | 20.7 | 141 | 26.7 | 9193 | 7.7 | | 235 | 2.2 | 138.5 | 99.9 | 1.8 | 1.2 |
| | PC14 | 11.6 | 39.9 | 103 | 17.8 | 6124 | 4.1 | | 278 | 2.1 | 124.7 | 87.0 | 4.6 | n.d. |

Mt=metal present in the specified catalyst.

The invention claimed is:

1. A catalyst comprising
(i) an asymmetric complex of formula (I)

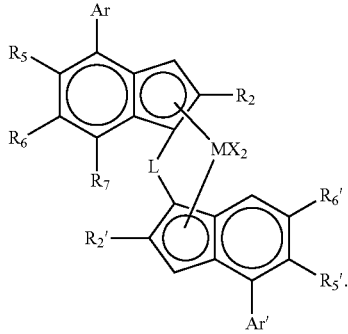

wherein

M is zirconium or hafnium;

each X is a sigma ligand;

L is a divalent bridge selected from the group consisting of —R'$_2$C—, —R'$_2$C—CR'$_2$—, —R'$_2$Ge—, wherein each R' is independently a hydrogen atom, C1-C20-alkyl, tri(C1-C20-alkyl)silyl, C6-C20-aryl, C7-C20-arylalkyl and C7-C20-alkylaryl;

R$_2$ and R$_{2'}$ are each independently linear C$_{1-10}$ hydrocarbyl;

R$_5$ and R$_{5'}$ are each independently hydrogen or a C1-20 hydrocarbyl group;

R$_6$ and R$_{6'}$ are each independently hydrogen or a C1-20 hydrocarbyl group;

R$_7$ is hydrogen or a C1-20 hydrocarbyl group or is ZR$_3$;

Z is O or S;

R$_3$ is a C1-10 hydrocarbyl group;

Ar is an aryl or heteroaryl group having up to 20 carbon atoms optionally substituted by one or more groups R$_8$;

Ar' is an aryl or heteroaryl group having up to 20 carbon atoms optionally substituted by one or more groups R$_{8'}$; and R$_8$ and R$_{8'}$ are each independently a C1-20 hydrocarbyl group;

with the proviso that at least one of R$_6$ and R$_7$ is not H; and (ii) a cocatalyst comprising a compound of a group 13 metal.

2. A catalyst as claimed in claim 1 wherein the complex is a racemic anti isomer.

3. A catalyst as claimed in claim 1 wherein R$_2$ is linear C1-6 alkyl.

4. A catalyst as claimed in claim 1 wherein one of R$_6$ and R$_7$ is H.

5. A catalyst as claimed in claim 1 wherein R$_5$ is H and R$_{5'}$ is H.

6. A catalyst as claimed in claim 1 wherein said complex is of formula (II)

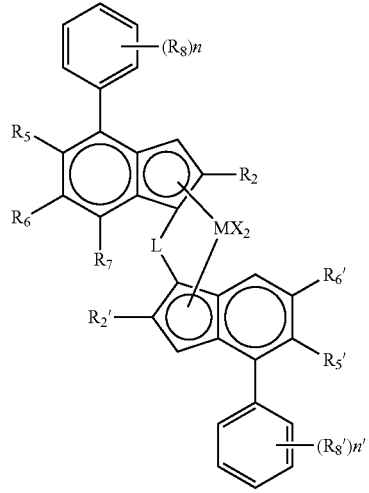

wherein

M is zirconium or hafnium;

each X is a sigma ligand;

L is a divalent bridge selected from the group consisting of —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl and C7-C20-alkylaryl;

R$_2$ and R$_{2'}$ are each independently linear C1-4 alkyl;

R$_5$ and R$_{5'}$ are each independently hydrogen or an aliphatic C1-10 hydrocarbyl group;

R$_6$ and R$_{6'}$ are each independently hydrogen or an aliphatic C1-10 hydrocarbyl group;

R$_7$ is hydrogen or an aliphatic C1-10 hydrocarbyl group or is ZR$_3$;

Z is O or S;

R$_3$ is a C1-10 alkyl group;

R$_8$ and R$_{8'}$ are each independently an aliphatic C1-20 hydrocarbyl group;

n is 0, 1, 2 or 3; and n' is 0, 1, 2 or 3;

with the proviso that one of R$_6$ and R$_7$ is not H.

7. A catalyst as claimed in claim 1 wherein said complex is of formula (III)

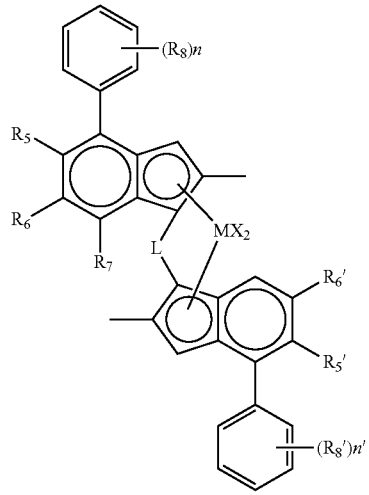

wherein

M is zirconium or hafnium;

each X is independently a hydrogen atom, a halogen atom, $C_{1-6}$-alkoxy group, $C_{1-6}$-alkyl, phenyl or benzyl group;

L is a divalent bridge selected from the group consisting of —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-alkyl, tri(C1-C20-alkyl)silyl, C6-C20-aryl, C7-C20-arylalkyl and C7-C20-alkylaryl;

$R_5$ and $R_{5'}$ are hydrogen or a C1-10 alkyl group;

$R_6$ and $R_{6'}$ are hydrogen or a C1-10 alkyl group;

$R_7$ is hydrogen or C1-10 alkyl group or is $OR_3$;

$R_3$ is a C1-10 alkyl group;

n is 1 to 3;

n' is 1 to 3;

and $R_8$ and $R_{8'}$ are an aliphatic C1-10 hydrocarbyl group;

with the proviso that one of $R_6$ and $R_7$ is not H.

8. A catalyst as claimed in claim 1 wherein said complex is of formula (IV):

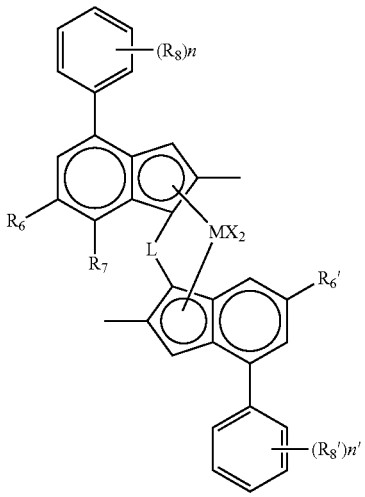

wherein

M is zirconium or hafnium;

each X is independently a hydrogen atom, a halogen atom, $C_{1-6}$-alkoxy group, $C_{1-6}$-alkyl, phenyl or benzyl group;

L is a divalent bridge selected from the group consisting of —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-hydrocarbyl, tri(C1-C20-alkyl)silyl, C6-C20-aryl, C7-C20-arylalkyl and C7-C20-alkylaryl;

$R_6$ is hydrogen or a C1-10 alkyl group;

$R_{6'}$ is hydrogen or a C1-10 alkyl group;

$R_7$ is hydrogen or C1-10 alkyl group or is $OR_3$;

$R_3$ is a C1-10 alkyl group;

n is 1 to 3;

n' is 1 to 3;

and $R_8$ and $R_{8'}$ are a C1-10 alkyl group;

with the proviso that one of $R_6$ and $R_7$ is not H.

9. A catalyst as claimed in claim 1 wherein said complex is of formula (V)

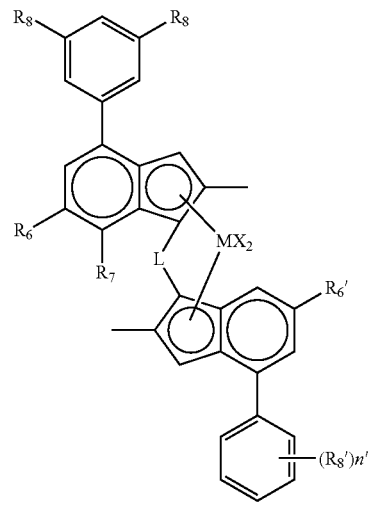

wherein L, M and X are as hereinbefore defined;

$R_6$ is hydrogen or a C1-6 alkyl group;

$R_{6'}$ is hydrogen or a C1-6 alkyl group;

$R_7$ is hydrogen or C1-6 alkyl group or is $OR_3$;

$R_3$ is a C1-6 alkyl group;

n' is 1 to 3;

and $R_8$ and $R_{8'}$ are a C1-10 alkyl;

with the proviso that one of $R_6$ and $R_7$ is not H.

10. A catalyst as claimed in claim 1 wherein said cocatalyst is MAO.

11. A catalyst as claimed in claim 1 in solid form.

12. A catalyst as claimed in claim 1 obtained by a process in which (a) a liquid/liquid emulsion system is formed, said liquid/liquid emulsion system comprising a solution of the catalyst components (i) and (ii) dispersed in a solvent so as to form dispersed droplets; and (b) solid particles are formed by solidifying said dispersed droplets.

13. A process for the manufacture of a catalyst as claimed in claim 1 comprising obtaining a complex of formula (I)(i) and a cocatalyst (ii);

forming a liquid/liquid emulsion system, which comprises a solution of catalyst components (i) and (ii) dispersed in a solvent so as to form dispersed droplets, and solidifying said dispersed droplets to form solid particles.

14. A process for the polymerisation of at least one olefin comprising polymerizing the at least one olefin in the presence of the catalyst of claim 1.

* * * * *